(12) United States Patent
Carter et al.

(10) Patent No.: US 11,470,846 B2
(45) Date of Patent: Oct. 18, 2022

(54) HERBICIDAL PYRIDINO-/PYRIMIDINO-THIAZOLES

(71) Applicant: SYNGENTA PARTICIPATIONS AG, Basel (CH)

(72) Inventors: Neil Brian Carter, Bracknell (GB); Alison Clare Elliott, Bracknell (GB); Derek McCormack, Bracknell (GB); Matthew Murdoch Woodhead McLachlan, Bracknell (GB); Anne Mary Seville, Bracknell (GB); Matthew John Webber, Bracknell (GB)

(73) Assignee: SYNGENTA PARTICIPATIONS AG, Basel (CH)

(*) Notice: Subject to any disclaimer, the term of this patent is extended or adjusted under 35 U.S.C. 154(b) by 394 days.

(21) Appl. No.: 16/814,320

(22) Filed: Mar. 10, 2020

(65) Prior Publication Data

US 2020/0253208 A1 Aug. 13, 2020

Related U.S. Application Data

(63) Continuation of application No. 15/514,048, filed as application No. PCT/EP2015/071419 on Sep. 18, 2015, now abandoned.

(30) Foreign Application Priority Data

Sep. 24, 2014 (GB) ..................................... 1416840
Jul. 8, 2015 (GB) ..................................... 1511932

(51) Int. Cl.
| | |
|---|---|
| *A01N 43/78* | (2006.01) |
| *A01N 47/18* | (2006.01) |
| *A01N 47/36* | (2006.01) |
| *C07D 213/76* | (2006.01) |
| *C07D 277/44* | (2006.01) |

(52) U.S. Cl.
CPC .............. *A01N 43/78* (2013.01); *A01N 47/18* (2013.01); *A01N 47/36* (2013.01); *C07D 213/76* (2013.01); *C07D 277/44* (2013.01)

(58) Field of Classification Search
None
See application file for complete search history.

(56) References Cited

U.S. PATENT DOCUMENTS

| 2013/0089622 A1 | 4/2013 | Trullinger et al. |
| 2014/0148471 A1 | 5/2014 | Bretschneider et al. |

FOREIGN PATENT DOCUMENTS

| JP | 2013119542 A2 | 6/2013 |
| WO | 9417059 A1 | 8/1994 |
| WO | 2010129497 A1 | 11/2010 |
| WO | 2012000896 A2 | 1/2012 |
| WO | 2013186089 A2 | 12/2013 |
| WO | 2015003895 A1 | 1/2015 |
| WO | 2015061151 A1 | 4/2015 |
| WO | 2015061155 A1 | 4/2015 |

OTHER PUBLICATIONS

Bertok et al, Pest Management Science, vol. 59, pp. 377-392, DOI: 10.1002/ps.644, online (Year: 2003).*

* cited by examiner

*Primary Examiner* — Zinna Northington Davis
(74) *Attorney, Agent, or Firm* — BakerHostetler; Toni-Junell Herbert

(57) ABSTRACT

The present invention relates to herbicidally active pyridino-/pyrimidino-thiazole derivatives, as well as to processes and intermediates used for the preparation of such derivatives. The invention further extends to herbicidal compositions comprising such derivatives, as well as to the use of such compounds and compositions in controlling undesirable plant growth: in particular the use in controlling weeds, in crops of useful plants.

12 Claims, No Drawings

HERBICIDAL PYRIDINO-/PYRIMIDINO-THIAZOLES

CROSS-REFERENCE TO RELATED APPLICATIONS

This application is a continuation of U.S. application Ser. No. 15/514,048, filed Mar. 24, 2017, which is a 371 of International Application No. PCT/EP2015/071419, filed 18 Sep. 2015, which claims priority to GB Application No. 1416840.5, filed 24 Sep. 2014 and GB Application No. 1511932.4, filed 8 Jul. 2015, the contents of which are incorporated herein by reference.

The present invention relates to herbicidally active pyridino-/pyrimidino-thiazole derivatives, as well as to processes and intermediates used for the preparation of such derivatives. The invention further extends to herbicidal compositions comprising such derivatives, as well as to the use of such compounds and compositions in controlling undesirable plant growth: in particular the use in controlling weeds, in crops of useful plants.

Herbicidal pyrimidino-imidazoles are known from WO2005/047281. Pyridino-/pyrimidino-thiazole derivatives, for use as acaricidal/insecticidal/molluscicidal/nematicidal agents, or in controlling invertebrate pests, are described in WO2010/129497, WO2011/128304, WO2013/186089, and WO2014/007395.

The present invention is based on the finding that pyridino-thiazole, and pyrimidino-thiazole, derivatives of formula (I) as defined herein, exhibit surprisingly good herbicidal activity.

Thus, in a first aspect of the invention there is provided the use of a compound of formula (I)

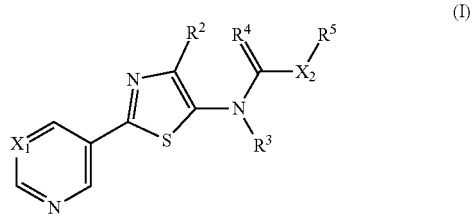

(I)

or a salt or N-oxide thereof, wherein, $X_1$ is N or $CR^1$;
$R^1$ is hydrogen, halogen, cyano, $C_1$-$C_6$ alkyl, $C_3$-$C_6$ cycloalkyl, $C_2$-$C_6$ alkenyl, $C_2$-$C_6$ alkynyl, $C_1$-$C_6$ alkoxy, $C(O)OR^6$ or $S(O)_n(C_1$-$C_6$ alkyl), formyl, hydroxyl, —$C(O)NR^6R^7$, $NR^6R^7$, benzyloxy, $C_1$-$C_6$ haloalkoxy, or $C_1$-$C_6$ haloalkyl;
$R^2$ is hydrogen, halogen, cyano, nitro, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, —$C(O)OR^6$, $S(O)_n(C_1$-$C_6$ alkyl), $C_1$-$C_6$ alkoxy, or $C_1$-$C_6$ haloalkoxy;
n is 0, 1, or 2;
$R^3$ is hydrogen, cyano, $C_1$-$C_6$ alkyl, $C_2$-$C_6$ alkenyl, $C_2$-$C_6$ alkynyl, $C_2$-$C_6$ haloalkenyl, $C_1$-$C_6$ alkoxy, $C_1$-$C_6$ haloalkyl, $C_1$-$C_6$ haloalkoxy, $C_2$-$C_6$ alkenyloxy, $C_3$-$C_{10}$ cycloalkyl, $NR^6R^7$, $R^4$ is O, S, or $N(C_1$-$C_6$ alkyl);
$X_2$ is O, S, or $NR^8$;
$R^5$ is hydrogen, $C_1$-$C_6$ alkyl, $C_2$-$C_6$ alkenyl, $C_2$-$C_6$ alkynyl, $C_3$-$C_{10}$ cycloalkyl, $C_3$-$C_{10}$ cycloalkenyl, $C_1$-$C_6$ haloalkyl, $C_2$-$C_6$ haloalkenyl, $C_1$-$C_6$ alkoxy, $C_1$-$C_6$ haloalkoxy, $C_2$-$C_6$ alkenyloxy, $C_2$-$C_6$ alkynyloxy, $C_3$-$C_{10}$ cycloalkyloxy, $C_3$-$C_{10}$ cycloalkenyloxy, $C_2$-$C_6$ haloalkenyloxy, $C_6$-$C_{10}$ aryl or $C_6$-$C_{10}$ aryl substituted by from 1 to 3 groups independently selected from halogen, nitro, cyano, $C_1$-$C_3$ alkyl, $C_1$-$C_3$ alkoxy, $C_1$-$C_3$ haloalkyl, and $C_1$-$C_3$haloalkoxy; $C_3$-$C_{10}$ heterocyclyl or $C_3$-$C_{10}$ heterocyclyl substituted by from 1 to 3 groups independently selected from halogen, nitro, cyano, $C_1$-$C_3$ alkyl, $C_1$-$C_3$ alkoxy, $C_1$-$C_3$haloalkyl, and $C_1$-$C_3$ haloalkoxy; or $NR^6R^7$;
or $R^3$ and $R^5$ together with $X_2$ and the atoms to which they are attached, form a saturated or partially unsaturated 5-9 membered ring system optionally comprising 1 to 3 heteroatoms independently selected from S, O and N and optionally substituted with 1 to 3 groups independently selected from halogen or $C_1$-$C_6$ alkyl;
or $R^3$ and $R^8$ together with the atoms to which they are attached form a saturated or partially unsaturated 5-9 membered ring system optionally comprising 1 to 3 heteroatoms independently selected from S, O and N and optionally substituted with 1 to 3 groups independently selected from halogen or $C_1$-$C_6$ alkyl;
or $R^4$ and $R^5$ together with $X_2$ and the atoms to which they are attached, form a saturated or partially unsaturated 5-9 membered ring system optionally comprising 1 to 3 heteroatoms independently selected from S, O and N and optionally substituted with 1 to 3 groups independently selected from halogen or $C_1$-$C_6$ alkyl;
$R^6$ and $R^7$ are each independently hydrogen, $C_1$-$C_6$ alkyl, $C_1$-$C_6$ haloalkyl, $C_2$-$C_6$ alkenyl, or $C_2$-$C_6$ alkynyl, or $R^6$ and $R^7$ together with the nitrogen atom to which they are attached form a saturated or partially unsaturated 3-6 membered ring optionally comprising 1 to 3 heteroatoms independently selected from S, O and N and optionally substituted with 1 to 3 groups independently selected from halogen or $C_1$-$C_6$ alkyl;
$R^8$ is hydrogen, cyano, $C_1$-$C_6$ alkyl, $C_1$-$C_6$ haloalkyl, $C_2$-$C_6$ alkenyl, or $C_2$-$C_6$ alkynyl; $C_1$-$C_6$ alkoxy, $C_1$-$C_6$ haloalkoxy, $C_2$-$C_6$ alkenyloxy, $C_2$-$C_6$ alkynyloxy, $C_3$-$C_{10}$ cycloalkyloxy, $C_3$-$C_{10}$ cycloalkenyloxy, $C_2$-$C_6$ haloalkenyloxy;
or $R^7$ and $R^8$ together with the carbon atoms to which they are attached form a saturated or partially unsaturated 3-9 membered ring optionally comprising 1 to 3 heteroatoms independently selected from S, O and N and optionally substituted with 1 to 3 groups independently selected from halogen or $C_1$-$C_6$ alkyl, as a herbicide.

Compounds of formula (I) may exist as different geometric isomers, or in different tautomeric forms. This invention covers the use of all such isomers and tautomers, and mixtures thereof in all proportions, as well as isotopic forms such as deuterated compounds.

It may be the case that compounds of formula (I) may contain one or more asymmetric centers and may thus give rise to optical isomers and diastereomers. While shown without respect to stereochemistry, the present invention includes the use of all such optical isomers and diastereomers as well as the racemic and resolved, enantiomerically pure R and S stereoisomers and other mixtures of the R and S stereoisomers and agrochemically acceptable salts thereof.

Each alkyl moiety either alone or as part of a larger group (such as alkoxy, alkylthio, alkoxycarbonyl, alkylcarbonyl, alkylaminocarbonyl, or dialkylaminocarbonyl, et al.) may be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups are generally $C_1$-$C_6$ alkyl groups (except where already defined more narrowly), but are preferably $C_1$-$C_4$ alkyl or $C_1$-$C_3$ alkyl groups, and, more preferably, are $C_1$-$C_2$ alkyl groups (such as methyl).

Alkenyl and alkynyl moieties can be in the form of straight or branched chains, and the alkenyl moieties, where appropriate, can be of either the (E)- or (Z)-configuration. Alkenyl and alkynyl moieties can contain one or more double and/or triple bonds in any combination; but preferably contain only one double bond (for alkenyl) or only one triple bond (for alkynyl).

The alkenyl or alkynyl moieties are typically $C_2$-$C_4$ alkenyl or $C_2$-$C_4$ alkynyl, more specifically ethenyl (vinyl), prop-2-enyl (allyl), ethynyl, prop-2-ynyl (propargyl), or prop-1-ynyl.

Preferably, the term cycloalkyl refers to cyclopropyl, cyclobutyl, cyclopentyl or cyclohexyl.

In the context of the present specification the term "aryl" preferably means phenyl.

Heterocyclyl groups and heterocyclic rings (either alone or as part of a larger group, such as heterocyclyl-alkyl-) are ring systems containing at least one heteroatom and can be in mono- or bi-cyclic form. Preferably, heterocyclyl groups will contain up to two heteroatoms which will preferably be chosen from nitrogen, oxygen and sulfur. Examples of heterocyclic groups include oxetanyl, thietanyl, azetidinyl and 7-oxa-bicyclo[2.2.1]hept-2-yl. Heterocyclyl groups containing a single oxygen atom as heteroatom are most preferred. The heterocyclyl groups are preferably 3- to 8-membered, more preferably 3- to 6-membered rings.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents may be present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$ alkyl-S-(alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$ alkyl-S(O)-(alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$ alkyl-S(O)$_2$-(alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Compounds of formula (I) may form, and/or be used as, agronomically acceptable salts with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used in salt formation, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

Compounds of formula (I) may also form (and/or be used as) agronomically acceptable salts with various organic and/or inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids, when the compound of formula (I) contains a basic moiety.

Compounds of formula (I) may also be in the form of/used as hydrates which may be formed during the salt formation.

Preferred values of $X_1$, $X_2$, $R^1$, $R^2$, $R^3$, $R^4$, $R^5$, $R^6$, $R^7$, $R^8$, and n, are as set out below, and a compound of formula (I) according to the invention may comprise any combination of said values. The skilled person will appreciate that values for any specified set of embodiments may combined with values for any other set of embodiments where such combinations are not mutually exclusive.

Preferably $R^1$ is hydrogen, halogen, formyl, cyano, $C_1$-$C_6$ alkoxy, $C_1$-$C_6$ alkylsulfonyl, $C_1$-$C_6$ alkylthio, $C_1$-$C_6$ haloalkoxy, —C(O)NR$^6$R$^7$, NR$^6$R$^7$, or $C_1$-$C_6$ haloalkyl. More preferably $R^1$ is hydrogen, fluorine, chlorine, cyano, trifluoromethyl, methoxy, difluoromethoxy, formyl, methanesulfonyl, carboxamide, methanethiol or amino.

Preferably $R^2$ is halogen, cyano, nitro, $C_1$-$C_6$ alkyl, $C_1$-$C_6$ haloalkyl, $C_2$-$C_6$ alkenyl, $C_1$-$C_6$ alkylsulfinyl, $C_1$-$C_6$ alkylsulfonyl, $C_1$-$C_6$ alkylthio, —C(O)OR$^6$, $C_1$-$C_6$ alkoxy, $C_1$-$C_6$ haloalkoxy, $C_3$-$C_6$ cycloalkyl, or $C_2$-$C_6$ alkynyl. More preferably $R^2$ is halogen, cyano, $C_1$-$C_6$ alkyl, $C_1$-$C_6$ haloalkyl, $C_2$-$C_6$ alkenyl, $C_1$-$C_6$ alkoxy, $C_1$-$C_6$ haloalkoxy, $C_3$-$C_6$ cycloalkyl, —C(O)OR$^6$, or $C_2$-$C_6$ alkynyl. Even more preferably $R^2$ is methyl, trifluoromethyl, chloro, bromo, iodo, fluoro, vinyl, acetylenyl, methoxycarbonyl, —CO$_2$H, or cyclopropyl;

Preferably $R^3$ is $C_1$-$C_6$ alkyl, $C_2$-$C_6$ alkenyl, $C_2$-$C_6$ alkynyl, $C_2$-$C_6$ haloalkenyl, $C_1$-$C_6$ alkoxy, $C_1$-$C_6$ haloalkyl, $C_1$-$C_6$ haloalkoxy, $C_2$-$C_6$ alkenyloxy, $C_3$-$C_{10}$ cycloalkyl, or NR$^6$R$^7$. More preferably $R^3$ is hydrogen, or $C_1$-$C_3$ alkyl. Even more preferably $R^3$ is methyl or ethyl.

Preferably $R^4$ is O.

Preferably $X_2$ is O, or NR$^8$.

Preferably $R^5$ is $C_1$-$C_6$ alkyl, $C_2$-$C_6$ alkenyl, $C_2$-$C_6$ alkynyl, $C_3$-$C_{10}$ cycloalkyl, $C_1$-$C_6$ haloalkyl, $C_2$-$C_6$ haloalkenyl, $C_1$-$C_6$ alkoxy, $C_1$-$C_6$ haloalkoxy, $C_2$-$C_6$ alkenyloxy, $C_2$-$C_6$ alkynyloxy, $C_3$-$C_{10}$ cycloalkyloxy, $C_3$-$C_{10}$ cycloalkenyloxy, $C_2$-$C_6$ haloalkenyloxy, $C_6$-$C_{10}$ aryl, $C_6$-$C_{10}$ aryl substituted by 1-3 groups independently selected from halogen, nitro, cyano, $C_1$-$C_3$ alkyl, $C_1$-$C_3$ alkoxy, $C_1$-$C_3$ haloalkyl, and $C_1$-$C_3$ haloalkoxy, $C_3$-$C_{10}$ heterocyclyl, or NR$^6$R$^7$. In one set of embodiments $R^5$ is preferably methyl, ethyl, iso-propyl, tert-butyl, or tert-butoxy. In a further set of embodiments, $R^5$ is preferably phenyl optionally substituted by 1-3 groups halogen, nitro, cyano, $C_1$-$C_3$ alkyl, $C_1$-$C_3$ alkoxy, $C_1$-$C_3$ haloalkyl, and $C_1$-$C_3$ haloalkoxy, more preferably phenyl substituted once by halogen, nitro, cyano, $C_1$-$C_3$ alkyl, $C_1$-$C_3$ alkoxy, $C_1$-$C_3$ haloalkyl, or $C_1$-$C_3$ haloalkoxy, In a further set of embodiments $R^5$ is preferably $C_2$-$C_6$ alkynyl. Compounds of formula (I) where $R^5$ is $C_2$-$C_6$ alkynyl are novel and thus form a further aspect of the invention.

Preferably $R^8$ is hydrogen, cyano, $C_1$-$C_6$ alkyl, $C_1$-$C_6$ haloalkyl, $C_2$-$C_6$ alkenyl, or $C_2$-$C_6$ alkynyl. More preferably $R^8$ is hydrogen or methyl. In one set of embodiment $R^8$ is hydrogen. In a further set of embodiments $R^8$ is methyl.

In embodiments where $R^3$ and $R^5$ together with $X_2$ and the atoms to which they are attached, form a saturated or partially unsaturated 5-9 membered ring system optionally comprising 1 to 3 heteroatoms independently selected from S, O and N and optionally substituted with 1 to 3 groups independently selected from halogen or $C_1$-$C_6$ alkyl, it is preferred that the following groups Q, are formed:

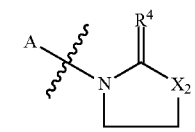

$Q_1$

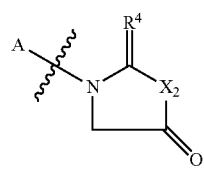

$Q_2$ wherein $X^2$ and $R^4$ are as defined herein, and A denotes the point of attachment to the pyridino/pyrimidino-thiazole moiety. Preferably in each of groups $Q_1$ and $Q_2$, $R^4$ is O and $X_2$ is O or $NR^8$. Even more preferably, $R^4$ is O and $X_2$ is O or $NR^8$ and $R^8$ is methyl.

Tables 1 and 2 below provide 91 specific examples of herbicidal compounds of formula (I) for use according to the invention.

TABLE 1-continued

Specific examples of compounds of formula (I)

| Compound | Structure |
|---|---|
| A10 | 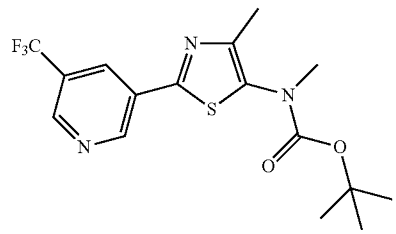 [SMILES: Cc1nc(-c2cncc(C(F)(F)F)c2)sc1N(C)C(=O)OC(C)(C)C] |
| A11 | 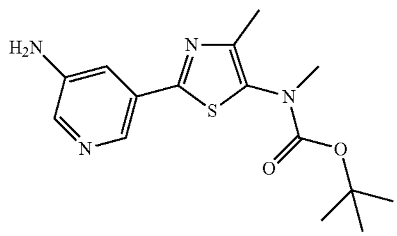 [SMILES: Cc1nc(-c2cncc(N)c2)sc1N(C)C(=O)OC(C)(C)C] |
| A12 | 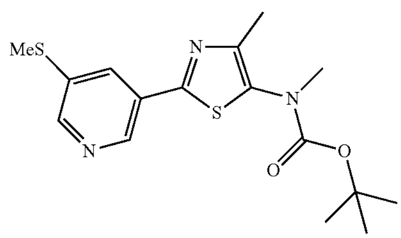 [SMILES: CSc1cncc(-c2nc(C)c(N(C)C(=O)OC(C)(C)C)s2)c1] |
| A13 | 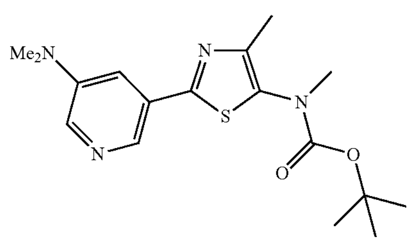 [SMILES: Cc1nc(-c2cncc(N(C)C)c2)sc1N(C)C(=O)OC(C)(C)C] |
| A14 | 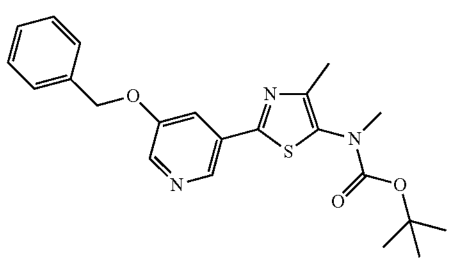 [SMILES: Cc1nc(-c2cncc(OCc3ccccc3)c2)sc1N(C)C(=O)OC(C)(C)C] |
| A15 | 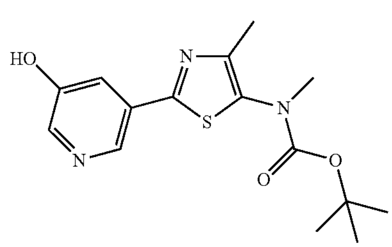 [SMILES: Cc1nc(-c2cncc(O)c2)sc1N(C)C(=O)OC(C)(C)C] |
| A16 | |
| A17 | |
| A18 | |
| A19 | |
| A20 | |
| A21 | |

TABLE 1-continued
Specific examples of compounds of formula (I)
| Compound | Structure |
|---|---|
| A22 | 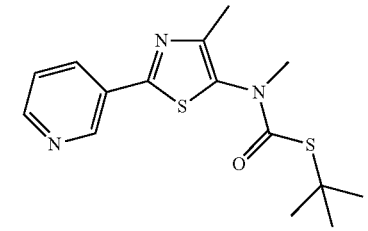 |
| A23 | 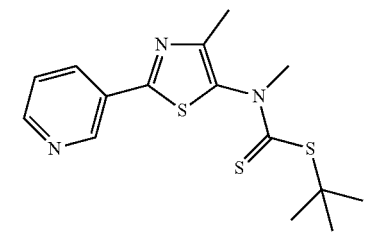 [SMILES: Cc1nc(-c2cccnc2)sc1N(C)C(=S)SC(C)(C)C] |
| A24 | 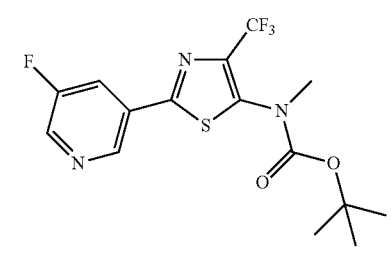 [SMILES: CN(C(=O)OC(C)(C)C)c1sc(-c2cncc(F)c2)nc1C(F)(F)F] |
| A25 | 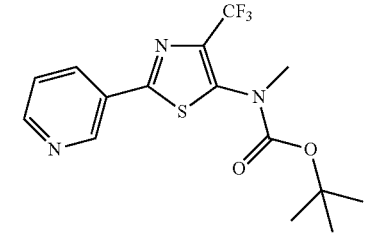 [SMILES: CN(C(=O)OC(C)(C)C)c1sc(-c2cccnc2)nc1C(F)(F)F] |
| A26 | 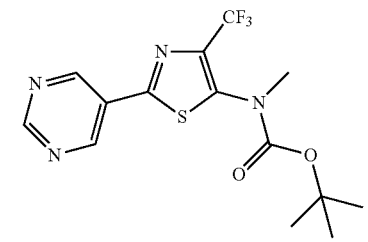 [SMILES: CN(C(=O)OC(C)(C)C)c1sc(-c2cncnc2)nc1C(F)(F)F] |
| A27 | 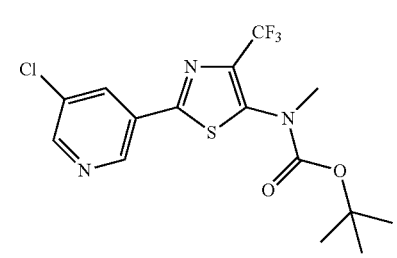 [SMILES: CN(C(=O)OC(C)(C)C)c1sc(-c2cncc(Cl)c2)nc1C(F)(F)F] |
| A28 | 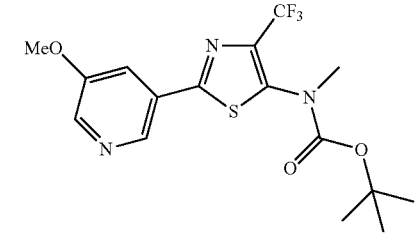 [SMILES: COc1cncc(-c2nc(C(F)(F)F)c(N(C)C(=O)OC(C)(C)C)s2)c1] |
| A29 | 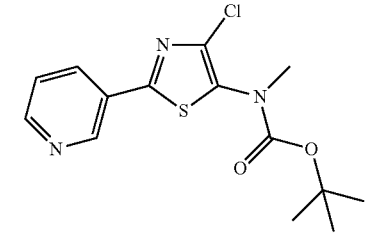 [SMILES: CN(C(=O)OC(C)(C)C)c1sc(-c2cccnc2)nc1F] |
| A30 | 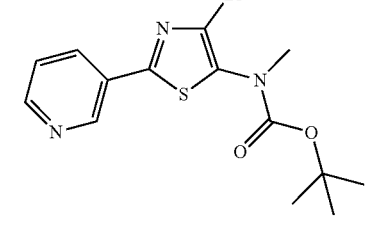 |
| A31 | 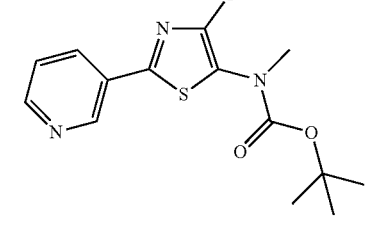 |
| A32 | 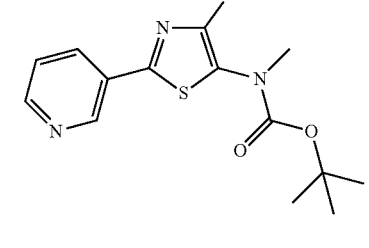 |
| A33 | 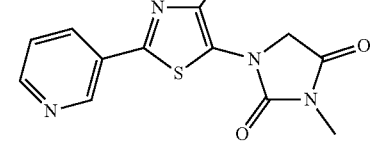 |

TABLE 1-continued

Specific examples of compounds of formula (I)

| Compound | Structure |
|---|---|
| A34 | (structure) |
| A35 | (structure) |
| A38 | (structure) |
| A39 | (structure) |
| A40 | (structure) |
| A41 | (structure) |
| A43 | (structure) |
| A44 | (structure) |
| A45 | (structure) |
| A46 | (structure) |
| A47 | (structure) |
| A48 | (structure) |
| A49 | (structure) |

TABLE 1-continued

Specific examples of compounds of formula (I)

| Compound | Structure |
|---|---|
| A50 | 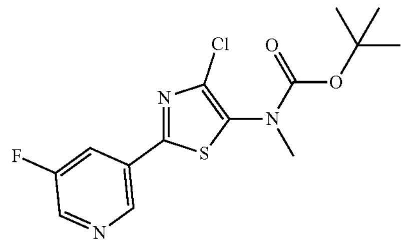 |
| A51 | 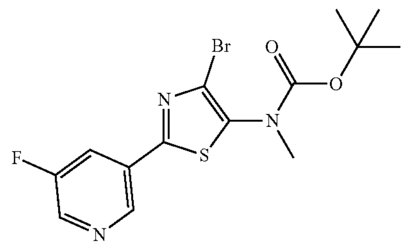 [SMILES: CN(C(=O)OC(C)(C)C)c1sc(-c2cncc(F)c2)nc1Br] |
| A52 | 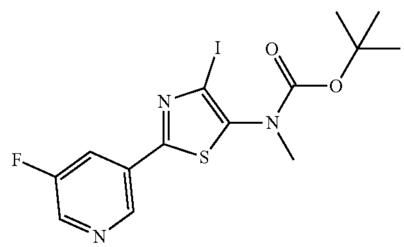 [SMILES: CN(C(=O)OC(C)(C)C)c1sc(-c2cncc(F)c2)nc1I] |
| A53 | 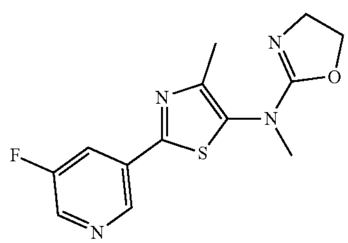 [SMILES: Cc1nc(-c2cncc(F)c2)sc1N(C)C1=NCCO1] |
| A54 | 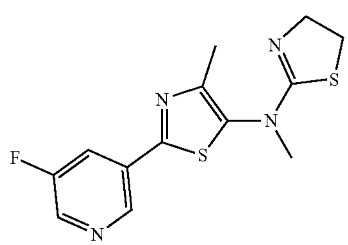 [SMILES: Cc1nc(-c2cncc(F)c2)sc1N(C)C1=NCCS1] |
| A55 | 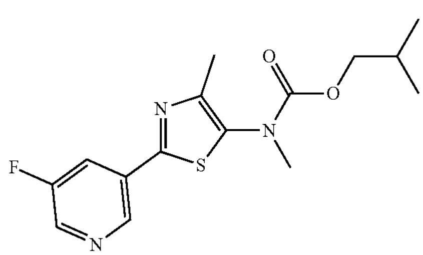 [SMILES: Cc1nc(-c2cncc(F)c2)sc1N(C)C(=O)OCC(C)C] |
| A56 | 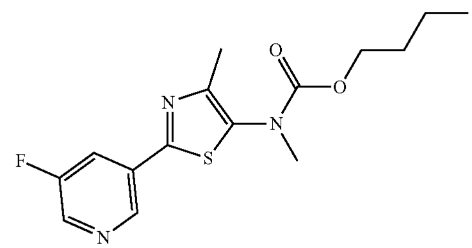 [SMILES: CCCCOC(=O)N(C)c1sc(-c2cncc(F)c2)nc1C] |
| A57 | 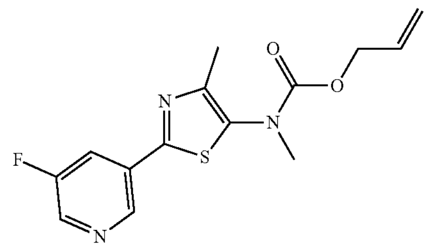 [SMILES: C=CCOC(=O)N(C)c1sc(-c2cncc(F)c2)nc1C] |
| A58 | 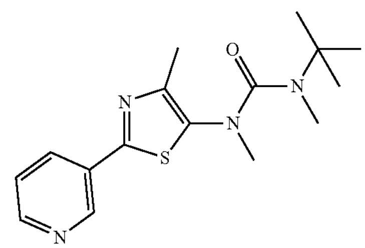 [SMILES: Cc1nc(-c2cccnc2)sc1N(C)C(=O)N(C)C(C)(C)C] |
| A59 | 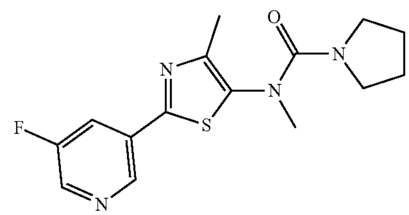 [SMILES: Cc1nc(-c2cncc(F)c2)sc1N(C)C(=O)N1CCCC1] |
| A60 | 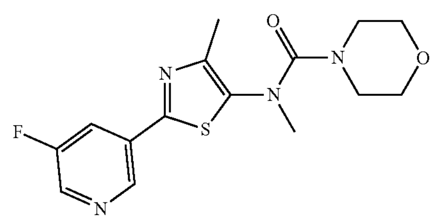 [SMILES: Cc1nc(-c2cncc(F)c2)sc1N(C)C(=O)N1CCOCC1] |
| A61 | 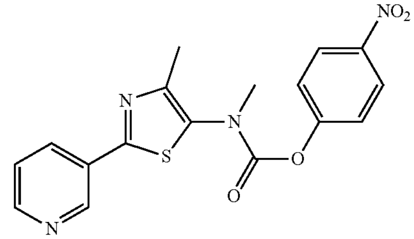 [SMILES: Cc1nc(-c2cccnc2)sc1N(C)C(=O)Oc1ccc([N+](=O)[O-])cc1] |

TABLE 1-continued

Specific examples of compounds of formula (I)

| Compound | Structure |
|---|---|
| A62 | (5-fluoropyridin-3-yl N-oxide)-thiazole (4-methyl) with N-methyl tert-butyl carbamate |
| A63 | (5-fluoropyridin-3-yl N-oxide)-thiazole (4-CF$_3$) with N-methyl tert-butyl carbamate |

As stated hereinbefore, compounds of formula (I) wherein R$^5$ is C$_2$-C$_6$ alkynyl are novel. Accordingly, the invention also provided compounds of formula (I)-(i), which are compounds of formula (I) as defined herein, wherein R$^5$ is C$_2$-C$_6$ alkynyl. In compounds of formula (I)-(i) the preferred substituents for X$_1$, X$_2$, R$^1$, R$^2$, R$^3$, R$^4$, R$^6$, R$^7$, R$^8$ and n are as defined hereinbefore, with respect to compounds of formula (I)

However, particularly preferred embodiments will have the substituent preferences described below.

Where X$_1$ is CR$^1$, R$^1$ is preferably halogen, more preferably fluoro. R$^2$ is preferably methyl, trifluoromethyl, chloro, bromo, iodo, fluoro, vinyl, acetylenyl, methoxycarbonyl, —CO$_2$H, or cyclopropyl, more preferably methyl. R$^3$ is preferably hydrogen or C$_1$-C$_3$ alkyl, more preferably methyl or ethyl, most preferably methyl. R$^4$ is preferably oxygen. X$_2$ is preferably oxygen or NR$^8$, wherein R$^8$ is preferably hydrogen. R$^5$ is preferably C$_3$-C$_5$ alkynyl.

In one particularly preferred set of embodiments, R$^5$ is selected from the group consisting of 1-methyl-prop-2-ynyl, 1,1-dimethylprop-2-ynyl, and prop-2-ynyl. Table 2 below provides 28 specific examples of compounds of formula (I)-(i) according to the invention.

TABLE 2

Specific examples of compounds of formula (I)-(i)

| Compound | Structure |
|---|---|
| B1 | pyridin-3-yl-thiazole(4-methyl) with N-methyl prop-2-ynyl carbamate |
| B2 | pyridin-3-yl-thiazole(4-methyl) with N-methyl but-3-yn-2-yl carbamate |
| B3 | pyridin-3-yl-thiazole(4-methyl) with N-methyl 2-methylbut-3-yn-2-yl carbamate |
| B4 | pyridin-3-yl-thiazole(4-methyl) with N-methyl but-2-ynyl carbamate |
| B5 | pyridin-3-yl-thiazole(4-methyl) with N-methyl N'-prop-2-ynyl urea |
| B6 | pyridin-3-yl-thiazole(4-methyl) with N-methyl N'-(but-3-yn-2-yl) urea |
| B7 | pyridin-3-yl-thiazole(4-methyl) with N-methyl N'-(2-methylbut-3-yn-2-yl) urea |

TABLE 2-continued

Specific examples of compounds of formula (I)-(i)

| Compound | Structure |
| --- | --- |
| B8 | [structure] |
| B9 | [structure] |
| B10 | [structure] |
| B11 | [structure] |
| B12 | [structure] |
| B13 | [structure] |
| B14 | [structure] |
| B15 | [structure] |
| B16 | [structure] |
| B17 | [structure] |
| B18 | [structure] |
| B19 | [structure] |

TABLE 2-continued

Specific examples of compounds of formula (I)-(i)

| Compound | Structure |
|---|---|
| B20 | *(structure)* |
| B21 | *(structure)* |
| B22 | *(structure)* |
| B23 | *(structure)* |
| B24 | *(structure)* |
| B25 | *(structure)* |
| B26 | *(structure)* |
| B27 | *(structure)* |
| B28 | *(structure)* |

Compounds of formula (I) may be prepared according to the following schemes, in which the substituents $X_1$, $X_2$, $R^1$, $R^2$, $R^3$, $R^4$, $R^5$, $R^6$, $R^7$, $R^8$, and n, have (unless otherwise stated explicitly) the definitions described hereinbefore, using techniques known to the person skilled in the art of organic chemistry. General methods for the production of compounds of formula (I) are described below. Unless otherwise stated in the text the synthetic procedures are derived from WO2013/186089 or W2010/129497. The starting materials used for the preparation of the compounds of the invention may be purchased from the usual commercial suppliers or may be prepared by known methods. The starting materials as well as the intermediates may be purified before use in the next step by state of the art methodologies such as chromatography, crystallization, distillation and filtration.

Typical abbreviations used throughout are as follows:
Ac=acetyl
Bn=benzyl
Bu=butyl
t-BuOH=tert-butanol
DMAP=4-dimethylaminopyridine
DMF=N, N-dimethylformamide
DMSO=dimethylsulfoxide
DPPA=diphenylphosphoryl azide
$Et_3N$=triethylamine
$Et_2O$=diethyl ether
EtOAc=ethyl acetate
EtOH=ethanol
mCPBA=meta-chloro-benzoic acid
Me=methyl MeI=methyl iodide
MeCN=acetonitrile
NBS=N-bromosuccinimide
N-Boc=N-tert-butoxycarbonyl
NIS=N-iodosuccinimide
Ph=phenyl
TFA=trifluoroacetic acid
THF=tetrahydrofuran

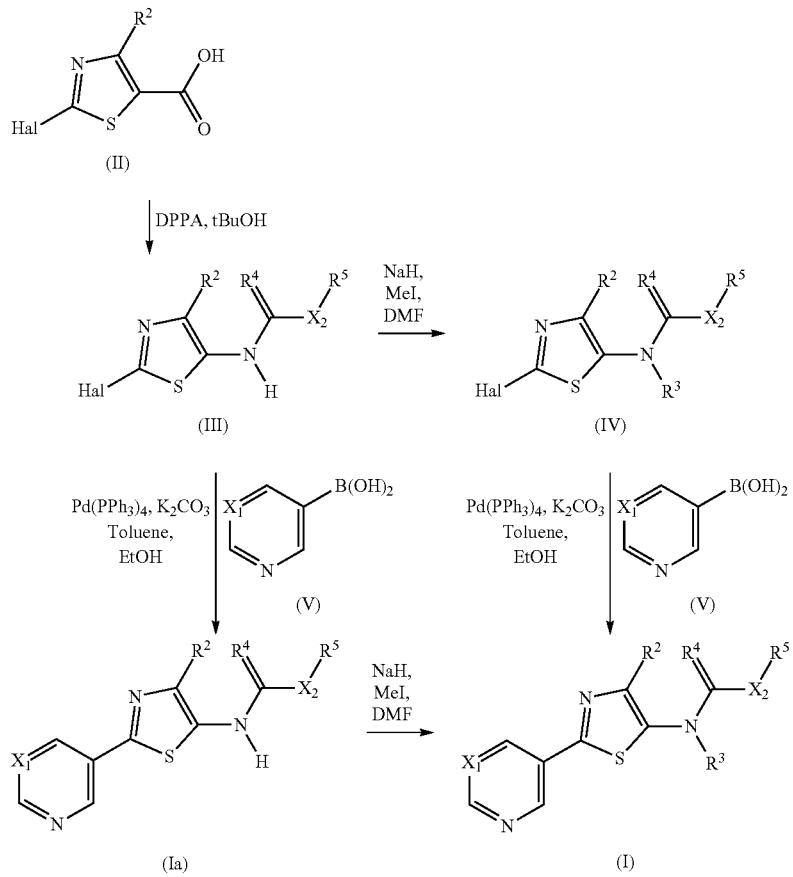

Reaction Scheme 1

As shown in Reaction Scheme 1, compounds of formula (I) can be prepared via a three step sequence wherein a suitably substituted 2-bromo-thiazole-5-carboxylic acid (11) can be reacted to form an acyl azide with suitable reagents such as diphenylphosphoryl azide (DPPA) which can be further converted in-situ with a suitable alcohol, such as t-butanol (t-BuOH) to give the carbamates of formula (III). This can be further substituted with alkylating agents such as MeI under basic conditions (for example using NaH) in a polar solvent (such as DMF) to give compounds of formula (IV). These compounds can be converted to products of formula (I) using palladium catalysed cross-coupling between a suitable boronic acid derivative of formula (V) with a palladium catalyst such as Pd(PPh$_3$)$_4$, a base such as potassium carbonate and a solvent which may be a mixed solvent system such as ethanol, toluene and water.

Alternatively (as also shown in reaction scheme 1) compounds of formula (I) can be prepared via variation of the three step sequence wherein a suitably substituted 2-bromo-thiazole-5-carboxylic acid (11) can be reacted to form an acyl azide with suitable reagents such as diphenylphosohoryl azide (DPPA) which can be further converted in-situ with a suitable alcohol, such as t-Butanol (t-BuOH) to give the carbamates of formula (III).

These compounds can be converted to products of formula (Ia) using palladium catalysed cross-coupling between a suitable boronic acid derivative of formula (V) with a palladium catalyst such as Pd(PPh$_3$)$_4$, a base such as potassium carbonate and a solvent which may be a mixed solvent system such as ethanol, toluene and water. These materials can be further reacted with alkylating agents such as MeI under basic conditions (for example using NaH) with a polar solvent (such as DMF) to give compounds of formula (I).

Compounds of formula (I) may also be prepared via condensation of an appropriately substituted thioamide (VI) in the presence of an appropriately substituted 2-halo β-keto ester (VII), for example where R$^2$=alkyl or trifluoroalkyl, to give compounds of formula (VIII) which can be further elaborated via basic saponification, for example with NaOH, water and ethanol mixtures. The resulting carboxylic acid (IX) can be reacted to form an acyl azide with suitable reagents such as diphenylphosphoryl azide (DPPA), which can be further converted in-situ with a suitable alcohol, such as t-butanol (t-BuOH), to give the carbamates of formula (Ia). These materials can be further reacted with alkylating agents such as MeI under basic conditions, for example using K$_2$CO$_3$ in a polar solvent (such as MeCN), to give compounds of formula (I) (Reaction Scheme 2).

Reaction Scheme 2
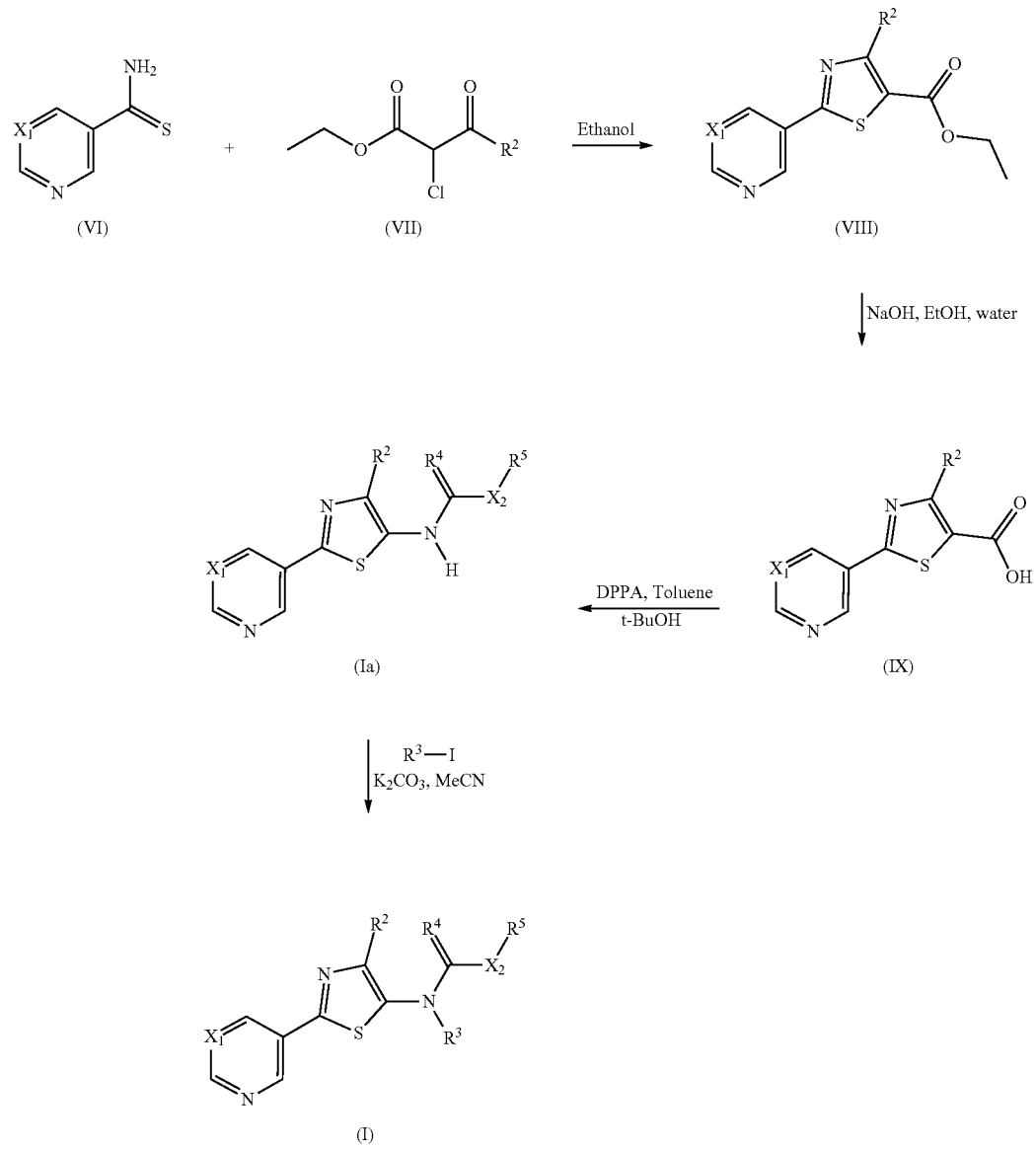
Reaction Scheme 3
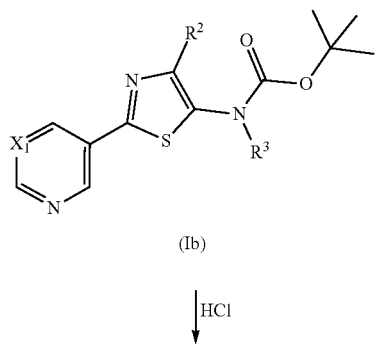

-continued
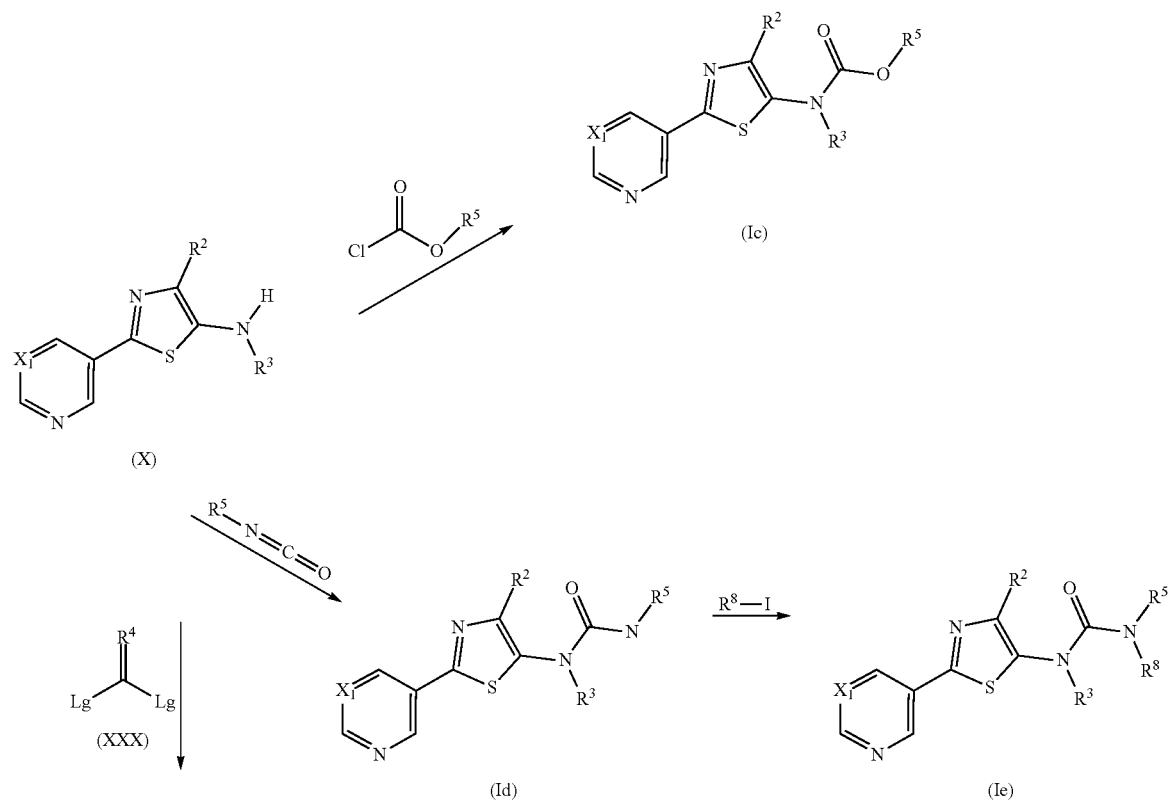
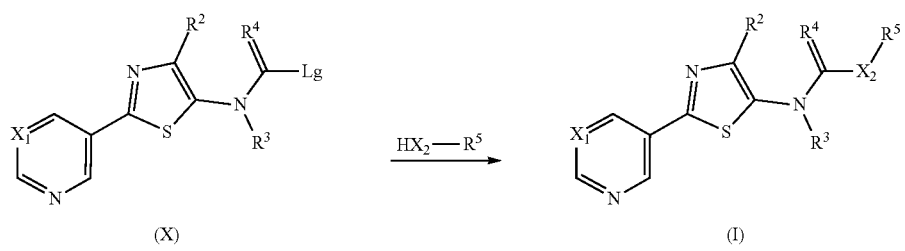

As shown in Reaction Scheme 3, when $R^4$ is O, $X_2$ is O and $R^5$ is t-Bu, the resulting N-Boc group may be removed under mild acidic conditions, such as with HCl in ether, to afford an amine salt, such as the HCl salt. Compounds of formula (X) may then be further converted to compounds such as (Ic) by reaction with a suitable chloroformate (such as ethyl chloroformate) and a base such as pyridine.

Alternatively, compounds of formula (X) may then be further converted to compounds such as (Id) by reaction with a suitable isocyanate (such as t-butyl-isocyanate). Compounds of formula (Id) may be further alkylated with a suitable electrophile and base combination (for example MeI, $K_2CO_3$) to give compounds of the type where $X_2=NR^8$ (Ie).

As a further alternative, compounds of formula (X) may then be further converted to compounds of Formula (XI) by reaction with a compound of Formula (XXX), where Lg is a suitable leaving group (such as Cl); for example phosgene or a suitable phosgene equivalent (such as carbonyldiimidazole or 4-nitrophenyl chloroformate). This may be followed by reaction with an alcohol, amine or thiol to afford compounds of formula (I).

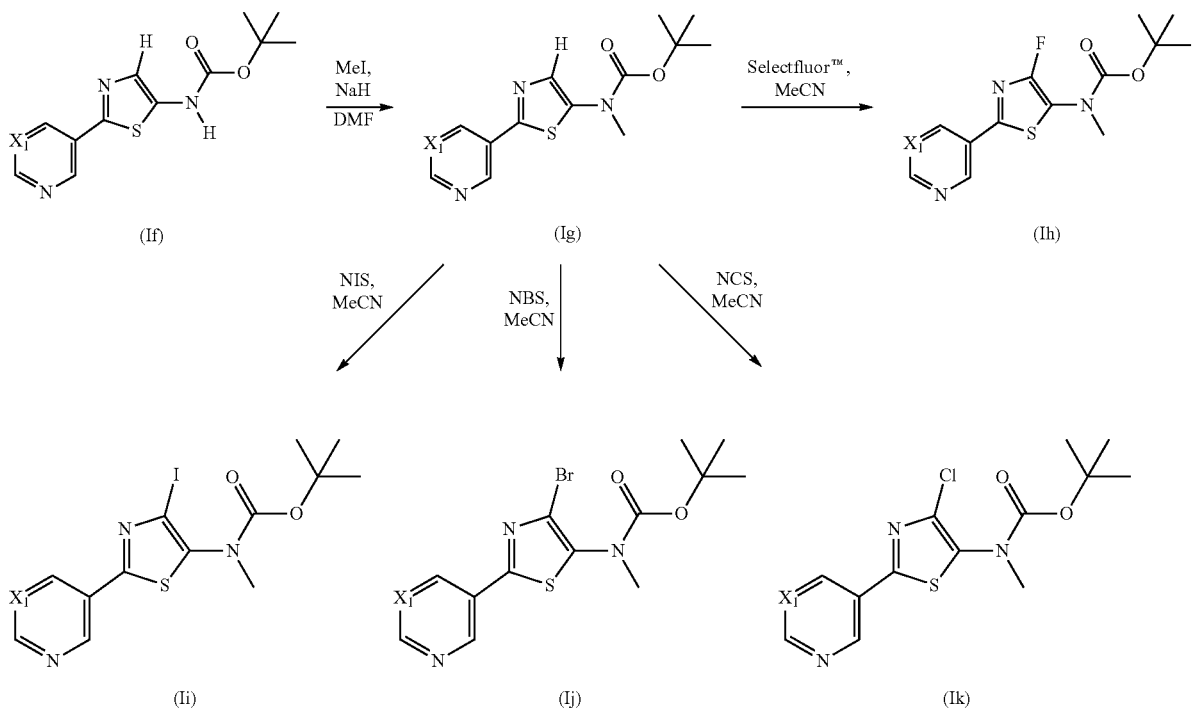

Reaction Scheme 4

In cases where $R^2$ is H, it is possible to convert compounds of Formula (If) into compounds of Formula (Ig) by alkylation of the nitrogen using a base, such as NaH, and an electrophile, such as MeI, in a polar solvent, such as DMF. It is then possible perform electrophilic substitution to introduce new $R^2$ substituents on compound (Ig). Electrophilic halogenation reagents can be used to perform this transformation. For example where $R^2$ is I, N-iodosuccinimide in a solvent such as acetonitrile are suitable conditions to give a compound of formula (Ii). Where $R^2$ is Br, N-bromosuccinimide in a solvent (e.g. acetonitrile) is suitable to give a compound of formula (Ij), and where $R^2$ is Cl, N-chlorosuccinimide in a solvent (e.g. acetonitrile) can be used to furnish a compound of formula (Ik). Where $R^2$ is F, Selectfluor™ (1-(chloromethyl)-4-fluoro-1,4-diazoniabicyclo[2.2.2]octane ditetrafluoroborate) in acetonitrile is a typical set of reaction conditions to perform the transformation to convert a compound of formula (Ig) into a compound of formula (Ih) (Reaction Scheme 4, above).

Compounds of formula (I) may also be prepared via condensation of an appropriately substituted thioamide (VI) in the presence of an appropriately substituted 2-halo ketone (XII) (e.g. chloroacetone) to give compounds of formula (XIII), which can be further elaborated via halogenation (for example with NBS) to afford the bromo-thiazole (XIV).

Reaction Scheme 5

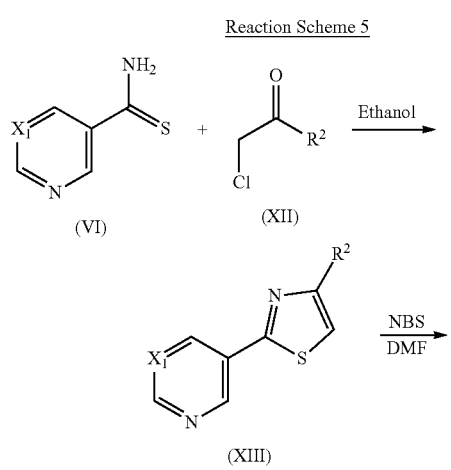

Reaction of compounds of this type with a nitrogen containing heterocycle, such as a hydantoin of formula (XV), in the presence of a copper catalyst (e.g. CuI) with a base (e.g. $K_2CO_3$) with a ligand (e.g. N,N'-dimethylethylenediamine (XVI)) in a suitable solvent (e.g. 1,4-dioxane) affords compounds of formula (Im). This is shown schematically in Reaction Scheme 5 (above), and typical methods for such a transformation are taught, for example, in WO2011/136292.

Compounds of formula (X) can be converted to a compound of formula (In) by treatment with a bifunctional reagent (XVII) (such as 1-chloro-2-isothiocyanoethane) in a solvent (such as dioxane) as taught in WO2013/186089 (Reaction Scheme 6).

Reaction Scheme 6

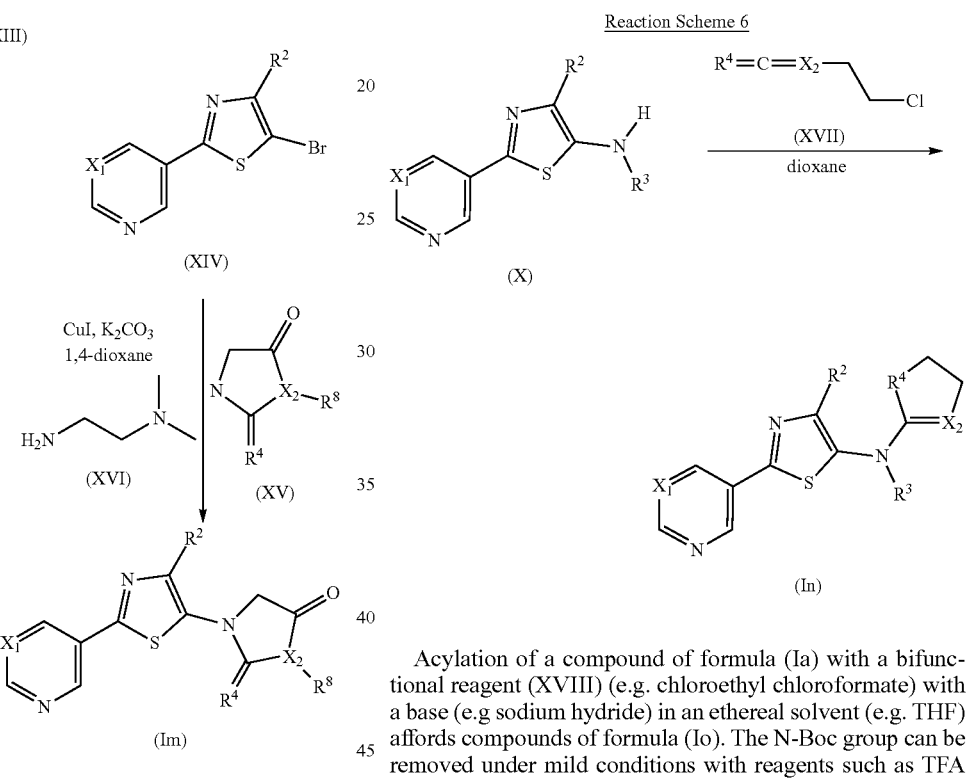

Acylation of a compound of formula (Ia) with a bifunctional reagent (XVIII) (e.g. chloroethyl chloroformate) with a base (e.g sodium hydride) in an ethereal solvent (e.g. THF) affords compounds of formula (Io). The N-Boc group can be removed under mild conditions with reagents such as TFA in $CH_2Cl_2$ to give (Ip).

Reaction Scheme 7

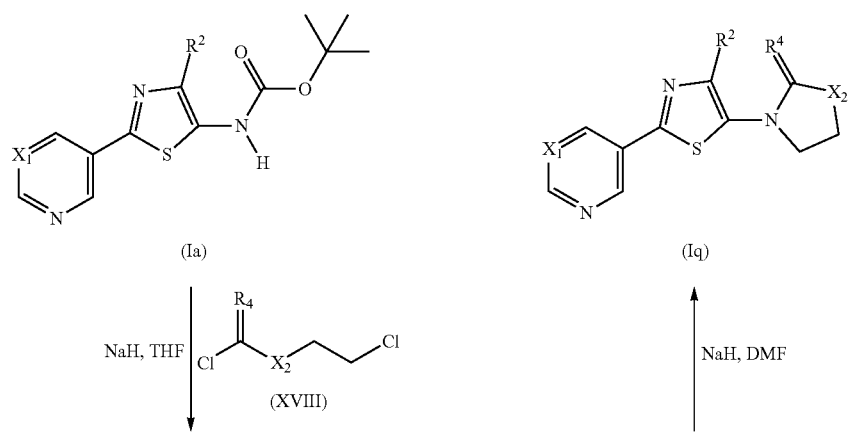

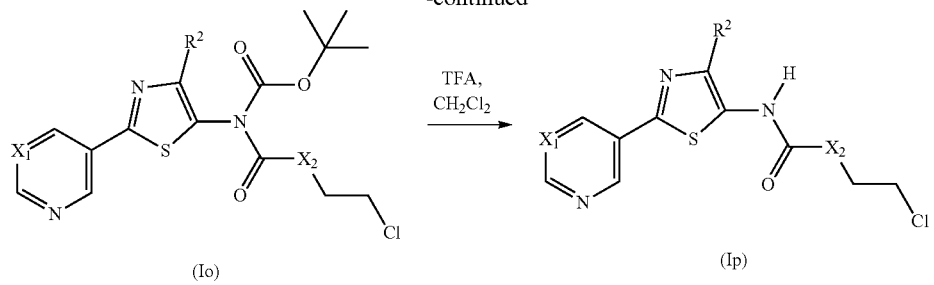

Further compounds of formula (Ip) can be cyclized by deprotonation with a suitable base (such as NaH) in a polar solvent (DMF is a suitable solvent for this step) to give compound of formula (Iq) (Reaction Scheme 7).

Iodinated compounds of formula (Ir) can themselves be useful building block to allow easy access to compounds of formulae (Is)-(Ix) (Reaction Scheme 8). Compound (Is) can be prepared by Iodine-Lithium exchange (using a reagent such as n-BuLi) followed by quenching with $CO_2$ in an ethereal solvent (such as THF).

Reaction Scheme 8

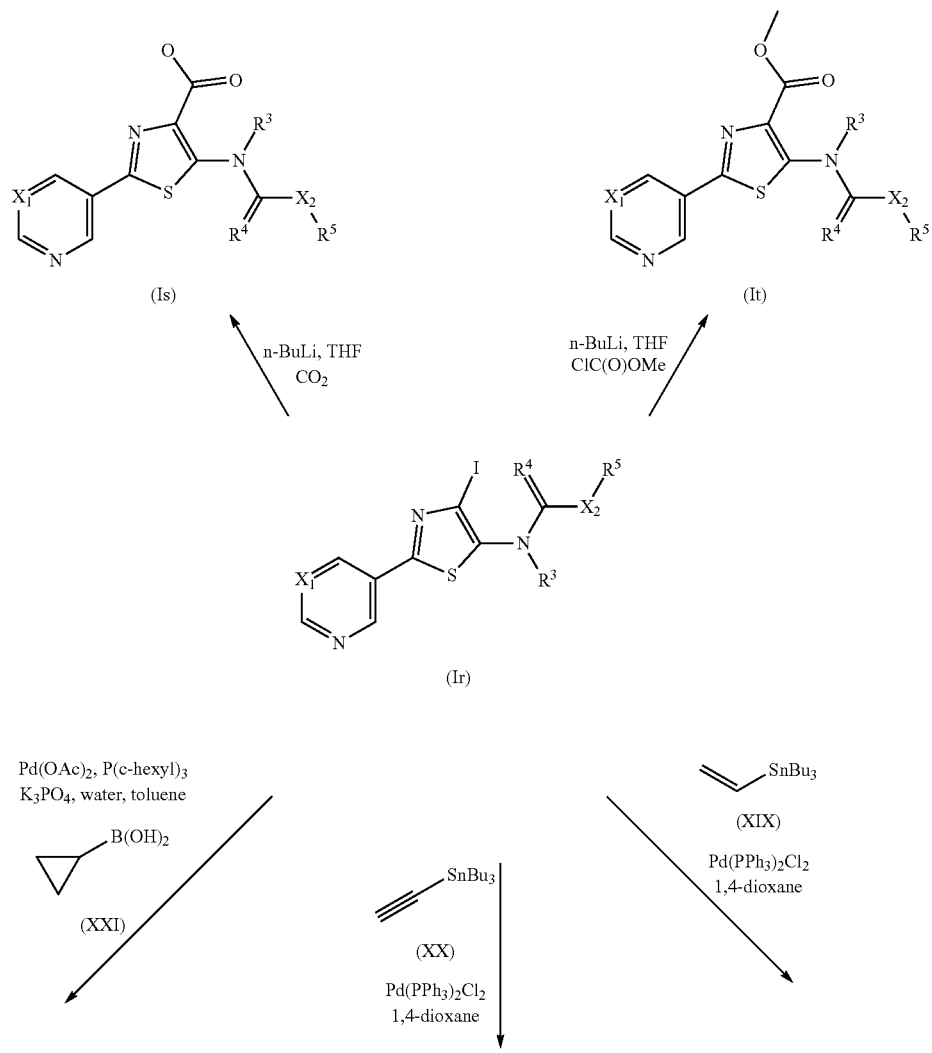

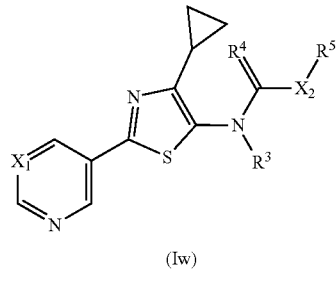 (Iw)

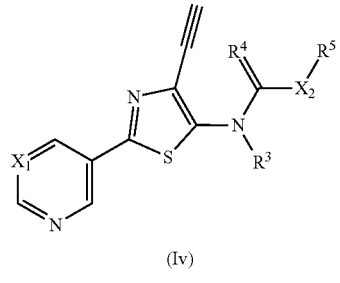 (Iv)

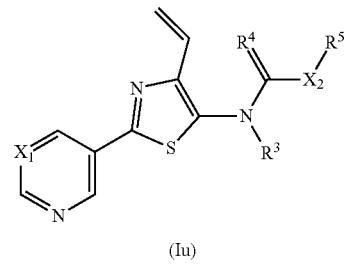 (Iu)

Compounds of Formula (It) can be prepared by Iodine-Lithium exchange (using a reagent such as n-BuLi) followed by quenching with a chloroformate (such as methyl chloroformate) in an ethereal solvent (such as THF).

Compounds of formula (Iu) can be made via a Stille cross-coupling with a Pd catalyst (such as Pd(PPh$_3$)$_2$Cl$_2$) in a suitable solvent (such as 1,4-dioxane) with a suitable stannane (such as (XIX)).

Compounds of formula (Iv) can be made via a Stille cross-coupling with a Pd catalyst (such as Pd(PPh$_3$)$_2$Cl$_2$) in a suitable solvent (such as 1,4-dioxane) with a suitable stannane (such as (XX)).

Compounds of formula (Iw) can be made via a Suzuki cross-coupling with a Pd pre-catalyst (such as Pd(OAc)$_2$), with a suitable ligand (such as P(c-hexyl)$_3$) and base (such as K$_3$PO$_4$) in a suitable solvent such as 1,4-dioxane with a suitable boronic acid (such as (XXI)).

Reaction of compounds of Formula (X) with carbon disulphide in a solvent such as ethanol and a base such as K$_2$CO$_3$, followed by addition of an electrophile such as an alkyl iodide gives compounds of formula (Iaa) (Reaction Scheme 9).

Reaction Scheme 9

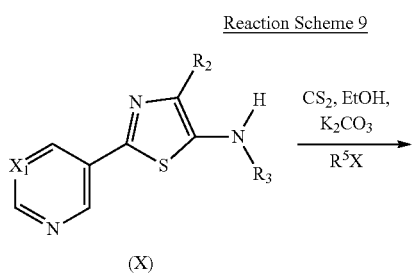
(X)

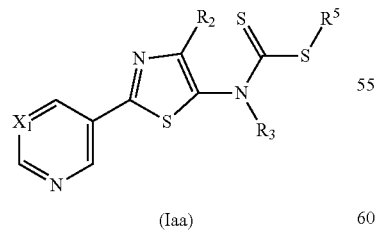
(Iaa)

Compounds of formula (Iab) where X$_2$ is O and R$^5$ is alkyl, haloalkyl, alkenyl, alkynyl, cycloalkyl, cycloalkenyl or haloalkenyl, can be made via in-situ generation of an isocyanate from a hydroxamic acid anhydride (XXV) (for example N-boc-O-tosyl hydroxylamine wherein R$^4$ is O, X$_2$ is O and R$^5$ is t-Bu) in the presence of a base (for example K$_2$CO$_3$) via a Lossen rearrangement (as taught by Thambidurai et al., Tetrahedron Letters, 2012, 53, 2292 and Tetrahedron Letters, 2014, 55, 2014) which will then react with the amino-heterocycle of formula (X) to form the substituted urea compound (Iab) (Reaction Scheme 10).

Reaction Scheme 10

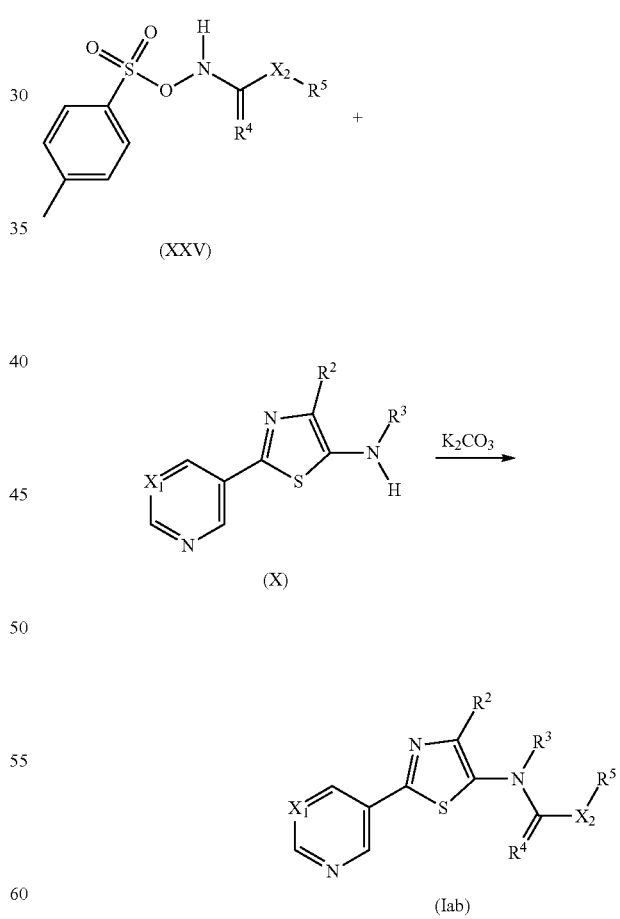

Further, N-oxides of formula (Iac) may be prepared by oxidation of (I) with an oxidising agent such as meta-chloroperbenzoic acid (mCPBA) or other suitable oxidants, in a suitable solvent (for example CH$_2$Cl$_2$) (Reaction Scheme 11).

Reaction Scheme 11

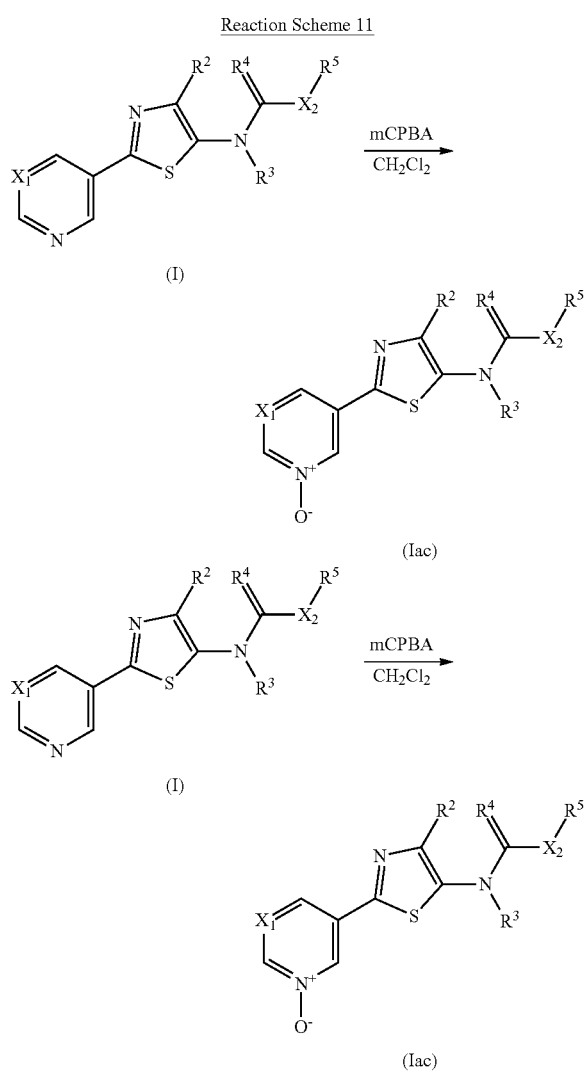

It can be seen from the general methods described above, as well as from the specific examples, that certain compounds of Formula (I) are not only useful as herbicides per se, but may also be used as intermediates in the production of further herbicidal compounds of formula (I). This is particularly the case for compounds of formula (I) wherein $R^3$ is hydrogen, and/or $R^2$ is iodo.

The compounds of Formula (I) as described herein may be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound as described herein and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

Such herbicidal compositions generally comprise from 0.1 to 99% by weight, especially from 0.1 to 95% by weight of compounds of Formula (I) and from 1 to 99.9% by weight of a formulation adjuvant, which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

Herbicidal compositions as described herein may further comprise at least one additional pesticide. For example, the compounds of formula (I) can also be used in combination with other herbicides or plant growth regulators. In a preferred embodiment the additional pesticide is a herbicide and/or herbicide safener. Examples of such mixtures are, in which 'I' represents a compound of Formula (I), I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of formula (I) and/or compositions of the present invention may also be combined with herbicidal compounds disclosed in WO06/024820 and/or WO07/096576.

The mixing partners of the compound of Formula (I) may also be in the form of esters or salts, as mentioned e.g. in The Pesticide Manual, Sixteenth Edition, British Crop Protection Council, 2012.

The compound of Formula (I) can also be used in mixtures with other agrochemicals such as fungicides, nematicides or insecticides, examples of which are given in The Pesticide Manual (supra).

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula (I) as described herein can also be used in combination with one or more safeners. Likewise, mixtures of a compound of Formula (I) as described herein with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxy-benzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino]benzenesulfonamide.

The safeners of the compound of Formula (I) may also be in the form of esters or salts, as mentioned e.g. in The Pesticide Manual (supra). The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula (I) to safener is from 100:1 to 1:10, especially from 20:1 to 1:1.

The mixtures can advantageously be used in the above-mentioned formulations (in which case "active ingredient" relates to the respective mixture of compound of Formula (I) with the safener).

As described above, compounds of formula (I) and/or compositions comprising such compounds may be used in methods of controlling unwanted plant growth, and in particular in controlling unwanted plant growth in crops of useful plants. Thus, the present invention further provides a method of selectively controlling weeds at a locus comprising crop plants and weeds, wherein the method comprises application to the locus, of a weed-controlling amount of a compound of formula (I), or a composition as described herein. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula (I) may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®, as well as those where the crop plant has been engineered to over-express homogentisate solanesyltransferase as taught in, for example, WO2010/029311.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds').

The weeds to be controlled include both monocotyledonous (e.g. grassy) species, for example: *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*; and dicotyledonous species, for example: *Abutilon, Amaranthus, Ambrosia, Chenopodium, Chrysanthemum, Conyza, Galium, Ipomoea, Kochia, Nasturtium, Polygonum, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

Preferably the weeds to be controlled and/or growth-inhibited, include monocotyledonous weeds, more preferably grassy monocotyledonous weeds, in particular those from the following genus: *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), *Juncus* (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*, and/or volunteer corn (volunteer maize) weeds; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria decumbens, Brachiaria plantaginea, Brachiaria platyphylla* (BRAPP), *Bromus tectorum, Digitaria horizontalis, Digitaria insularis, Digitaria sanguinalis* (DIGSA), *Echinochloa crus-galli* (English name "common barnyard grass", ECHCG), *Echinochloa oryzoides, Echinochloa colona* or *colonum, Eleusine indica, Eriochloa villosa* (English name "woolly cupgrass"), *Leptochloa chinensis, Leptochloa panicoides, Lolium perenne* (LOLPE, English name "perennial ryegrass"), *Lolium multiflorum* (LOLMU, English name "Italian ryegrass"), *Lolium persicum* (English name "Persian darnel"), *Lolium rigidum*, *Panicum dichotomiflorum* (PANDI), *Panicum miliaceum* (English name "wild proso millet"), *Phalaris minor*, *Phalaris paradoxa*, *Poa annua* (POAAN, English name "annual bluegrass"), *Scirpus maritimus*, *Scirpus juncoides*, *Setaria viridis* (SETVI, English name "green foxtail"), *Setaria faberi* (SETFA, English name "giant foxtail"), *Setaria glauca*, *Setaria lutescens* (English name "yellow foxtail"), *Sorghum bicolor*, and/or *Sorghum halepense* (English name "Johnson grass"), and/or *Sorghum vulgare*; and/or volunteer corn (volunteer maize) weeds.

In one embodiment, grassy monocotyledonous weeds to be controlled comprise weeds from the genus: *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*, and/or volunteer corn (volunteer maize) weeds; in particular: weeds from the genus *Agrostis, Alopecurus, Apera, Avena, Brachiaria, Bromus, Cenchrus, Digitaria, Echinochloa, Eleusine, Eriochloa, Leptochloa, Lolium, Panicum, Phalaris, Poa, Rottboellia, Setaria*, and/or *Sorghum*, and/or volunteer corn (volunteer maize) weeds.

In a further embodiment, the grassy monocotyledonous weeds are "warm-season" (warm climate) grassy weeds; in which case they preferably comprise (e.g. are): weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*, and/or volunteer corn (volunteer maize) weeds. More preferably, the grassy monocotyledonous weeds, e.g. to be controlled and/or growth-inhibited, are "warm-season" (warm climate) grassy weeds comprising (e.g. being): weeds from the genus *Brachiaria, Cenchrus, Digitaria, Echinochloa, Eleusine, Eriochloa, Panicum, Setaria* and/or *Sorghum*, and/or volunteer corn (volunteer maize) weeds.

In another particular embodiment the grassy monocotyledonous weeds, are "cool-season" (cool climate) grassy weeds; in which case they typically comprise weeds from the genus *Agrostis, Alopecurus, Apera, Avena, Bromus, Lolium* and/or *Poa*.

Various aspects and embodiments of the present invention will now be illustrated in more detail by way of example. It will be appreciated that modification of detail may be made without departing from the scope of the invention.

PREPARATION EXAMPLES

Throughout the following examples, 1H NMR spectra were recorded at 400 MHz or 500 MHz, unless otherwise stated, either on a Varian Unity Inova instrument or Bruker AVANCE—II instrument.

The following abbreviations are used: s=singlet; d=doublet; dd=double doublet; t=triplet; q=quartet; m=multiplet. The term app. is used for apparent and br. denotes a broader signal.

Molecules are given their known names or named according to the naming programs within Accelrys Draw 4.0 or Symyx Notebook 6.6. If such programs are unable to name a molecule, the molecule is named using agreed naming conventions.

Example 1 Preparation of compound A1 (tert-butyl N-methyl-N-[4-methyl-2-(3-pyridyl)thiazol-5-yl] carbamate)

1.1 Preparation of 4-methyl-2-(3-pyridyl)thiazole-5-carboxylate Ethyl Ester (Compound 1.1001)

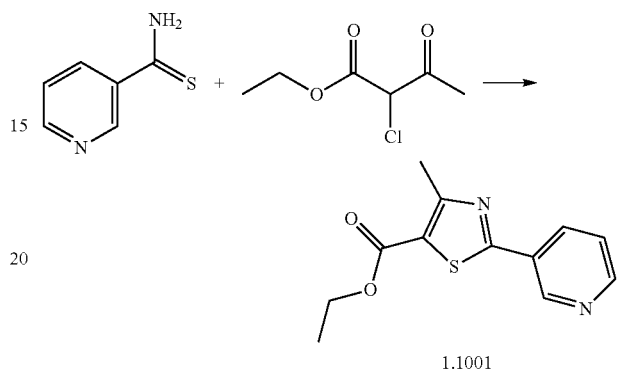

To a flask charged with thionicotinamide (10 g, 72.3 mmol) was added ethyl-2-chloroacetoacetate (11.9 g, 72.4 mmol) and heated at reflux in ethanol (100 mL) overnight. The next morning solvent was removed in vacuo and the residue partitioned between EtOAc and sat. aq. NaHCO$_3$ solution. The aqueous phase was extracted with two further portions of EtOAc. The combined organic extracts were washed with brine then dried over MgSO$_4$ and concentrated in vacuo. The resulting mixture was purified via flash chromatography on silica gel using an EtOAc/isohexane gradient to give the desired compound (4-methyl-2-(3-pyridyl)thiazole-5-carboxylate ethyl ester, 11.9 g) as a pale brown oil which slowly solidified.

1H NMR (400 MHz, CDCl$_3$) δ=9.17 (1H, m), 8.69 (1H, dd), 8.24 (1H, m), 7.40 (1H, m), 4.37 (2H, q), 2.80 (3H, s), 1.40 (3H, t)

1.2 Preparation of 4-methyl-2-(3-pyridyl)thiazole-5-carboxylic acid (1.2001)

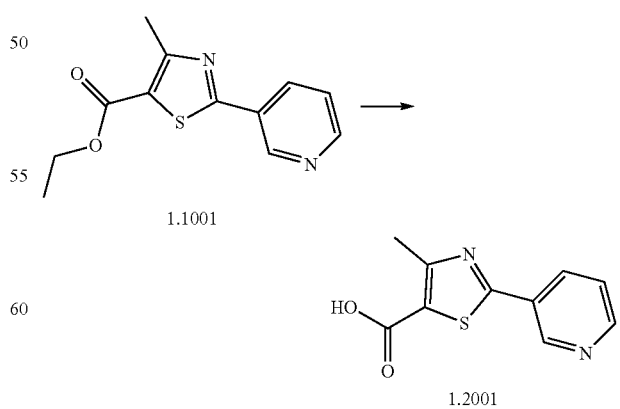

A solution of 4-methyl-2-(3-pyridyl)thiazole-5-carboxylate ethyl ester (compound 1.1001; 35.2 g, 142 mmol) in methanol (462 mL) was cooled in ice/water then a solution of NaOH (17.0 g, 425 mmol) in water (214 mL) was added slowly with stirring and stirred without cooling for one hour.

2M HCl (216 mL) was added slowly with stirring and ice/water cooling. The mixture was stirred for a further 30 mins. The resulting precipitate was filtered, washed with water and air-dried to give the desired compound (4-methyl-2-(3-pyridyl)thiazole-5-carboxylic acid, 28.1 g) as an off white solid.

1H NMR (400 MHz, d6-DMSO) δ=13.54 (1H, br. s.), 9.16 (1H, d), 8.72 (1H, dd), 8.35 (1H, m), 7.56 (1H, dd) 2.70 (3H, s)

1.3 Preparation of tert-butyl N-[4-methyl-2-(3-pyridyl)thiazol-5-yl]carbamate (1.3001)

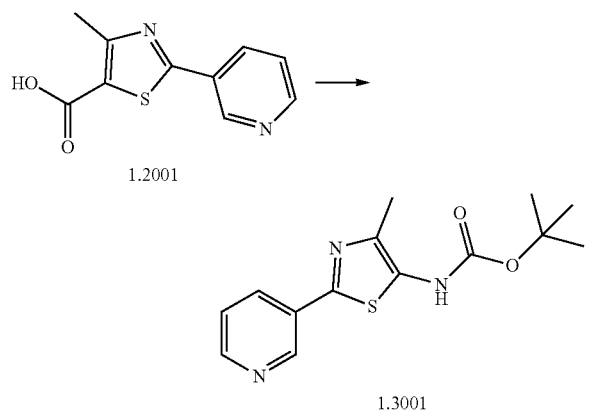

To a suspension of 4-methyl-2-(3-pyridyl)thiazole-5-carboxylic acid (compound 1.2001; 22.4 g, 101.7 mmol) in 2-methylpropan-2-ol (448 mL) and toluene (448 mL) was added Et$_3$N (14.2 mL, 101 mmol) and the reaction stirred for five minutes at room temperature before DPPA (27.8 g, 101 mmol) was added slowly with stirring and cooling to maintain the temperature below ambient. The reaction was heated gradually to reflux for 3 hours, then allowed to cool overnight to room temperature.

The solvent was removed in vacuo and the residue purified via flash column chromatography on silica gel using an EtOAc/isohexane gradient to give the desired compound (tert-butyl N-[4-methyl-2-(3-pyridyl)thiazol-5-yl]carbamate, 25.8 g) as a beige solid.

1H NMR (400 MHz, CDCl$_3$) δ=9.09 (1H, s), 8.59 (1H, d), 8.16 (1H, dd), 7.36 (1H, m), 6.72 (1H, br. s), 2.37 (3H, s), 1.49 (9H, br. s.)

1.4 Preparation of tert-butyl N-methyl-N-[4-methyl-2-(3-pyridyl)thiazol-5-yl]carbamate (A1)

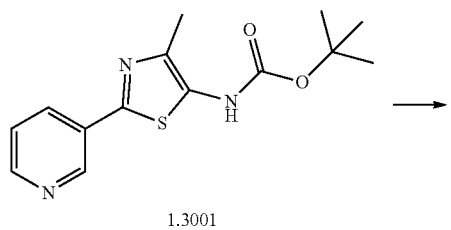

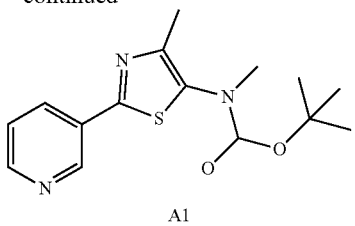

A solution of tert-butyl N-[4-methyl-2-(3-pyridyl)thiazol-5-yl]carbamate (compound 1.3001; 21.2 g, 72.7 mmol) in anhydrous DMF (245 mL) was cooled in ice/water and NaH 60% w/w (3.49 g, 87.3 mmol) was added portion-wise with stirring, then warmed to ambient over 5 minutes. The mixture was re-cooled in ice/water and then a solution of MeI (11.35 g, 80.0 mmol) in dry DMF (5 mL) was added dropwise with stirring and cooling over 30 minutes. The reaction was stirred at room temperature overnight and then cautiously quenched with water (1000 mL) and 2M HCl (7.29 mL). The reaction mixture was extracted three times with EtOAc, the combined organic extracts were washed twice with brine then dried over MgSO$_4$. The solvent was removed in vacuo and the residue purified via flash chromatography on silica gel using an EtOAc/isohexane gradient to give the desired compound (tert-butyl N-methyl-N-[4-methyl-2-(3-pyridyl)thiazol-5-yl]carbamate, 25.1 g) as a beige solid.

1H NMR (400 MHz, CDCl$_3$) δ=9.08 (1H, d), 8.63 (1H, dd), 8.17 (1H, d), 7.36 (1H, dd), 3.22 (3H, s), 2.33 (3H, s), 1.44 (9H, br.s.)

Example 2 Preparation of tert-butyl N-methyl-N-(4-methyl-2-pyrimidin-5-yl-thiazol-5-yl)carbamate (A2)

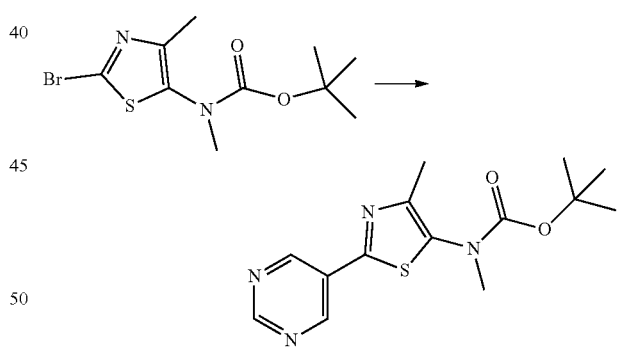

To a flask charged with pyrimidin-5-ylboronic acid (150.0 mg, 1.21 mmol) was added EtOH (2.7 mL) and toluene (5.3 mL) then 2M aq. K$_2$CO$_3$ (1.2 mL, 2.4 mmol) was added. The reaction was set stirring and tert-butyl N-(2-bromo-4-methyl-thiazol-5-yl)-N-methyl-carbamate (409 mg, 1.33 mmol) was added, followed by Pd(PPh$_3$)$_4$ (70 mg, 0.06 mmol). The mixture was heated at 90° C. for two hours and then allowed to cool overnight to ambient.

The mixture was diluted with EtOAc and washed twice with brine. The combined aqueous washings were back-extracted with EtOAc and the combined organic extracts were washed with brine and then dried over MgSO$_4$. The solvent was removed in vacuo and the residue purified via flash column chromatography on silica gel using an EtOAc/isohexane gradient to afford the desired compound (tert-butyl N-methyl-N-(4-methyl-2-pyrimidin-5-yl-thiazol-5-yl) carbamate, 170 mg) as a straw coloured gum.

1H NMR (400 MHz, CDCl₃) δ=9.23 (1H, s), 9.18 (2H, s), 3.23 (3H, s), 2.35 (3H, s), 1.45 (9H, br.s.)

Example 3 Preparation of tert-butyl N-[2-(5-fluoro-3-pyridyl)-4-methyl-thiazol-5-yl]-N-methyl-carbamate (A3)

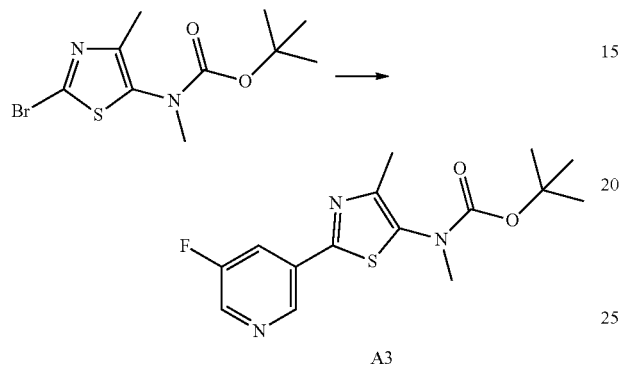

To a flask charged with tert-butyl N-(2-bromo-4-methyl-thiazol-5-yl)-N-methyl-carbamate (8.78 g, 27.8 mmol) and (5-fluoro-3-pyridyl)boronic acid (4.71 g, 33.4 mmol) was added ethanol (55.7 mL) and toluene (111.6 mL). Pd(PPh₃)₄ (1.50 g, 1.30 mmol) was added and the mixture stirred vigorously. 2M aq. K₂CO₃ (25.5 mL, 51.0 mmol) was added and the reaction was heated to reflux for 7 hours, then left to cool to ambient overnight.

Solvent was removed in vacuo and the crude material was re-dissolved in CHCl₃ and washed with water. The organic phase was concentrated in vacuo and the residue purified via flash column chromatography on silica gel using an EtOAc/isohexane gradient to give the desired compound (tert-butyl N-[2-(5-fluoro-3-pyridyl)-4-methyl-thiazol-5-yl]-N-methyl-carbamate, 6.92 g) as a beige solid.

1H NMR (400 MHz, CDCl₃) δ=8.85-8.89 (1H, m), 8.49 (1H, d), 7.93 (1H, dd), 3.23 (3H, s), 2.33 (3H, s), 1.45 (9H, br.s).

Example 4 Preparation of tert-butyl N-[2-(5-fluoro-3-pyridyl)-4-methyl-thiazol-5-yl]carbamate (A35)

4.1 Preparation of Compound A35

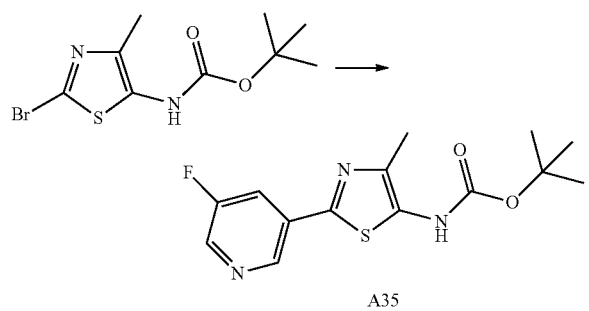

To a flask charged with tert-butyl N-(2-bromo-4-methyl-thiazol-5-yl)carbamate (11.31 g, 38.6 mmol) and (5-fluoro-3-pyridyl)boronic acid (6.52 g, 46.3 mmol) was added toluene (151 mL) and ethanol (75 mL). Pd(PPh₃)₄ (2.20 g, 1.90 mmol) was added, followed by 2M aq K₂CO₃ (38.6 mL, 77.2 mmol). The reaction was heated to reflux for five and a half hours. The reaction mixture was cooled to room temperature and concentrated in vacuo to remove the organics. The mixture was diluted with CHCl₃ and washed with water. The organic phase was concentrated in vacuo and the residue purified via flash column chromatography on silica using an EtOAc/isohexane gradient to afford the desired compound (tert-butyl N-[2-(5-fluoro-3-pyridyl)-4-methyl-thiazol-5-yl]carbamate, 10.2 g) as a beige solid.

1H NMR (400 MHz, CDCl₃) δ=8.87 (1H, m), 8.44 (1H, d), 7.94-7.87 (1H, m), 6.73 (1H, br. s), 2.39 (3H, s), 1.55 (9H, s)

4.2 Alternative Preparation of tert-butyl N-[2-(5-fluoro-3-pyridyl)-4-methyl-thiazol-5-yl]-N-methyl-carbamate (A3)

Compound A35 may also be used as an intermediate in an alternative method of producing compound A3.

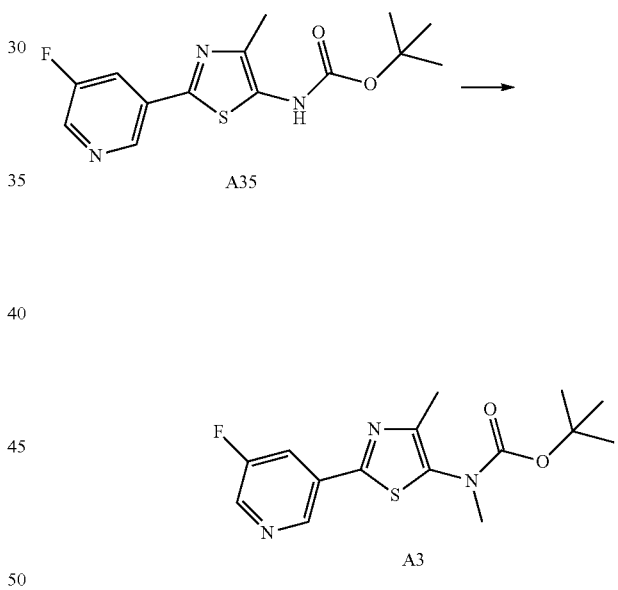

To a round bottomed flask charged with tert-butyl N-[2-(5-fluoro-3-pyridyl)-4-methyl-thiazol-5-yl]carbamate (800 mg, 2.59 mmol) and K₂CO₃ (429 mg, 3.10 mmol) was added iodomethane (807 mg, 5.69 mmol) as a solution in MeCN (20 mL) and the mixture set vigorously stirring. After 5 minutes the reaction was heated to reflux for 2 hours. Upon cooling the mixture was filtered through celite and concentrated in vacuo. The resulting semi-solid was purified via flash column chromatography on silica gel using an EtOAc/isohexane gradient to afford the desired compound (tert-butyl N-[2-(5-fluoro-3-pyridyl)-4-methyl-thiazol-5-yl]-N-methyl-carbamate, 449 mg) as a yellow gum.

1H NMR (400 MHz, CDCl₃) δ=8.85-8.89 (1H, m), 8.49 (1H, d), 7.93 (1H, dd), 3.23 (3H, s), 2.33 (3H, s), 1.45 (9H, br.s.)

Example 5 Preparation of tert-butyl N-[2-[5-(difluoromethoxy)-3-pyridyl]-4-methyl-thiazol-5-yl]-N-methyl-carbamate (A16)

5.1 Preparation of tert-butyl N-(2-bromo-4-methyl-thiazol-5-yl)carbamate (Compound 5.1001)

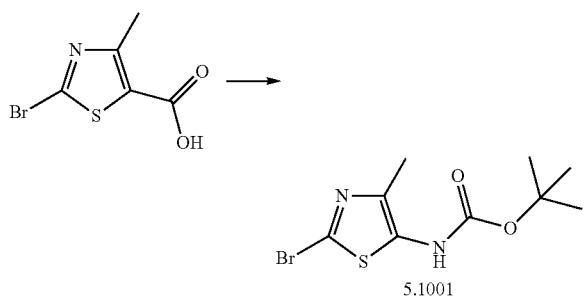

To a flask charged with 2-bromo-4-methyl-thiazole-5-carboxylic acid (5.0 g, 22.5 mmol) and Et$_3$N (3.14 mL, 22.5 mmol) was added t-BuOH (193 mL) and the mixture was heated to reflux. DPPA (4.89 mL, 22.5 mmol) was added dropwise over ca. 15 mins, then stirred at reflux for a further 6.5 hours, then allowed to cool overnight.

The reaction mixture was concentrated in vacuo and the residue was diluted with EtOAc (95 mL) and washed with water (140 mL). The aqueous phase was back-extracted twice more with EtOAc and the combined organics were washed with brine and dried over MgSO$_4$. The solvent was removed in vacuo and the residue purified via flash column chromatography on silica gel using an EtOAc/isohexane gradient to afford the desired compound (tert-butyl N-(2-bromo-4-methyl-thiazol-5-yl)carbamate, 5.4 g) as an opaque gum.

1H NMR (400 MHz, CDCl$_3$) 6.32 (1H, br. s), 2.29 (3H, s), 1.51 (9H, s)

5.2 Preparation of tert-butyl N-(2-bromo-4-methyl-thiazol-5-yl)-N-methyl-carbamate (5.2001)

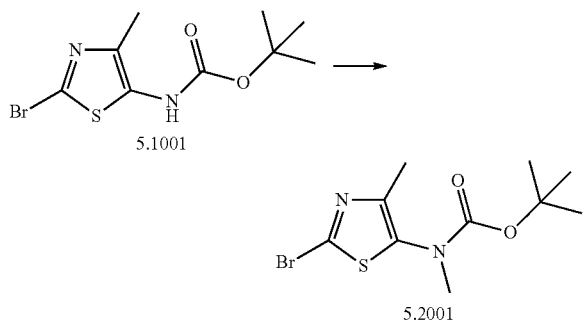

To a flask charged with tert-butyl N-(2-bromo-4-methyl-thiazol-5-yl)carbamate (32.0 g, 109.12 mmol) was added DMF (130 mL), the reaction was cooled in an ice bath and NaH 60% w/w (4.8 g, 120 mmol) added portion-wise with stirring and cooling to maintain the temperature in the range 5-10° C. The mixture was stirred for 10 mins then allowed to warm to ambient over ca. 40 mins. The reaction was cooled in an ice bath then iodomethane (16.27 g, 114.6 mmol) in DMF (100 mL) was added slowly with stirring and cooling to maintain the temperature in the range 5-10 C. The reaction was allowed to warm to ambient and stirred for a further 5 hours. The reaction mixture was cooled in an ice bath and quenched by the cautious addition of water (920 mL).

The reaction mixture was extracted three times with EtOAc and the combined organics washed with brine and dried over MgSO$_4$. The solvent was removed in vacuo and the residue purified via flash column chromatography on silica gel eluting with an EtOAc/isohexane gradient to afford the desired compound (tert-butyl N-(2-bromo-4-methyl-thiazol-5-yl)-N-methyl-carbamate, 33.2 g) as a colourless oil.

1H NMR (400 MHz, CDCl$_3$) δ=1.43 (9H, br. s.), 2.24 (3H, s), 3.16 (3H, s)

5.3 Preparation of 3-(difluoromethoxy)-5-(4,4,5,5-tetramethyl-1,3,2-dioxaborolan-2-yl)pyridine (5.3001)

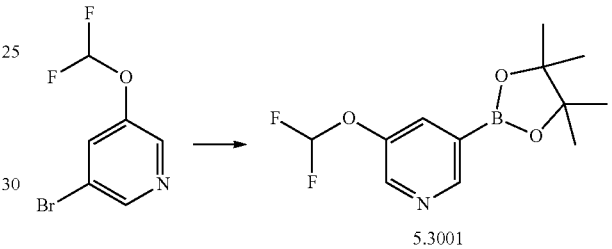

To a flask charged with 3-bromo-5-(difluoromethoxy)pyridine (4.50 g, 20.1 mmol) was added bispinacolatodiboron (7.65 g, 30.1 mmol), [1,1'-bis(diphenylphosphino)-ferrocene]palladium(ii) dichloride dichloromethane adduct (837 mg, 1.00 mmol) and KOAc (6.5 g, 64.0 mmol). 1,4-Dioxane (95 mL) was added and the mixture was purged with dry N$_2$ and heated at 100° C. for 1 hour.

The reaction was cooled to ambient and concentrated in vacuo. The residue was dissolved in CH$_2$Cl$_2$ and filtered through celite. The filtrate was concentrated in vacuo to give a thick black oil which was purified via flash column chromatography on silica gel using an EtOAc/isohexane gradient to afford the desired compound (3-(difluoromethoxy)-5-(4,4,5,5-tetramethyl-1,3,2-dioxaborolan-2-yl)pyridine, 3.95 g) as a straw coloured oil which crystallized on standing.

$^1$H NMR (400 MHz, CDCl$_3$) δ=8.80 (1H, d), 8.54 (1H, d), 7.82 (1H, m), 6.76-6.36 (1H, t), 1.36 (12H, s)

5.4 Preparation of tert-butyl N-[2-[5-(difluoromethoxy)-3-pyridyl]-4-methyl-thiazol-5-yl]-N-methyl-carbamate (A16)

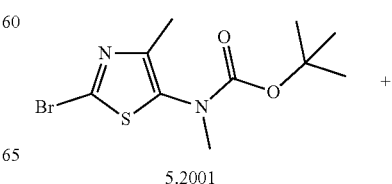 +

-continued

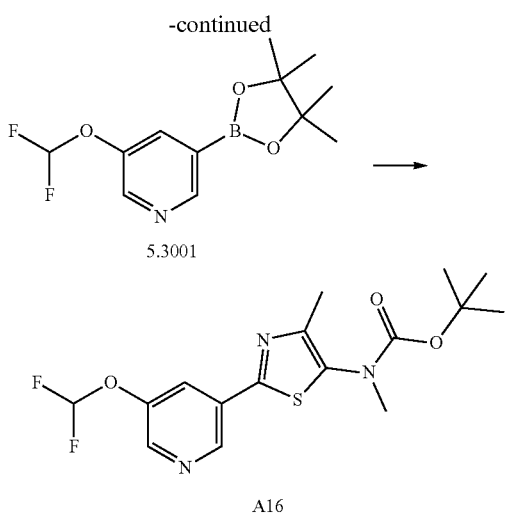

A16

To a microwave vial charged with tert-butyl N-(2-bromo-4-methyl-thiazol-5-yl)-N-methyl-carbamate (500 mg, 1.59 mmol) and 3-(difluoromethoxy)-5-(4,4,5,5-tetramethyl-1,3,2-dioxaborolan-2-yl)pyridine (430 mg, 1.59 mmol) was added EtOH (2 mL) and toluene (4 mL). Pd(PPh₃)₄ (85.3 mg, 0.074 mmol) was added, followed by 2M K₂CO₃ (1.45 mL, 2.90 mmol) and the tube sealed. The mixture was heated to 130 C for 30 minutes under microwave irradiation.

Upon cooling the solvent was removed in vacuo and residue partitioned between CHCl₃ and water. The organic phase was concentrated in vacuo to give a black gum which was purified via flash column chromatography on silica gel using a EtOAc/isohexane gradient to afford impure tert-butyl N-[2-[5-(difluoromethoxy)-3-pyridyl]-4-methyl-thiazol-5-yl]-N-methyl-carbamate. This material was further purified via flash column chromatography on a C₁₈ reverse phase column using a water (0.1% formic acid modifier)/MeCN (0.1% formic acid modifier) gradient to afford the desired compound (tert-butyl N-[2-[5-(difluoromethoxy)-3-pyridyl]-4-methyl-thiazol-5-yl]-N-methyl-carbamate, 352 mg).

1H NMR (400 MHz, CDCl₃) δ=8.91 (1H, d), 8.50 (1H, d), 7.99 (1H, s), 6.82-6.41 (1H, t), 3.23 (3H, s), 2.33 (3H, s), 1.45 (9H, br. s)

Example 6 Preparation of ethyl N-methyl-N-[4-methyl-2-(3-pyridyl)thiazol-5-yl]carbamate (A19)

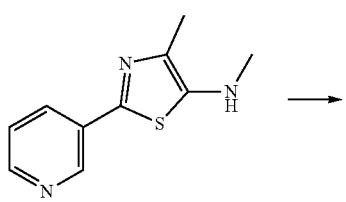

A19

To a flask charged with N,4-dimethyl-2-(3-pyridyl)thiazol-5-amine (300.0 mg, 1.46 mmol) dissolved in CH₂Cl₂ (4 mL) was added pyridine (173.4 mg, 2.192 mmol) and DMAP (17.9 mg, 0.147 mmol). The reaction mixture was cooled in an ice bath and a solution of ethyl chloroformate (206 mg, 1.90 mmol) in CH₂Cl₂ (1 mL) was added dropwise. After one hour at ambient the solvent was removed in vacuo. The residue was partitioned between water and EtOAc and the organic phase washed once with brine then dried (MgSO₄). The solvent was removed in vacuo and the residue purified via flash column chromatography on silica gel using an EtOAc/isohexane gradient as eluent to afford the target compound (ethyl N-methyl-N-[4-methyl-2-(3-pyridyl)thiazol-5-yl]carbamate, 280 mg) as a straw coloured gum.

1H NMR (400 MHz, CDCl₃) δ=9.08 (1H, d), 8.64 (1H, dd), 8.17 (1H, m), 7.37 (1H, dd), 4.20 (2H, q), 3.27 (3H, s), 2.33 (3H, s), 1.24 (3H, app. br. s)

Example 7 Preparation of 3-tert-butyl-1-methyl-1-[4-methyl-2-(3-pyridyl)thiazol-5-yl]urea (A21)

7.1 Preparation of 2-(5-fluoro-3-pyridyl)-N,4-dimethyl-thiazol-5-amine hydrochloride (7.1001)

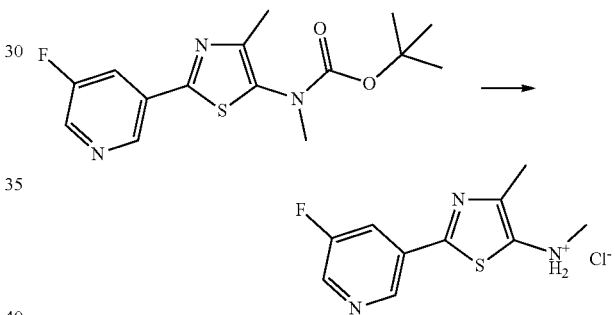

To a solution of tert-butyl N-[2-(5-fluoro-3-pyridyl)-4-methyl-thiazol-5-yl]-N-methyl-carbamate (4.23 g, 13.1 mmol) in CH₂Cl₂ (66 mL), cooled with an ice bath, was added 2M hydrogen chloride in Et₂O (65.4 mL, 130.7 mmol) slowly with stirring. The mixture was stirred in the ice bath for a further 5 minutes then allowed to stand overnight and stirred at ambient for a further 2 days.

Concentration in vacuo yielded the desired compound (2-(5-fluoro-3-pyridyl)-N,4-dimethyl-thiazol-5-amine hydrochloride, 3.84 g) as an orange solid.

1H NMR (400 MHz, d6-DMSO) δ=8.79 (1H, m), 8.51 (1H, d), 8.01 (1H, m), 2.85 (3H, s), 2.25 (3H, s)

7.2 Preparation of 3-tert-butyl-1-methyl-1-[4-methyl-2-(3-pyridyl)thiazol-5-yl]urea (A21)

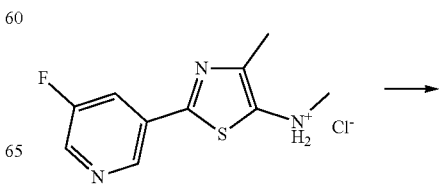

-continued

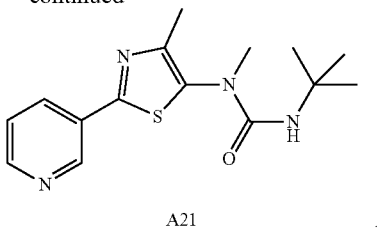

A21

A solution of N,4-dimethyl-2-(3-pyridyl)thiazol-5-amine hydrochloride (600.0 mg, 2.92 mmol) in CH$_2$Cl$_2$ (9 mL) was cooled in an ice bath and a solution of t-butylisocyanate (348 mg, 3.51 mmol) in CH$_2$Cl$_2$ (1 mL) was added drop-wise. The reaction was allowed to warm to ambient and allowed to stir for 3 days.

The solvent was removed in vacuo and the residue purified via flash column chromatography on silica gel eluted with a CH$_2$Cl$_2$/EtOAc gradient to afford the desired compound (3-tert-butyl-1-methyl-1-[4-methyl-2-(3-pyridyl) thiazol-5-yl]urea, 300 mg) as a white solid.

1H NMR (400 MHz, CDCl$_3$) δ=9.12 (1H, d), 8.67 (1H, dd), 8.19 (1H, m), 7.39 (1H, dd), 4.48 (1H, br. s), 3.20 (3H, s), 2.35 (3H, s), 1.30 (9H, br. s)

Example 8 Preparation of S-tert-butyl N-methyl-N-[4-methyl-2-(3-pyridyl)thiazol-5-yl]carbamothioate (A22)

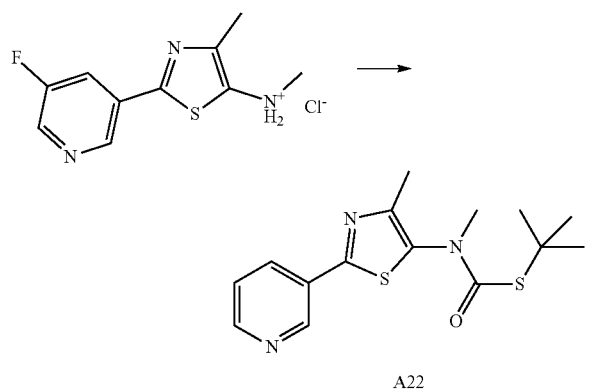

A22

To a flask charged with N,4-dimethyl-2-(3-pyridyl)thiazol-5-amine hydrochloride (300.0 mg, 1.46 mmol) was added CH$_2$Cl$_2$ (4 mL), pyridine (173.4 mg, 2.19 mmol) and DMAP (17.9 mg, 0.15 mmol). The reaction mixture was cooled in an ice bath and a solution of S-tert-butyl chlorothioformate (290 mg, 1.90 mmol) in CH$_2$Cl$_2$ (1 mL) was added drop-wise. The reaction was allowed to stir at ambient for one hour.

The solvent was removed in vacuo and the residue partitioned between water and EtOAc. The organic phase was washed with brine then dried (MgSO$_4$). Concentration in vacuo afforded a thick residue which was purified via flash column chromatography on silica gel using an EtOAc/isohexane gradient to afford the desired compound (S-tert-butyl N-methyl-N-[4-methyl-2-(3-pyridyl)thiazol-5-yl]carbamothioate, 290 mg) as a pale yellow gum.

1H NMR (400 MHz, CDCl$_3$) δ=9.12 (1H, d), 8.66 (1H, dd), 8.20 (1H, m), 7.38 (1H, dd), 3.25 (3H, s), 2.35 (3H, s), 1.47 (9H, m)

Example 9 Preparation of tert-butyl N-methyl-N-[4-methyl-2-(3-pyridyl)thiazol-5-yl]carbamodithioate (A23)

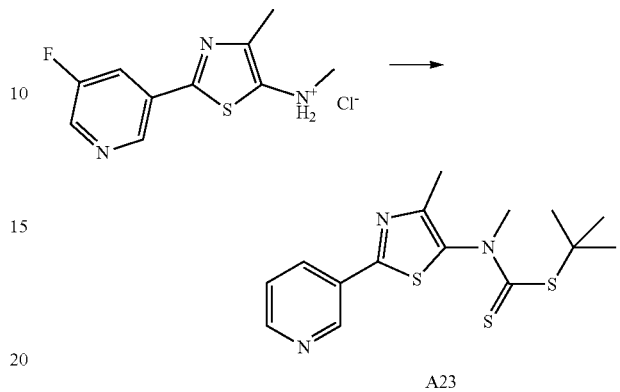

A23

To a flask charged with N,4-dimethyl-2-(3-pyridyl)thiazol-5-amine hydrochloride (300.0 mg, 1.47 mmol) was added EtOH (1.0 mL). The mixture was cooled in an ice bath and carbon disulphide (127 μL, 2.11 mmol) was added followed by K$_2$CO$_3$ (235 mg, 1.68 mmol). The mixture was allowed to warm gradually to ambient overnight.

2-Iodo-2-methyl-propane (194 μL, 1.47 mmol) was added and the reaction stirred at ambient for three days. The solvent was removed in vacuo and the residue was partitioned between water and EtOAc. The organic phase was washed once with brine and concentrated in vacuo and the residue purified via flash column chromatography on silica gel using an EtOAc/isohexane gradient to afford the desired compound (tert-butyl N-methyl-N-[4-methyl-2-(3-pyridyl) thiazol-5-yl]carbamodithioate, 37 mg) as a pale yellow gum.

1H NMR (400 MHz, CDCl$_3$) δ=9.14 (1H, d), 8.68 (1H, dd), 8.25 (1H, m), 7.44 (1H, m), 3.65 (3H, s), 2.32 (3H, s), 1.59 (9H, s)

Example 10 Preparation of tert-butyl N-[2-(5-methoxy-3-pyridyl)-4-(trifluoromethyl)thiazol-5-yl]-N-methyl-carbamate (A28)

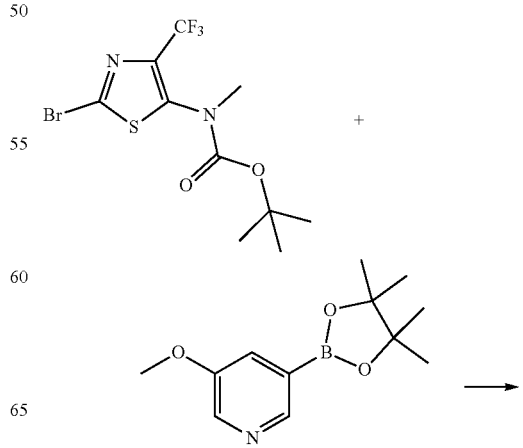

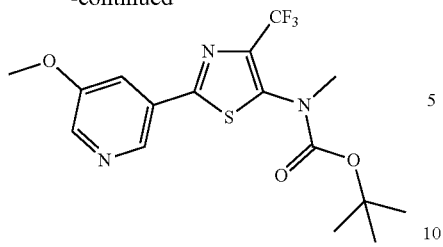

A28

To a microwave tube charged with tert-butyl N-[2-bromo-4-(trifluoromethyl)thiazol-5-yl]-N-methyl-carbamate (200 mg, 0.55 mmol) and 3-methoxy-5-(4,4,5,5-tetramethyl-1,3,2-dioxaborolan-2-yl)pyridine (131 mg, 0.56 mmol) was added ethanol (1.2 mL) and toluene (2.4 mL) then 2M $K_2CO_3$ (549 µL, 1.1 mmol) followed by $Pd(PPh_3)_4$ (33 mg, 0.03 mmol). The tube was sealed and the reaction was heated to 130° C. for 20 mins under microwave irradiation.

Upon cooling the solvent was removed in vacuo and the residue dissolved in $CHCl_3$, and washed with water. The reaction mixture was concentrated in vacuo to leave a dark brown gum, which was purified via flash column chromatography on silica gel using an EtOAc/isohexane gradient to afford the desired compound (tert-butyl N-[2-(5-methoxy-3-pyridyl)-4-(trifluoromethyl)thiazol-5-yl]-N-methyl-carbamate, 92 mg) as a beige solid.

1H NMR (500 MHz, $CDCl_3$) δ=8.64 (1H, d), 8.40 (1H, d), 7.77 (1H, br. s), 3.95 (3H, s), 3.26 (3H, s), 1.43 (9H, br. s)

Example 11 Preparation of tert-butyl N-[4-bromo-2-(3-pyridyl)thiazol-5-yl]-N-methyl-carbamate (A30)

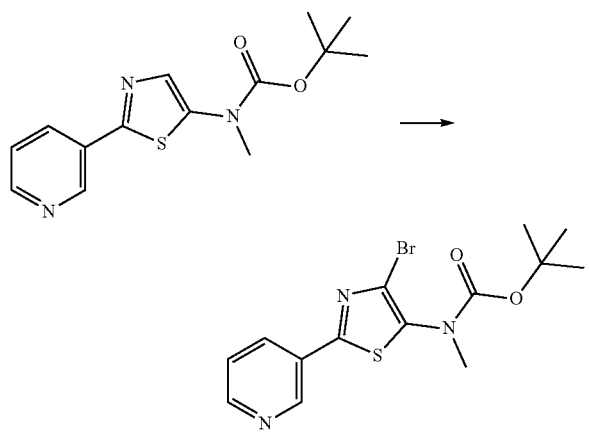

A30

To a flask charged with tert-butyl N-methyl-N-[2-(3-pyridyl)thiazol-5-yl]carbamate (150 mg, 0.52 mmol) was added MeCN (3.0 mL), the mixture was purged with dry $N_2$ then NBS (183 mg, 1.03 mmol) was added in a single portion. The mixture was stirred for an hour at ambient and then left to stand for 4 days.

The reaction mixture was concentrated in vacuo and the residue purified via flash column chromatography on silica gel eluting with a EtOAc/isohexane gradient to afford the desired compound (tert-butyl N-[4-bromo-2-(3-pyridyl)thiazol-5-yl]-N-methyl-carbamate, 110 mg) as colourless gum.

1H NMR (400 MHz, $CDCl_3$) δ=9.08 (1H, d), 8.70-8.64 (1H, m), 8.20 (1H, m), 7.42-7.37 (1H, m), 3.25 (3H, s), 1.46 (9H, br. s)

Example 12 Preparation of tert-butyl N-[4-iodo-2-(3-pyridyl)thiazol-5-yl]-N-methyl-carbamate (A31)

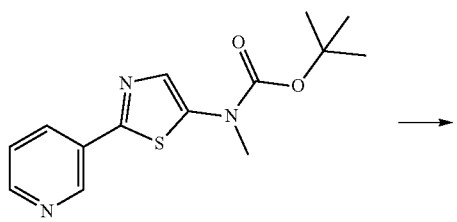

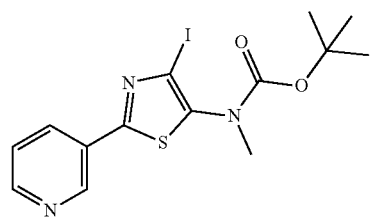

A31

To a flask charged with tert-butyl N-methyl-N-[2-(3-pyridyl)thiazol-5-yl]carbamate (1.1 g, 3.8 mmol) was added MeCN (33 mL), the reaction was cooled in ice, purged with dry $N_2$ then NIS (1.78 g, 7.91 mmol) was added in a single portion. The mixture was allowed to warm to ambient and stirred for a further 7 days.

The reaction mixture was concentrated in vacuo and the residue purified via flash column chromatography on silica gel eluting with a EtOAc/isohexane gradient to afford the desired compound (tert-butyl N-[4-iodo-2-(3-pyridyl)thiazol-5-yl]-N-methyl-carbamate, 1.02 g) as a beige solid.

1H NMR (400 MHz, $CDCl_3$) δ=9.08 (1H, d), 8.67 (1H, dd), 8.22 (1H, m), 7.40 (1H, dd), 3.24 (3H, s), 1.46 (9H, br. s)

Example 13 Preparation of tert-butyl N-[4-fluoro-2-(3-pyridyl)thiazol-5-yl]-N-methyl-carbamate (A32)

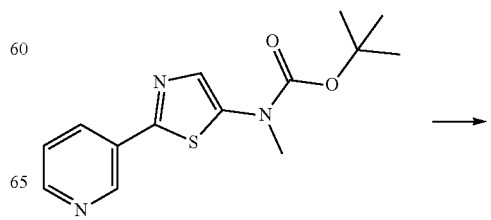

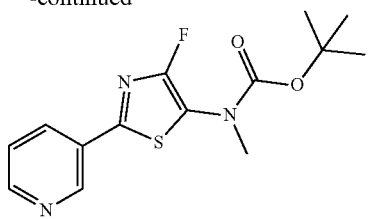

A32

To a flask charged with tert-butyl N-methyl-N-[2-(3-pyridyl)thiazol-5-yl]carbamate (150 mg, 0.51 mmol), dissolved in MeCN (6.1 mL) and purged with dry $N_2$ was added SelectFluor® (364.7 mg, 1.03 mmol) in a single portion. The reaction was again flushed with dry $N_2$ then stirred ambient for 5 hours. Water (15 mL) added then the mixture was extracted three times with EtOAc. The combined organics were dried ($MgSO_4$) and the solvent was concentrated in vacuo. The residue was purified via flash column chromatography on silica gel eluting with an EtOAc/isohexane gradient to afford the desired compound (tert-butyl N-[4-fluoro-2-(3-pyridyl)thiazol-5-yl]-N-methyl-carbamate, 60 mg) as a straw coloured gum.

1H NMR (500 MHz, $CDCl_3$) δ=9.06 (1H, d), 8.65 (1H, d), 8.13 (1H, d), 7.38 (1H, dd), 3.30 (3H, br. s), 1.50 (9H, br. s)

Example 14 Preparation of 3-methyl-1-[4-methyl-2-(3-pyridyl)thiazol-5-yl]imidazolidine-2,4-dione (A33)

14.1 Preparation of 4-methyl-2-(3-pyridyl)thiazole (14.1001)

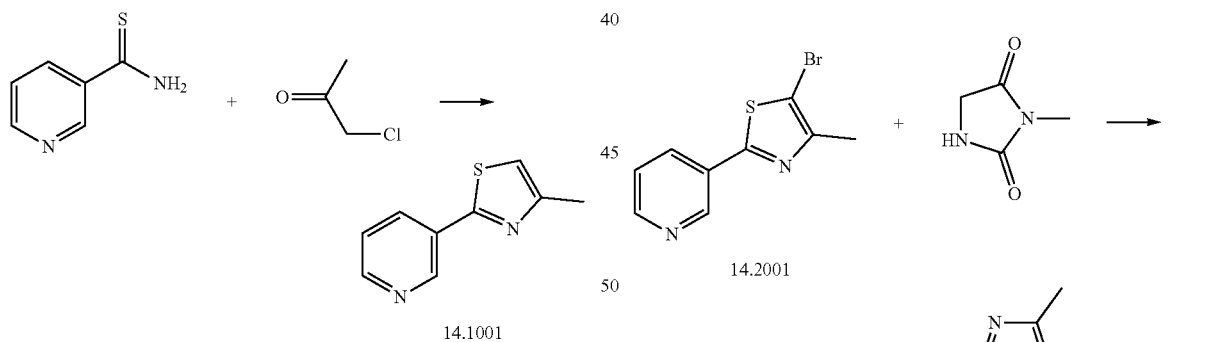

14.1001

To a flask charged with thionicotinamide (50 g, 361.8 mmol) was added EtOH (300 mL) followed by chloroacetone (40 g, 432.3 mmol) and the mixture was heated to reflux overnight.

Upon cooling the solvent was removed in vacuo and the residue was dissolved in water (400 mL) and made basic with $NaHCO_3$. This mixture was extracted three times with EtOAc and the combined organics washed once with brine then dried ($MgSO_4$). The organics were concentrated in vacuo and the residue purified via flash column chromatography on silica gel using an EtOAc/isohexane gradient to give the desired compound (4-methyl-2-(3-pyridyl)thiazole, 38.8 g) as a straw coloured oil.

1H NMR (400 MHz, $CDCl_3$) δ=9.15 (1H, d), 8.63 (1H, dd), 8.22 (1H, m), 7.36 (1H, m), 6.95 (1H, s), 2.53 (3H, s)

14.2 Preparation of 5-bromo-4-methyl-2-(3-pyridyl)thiazole (14.2001)

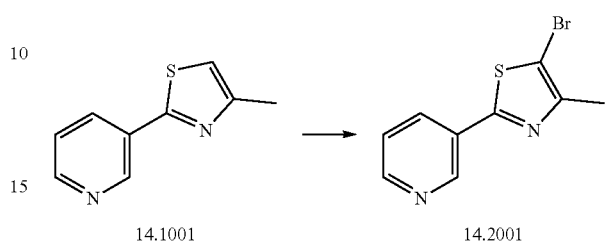

4-Methyl-2-(3-pyridyl)thiazole (10.0 g, 56.7 mmol) was dissolved in DMF (100 mL) and NBS (11.1 g, 62.4 mmol) was added with cooling to keep the temperature at below ambient. The reaction was heated at 50 C for ca. 3 hours and left to cool overnight.

The reaction was quenched with water (400 mL) and extracted three times with EtOAc. The combined organics were washed three times with brine and dried ($MgSO_4$). The reaction mixture was concentrated in vacuo and the residue was purified via flash column chromatography on silica gel using an EtOAc/isohexane gradient to give 5-bromo-4-methyl-2-(3-pyridyl)thiazole (13.24 g, 51.9 mmol) as a beige solid.

1H NMR (400 MHz, $CDCl_3$) δ=9.06 (1H, m) 8.66 (1H, dd) 8.15 (1H, s) 7.35-7.41 (1H, m) 2.48 (3H, s)

14.3 Preparation of 3-methyl-1-[4-methyl-2-(3-pyridyl)thiazol-5-yl]imidazolidine-2,4-dione (A33)

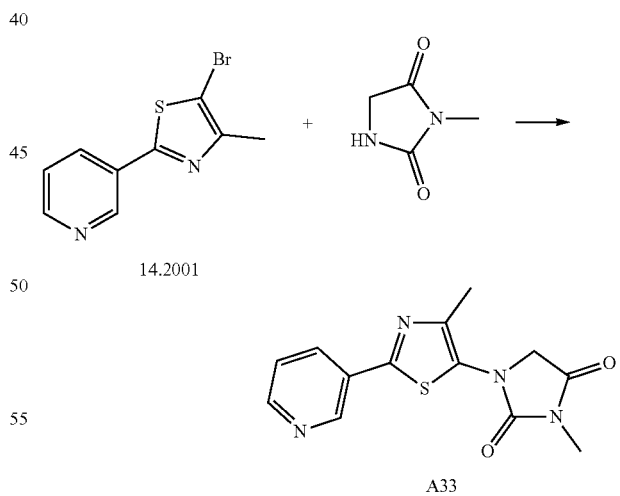

A33

To a microwave tube charged with 5-bromo-4-methyl-2-(3-pyridyl)thiazole (136 mg, 0.53 mmol) was added 3-methylimidazolidine-2,4-dione (121.6 mg, 1.07 mmol) and N,N'-dimethylethylenediamine (4.7 mg, 0.05 mmol) dissolved in 1,4-dioxane (3.2 mL). CuI (10.2 mg, 0.05 mmol) and $K_2CO_3$ (295 mg, 2.13 mmol) were added, the tube was sealed the mixture was heated at 160° C. for 1 hour under microwave irradiation.

The solvent was removed in vacuo and the residue partitioned between water and EtOAc, filtered to remove residual solid and partitioned. The aqueous phase was extracted with two further portions of EtOAc. The combined organic extracts were washed with brine, dried (MgSO₄), and concentrated in vacuo. The residue was purified via reverse phase flash chromatography a $C_{18}$ column eluted with a water and MeCN gradient to give the desired compound (3-methyl-1-[4-methyl-2-(3-pyridyl)thiazol-5-yl]imidazolidine-2,4-dione, 21 mg) as a white solid.

1H NMR (400 MHz, CDCl₃) δ=9.08 (1H, d), 8.66 (1H, dd), 8.17 (1H, m), 7.39 (1H, m), 4.28 (2H, s), 3.15 (3H, s), 2.43 (3H, s)

Example 15 Preparation of 3-[2-(5-fluoro-3-pyridyl)-4-methyl-thiazol-5-yl]oxazolidin-2-one (A38)

15.1 Preparation of 2-chloroethyl N-tert-butoxycarbonyl-N-[2-(5-fluoro-3-pyridyl)-4-methyl-thiazol-5-yl]carbamate (16.1001)

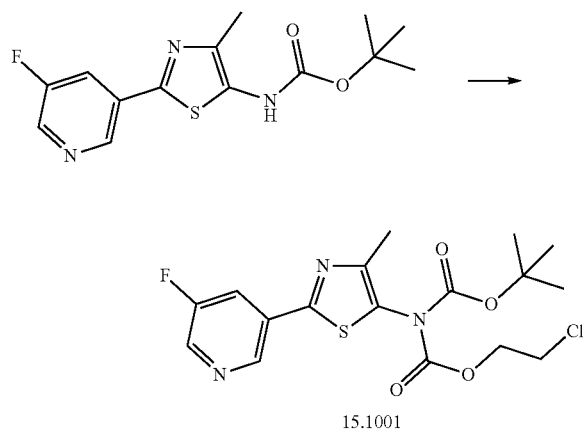

15.1001

To a flask charged with tert-butyl N-[2-(5-fluoro-3-pyridyl)-4-methyl-thiazol-5-yl]carbamate (800 mg, 2.59 mmol) was added dry THF (7 mL). The reaction was cooled in ice then sodium hydride 60% w/w (114 mg, 2.85 mmol) was added portionwise with stirring over 10 mins during which time the reaction had set solid. After standing at ambient for 20 mins, a solution of chloroethyl chloroformate (407 mg, 2.85 mmol) in THF (0.3 mL) was added. After a further 10 minutes stirring a hazy solution resulted, which was stirred for a further 3 hours at ambient.

The reaction was quenched with water (1 mL) and 2M HCl (528 1l) and then concentrated in vacuo, redissolved in CH₃Cl and partitioned with water. The organic solvent was concentrated in vacuo to yield a pale orange gum which was purified via flash column chromatography on silica gel using an EtOAc/isohexane gradient to give the desired compound (2-chloroethyl N-tert-butoxycarbonyl-N-[2-(5-fluoro-3-pyridyl)-4-methyl-thiazol-5-yl]carbamate, 520 mg) as a colourless gum.

1H NMR (400 MHz, CDCl₃) δ=8.90 (1H, m), 8.52 (1H, d), 7.96 (1H, m), 4.46 (2H, m), 3.68 (2H, m), 2.33 (3H, s), 1.48 (9H, s)

15.2 Preparation of 2-chloroethyl N-[2-(5-fluoro-3-pyridyl)-4-methyl-thiazol-5-yl]carbamate (16.2001)

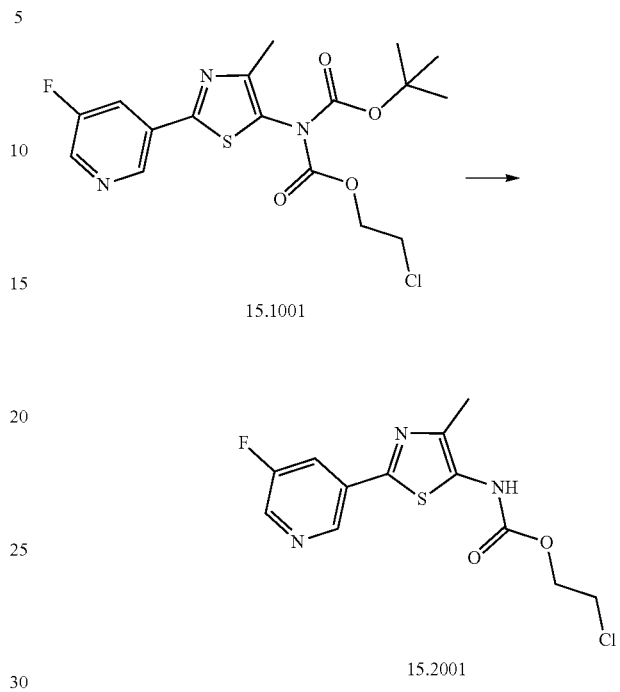

15.1001

15.2001

A flask charged with 2-chloroethyl N-tert-butoxycarbonyl-N-[2-(5-fluoro-3-pyridyl)-4-methyl-thiazol-5-yl]carbamate (625 mg, 1.50 mmol) and CH₂Cl₂ (6 mL) was cooled in an ice bath and TFA (3 mL) was added slowly with stirring for 5 minutes then left at ambient for 1 hour 45 minutes.

The solvent was removed in vacuo to leave a gum which was dissolved in CHCl₃, shaken with water and passed through a hydrophobic phase separating cartridge. The aqueous phase was neutralised with sat. aq. NaHCO₃, extracted with CHCl₃ and passed through a hydrophobic phase separating cartridge. The combined organics were concentrated in vacuo to give the desired compound (2-chloroethyl N-[2-(5-fluoro-3-pyridyl)-4-methyl-thiazol-5-yl]carbamate, 393 mg).

1H NMR (400 MHz, CDCl₃) b=8.88 (1H, m), 8.47 (1H, d), 7.94 (1H, m), 6.93 (1H, br. s), 4.50 (2H, m), 3.77 (2H, m), 2.41 (3H, s)

15.3 Preparation of 3-[2-(5-fluoro-3-pyridyl)-4-methyl-thiazol-5-yl]oxazolidin-2-one (A38)

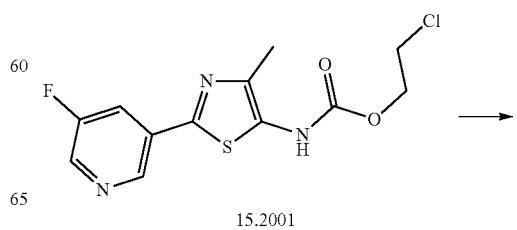

15.2001

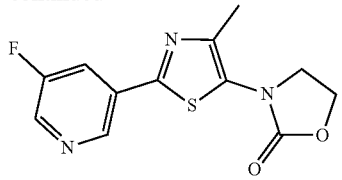

A38

A flask charged with 2-chloroethyl N-[2-(5-fluoro-3-pyridyl)-4-methyl-thiazol-5-yl]carbamate (202 mg, 0.64 mmol) and DMF (1.45 mL) was cooled in a salt/ice bath then sodium hydride 60% w/w (30.7 mg, 0.768 mmol) was added in one portion. The reaction mixture was stirred with cooling for 20 minutes then at ambient for a further 3 hours.

The reaction was cooled in ice then quenched with water (5.8 mL) and 2M HCl (63 µL). The reaction mixture was extracted three times with EtOAc and the combined organics washed once with brine and dried (MgSO$_4$), then concentrated in vacuo. The residue was purified via column chromatography on silica gel using an EtOAc/isohexane gradient to afford the desired compound (3-[2-(5-fluoro-3-pyridyl)-4-methyl-thiazol-5-yl]oxazolidin-2-one, 120 mg).

1H NMR (400 MHz, CDCl$_3$) δ=8.87 (1H, m), 8.51 (1H, d), 7.96-7.90 (1H, m), 4.64-4.53 (2H, m), 4.06-3.97 (2H, m), 2.52 (3H, s)

Example 16 Preparation of methyl 5-[tert-butoxycarbonyl(methyl)amino]-2-(3-pyridyl)thiazole-4-carboxylate (A39)

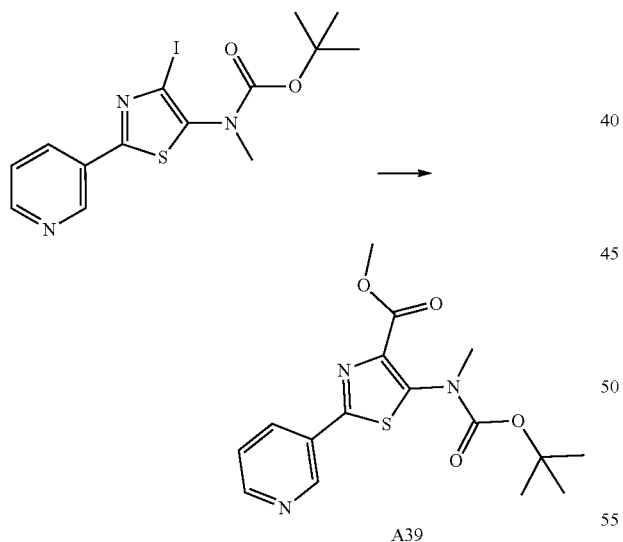

A39

To a flask charged with a solution of tert-butyl N-[4-iodo-2-(3-pyridyl)thiazol-5-yl]-N-methyl-carbamate (0.19 g, 0.44 mmol) in THF (1 mL) cooled to −78° C. was added n-BuLi (1.6M) in hexanes (0.55 mL, 0.89 mmol) drop-wise over 5 min. After 30 min stirring at −78° C., methyl chloroformate (0.07 mL, 0.89 mmol) was added. The mixture was stirred at −78° C. for one hour before being allowed to warm to ambient.

The reaction was quenched at room temperature by the addition of sat. aq. NH$_4$Cl solution and extracted with three portions of CH$_2$Cl$_2$. The combined organic extracts were dried (MgSO$_4$) and concentrated in vacuo. The residue was purified via flash column chromatography on silica gel eluted with an EtOAc/isohexane gradient, followed by further purification with reverse phase HPLC to give the desired compound (methyl 5-[tert-butoxycarbonyl(methyl)amino]-2-(3-pyridyl)thiazole-4-carboxylate, 4.7 mg)

1H NMR (400 MHz, CDCl$_3$) δ=9.23 (1H, br. s), 8.80 (1H, d), 8.64 (1H, d), 7.74 (1H, dd), 3.98 (3H, s), 3.31 (3H, s), 1.65-1.32 (9H, br. s)

Example 17 Preparation of tert-butyl N-methyl-N-[2-(3-pyridyl)-4-vinyl-thiazol-5-yl]carbamate (A40)

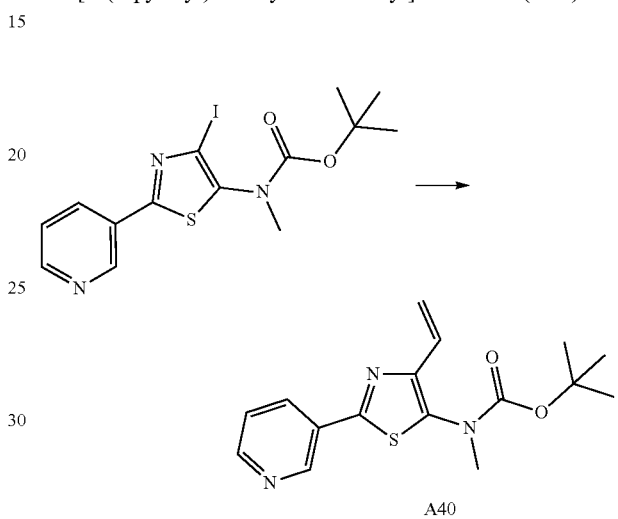

A40

To a microwave tube charged with tert-butyl N-[4-iodo-2-(3-pyridyl)thiazol-5-yl]-N-methyl-carbamate (80 mg, 0.19 mmol), tributyl(vinyl)stannane (0.122 g, 0.38 mmol) and PdCl$_2$(PPh$_3$)$_2$ (0.14 mg, 0.02 mmol) was added 1,4-dioxane (1 mL). The tube was sealed and heated at 140° C. for 30 min under microwave irradiation.

The reaction mixture was concentrated in vacuo and the residue purified via flash column chromatography on silica gel eluting with an EtOAc/isohexane gradient to give the desired compound (tert-butyl N-methyl-N-[2-(3-pyridyl)-4-vinyl-thiazol-5-yl]carbamate, 41.4 mg) as a brown gum.

1H NMR (400 MHz, CDCl$_3$) δ=9.08-9.01 (1H, m), 8.58 (1H, dd), 8.16 (1H, dd), 7.31 (1H, m), 6.50 (1H, dd), 6.16 (1H, dd), 5.42 (1H, dd), 3.17 (3H, s), 1.36 (9H, br. s)

Example 18 Preparation of tert-butyl N-[4-ethynyl-2-(3-pyridyl)thiazol-5-yl]-N-methyl-carbamate (A41)

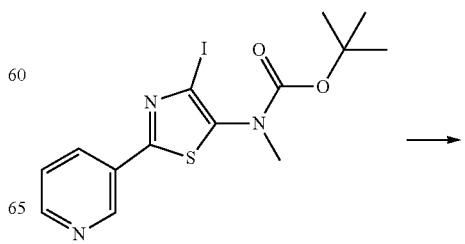

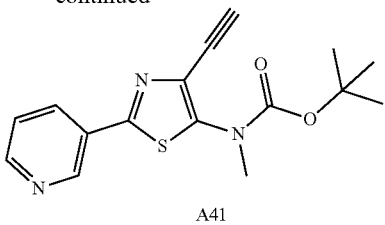

A41

To a microwave tube charged with tert-butyl N-[4-iodo-2-(3-pyridyl)thiazol-5-yl]-N-methyl-carbamate (100 mg, 0.24 mmol), tributyl(ethynyl)stannane (150 mg, 0.45 mmol) and PdCl$_2$(PPh$_3$)$_2$ (17 mg, 0.024 mmol) was added 1,4-dioxane (2 mL) and the tube was sealed. The reaction was sealed and heated to 140° C. for 30 min under microwave irradiation.

The reaction mixture was concentrated in vacuo and the residue purified via flash column chromatography on silica gel eluting with an EtOAc/isohexane gradient to afford the desired compound (tert-butyl N-[4-ethynyl-2-(3-pyridyl)thiazol-5-yl]-N-methyl-carbamate, 37 mg) as a brown gum.

1H NMR (400 MHz, CDCl$_3$) δ=9.09 (1H, d), 8.66 (1H, dd), 8.22 (1H, m), 7.38 (1H, dd), 3.43 (3H, s), 1.81 (1H, s), 1.51 (9H, br. s)

Example 19 Preparation of tert-butyl N-[4-cyclopropyl-2-(3-pyridyl)thiazol-5-yl]-N-methyl-carbamate (A43)

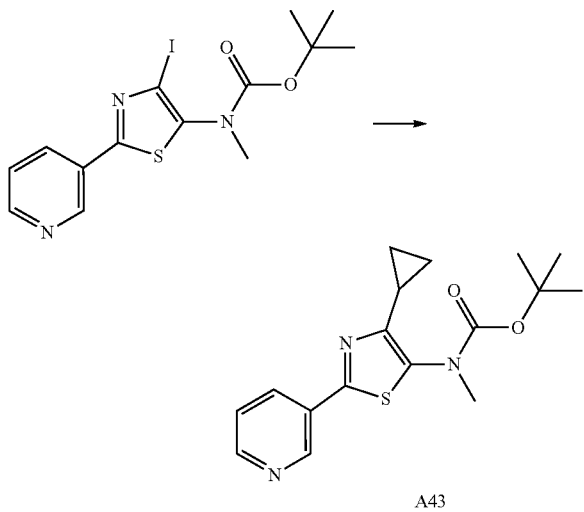

A43

To a microwave tube charged with tert-butyl N-[4-iodo-2-(3-pyridyl)thiazol-5-yl]-N-methyl-carbamate (100 mg, 0.24 mmol), cyclopropylboronic acid (27 mg, 0.31 mmol), tricyclohexylphosphine (6.7 mg, 0.024 mmol) and K$_3$PO$_4$ (180 mg, 0.84 mmol) was added toluene (0.72 mL) and water (50 µL). The solution was degassed by vacuum and purged with Ar, Pd(OAc)$_2$ (2.6 mg, 0.012 mmol) was added and the reaction was sealed and heated to 120° C. for 35 min under microwave irradiation.

The reaction mixture was then diluted with water and extracted with three portions of CH$_2$Cl$_2$. The combined organics were dried (MgSO$_4$) and concentrated in vacuo to give a brown gum which was purified via preparative reverse phase HPLC to afford the desired compound (tert-butyl N-[4-cyclopropyl-2-(3-pyridyl)thiazol-5-yl]-N-methyl-carbamate, 1.6 mg).

1H NMR (400 MHz, CDCl$_3$) δ=9.01 (1H, s), 8.60 (1H, d), 8.14 (1H, m), 7.32 (1H, dd), 3.20 (3H, s), 1.89-1.63 (5H, m), 1.39 (9H, br. s)

Example 20 Preparation of 5-[tert-butoxycarbonyl(methyl)amino]-2-(3-pyridyl)thiazole-4-carboxylic Acid (A44)

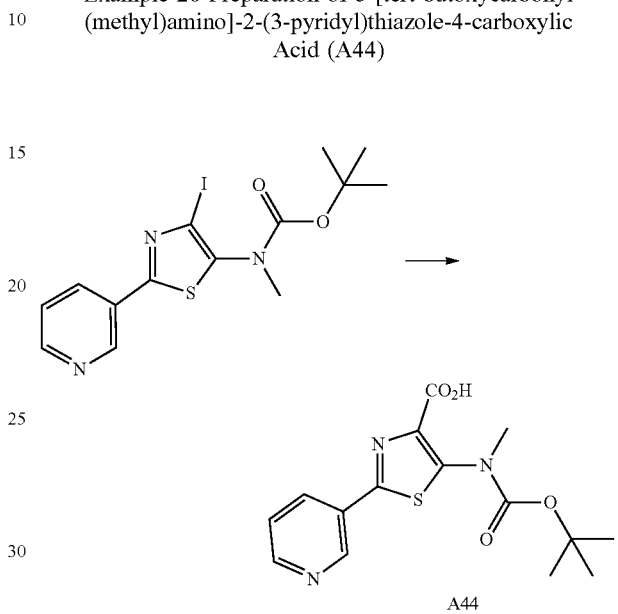

A44

To a flask charged with tert-butyl N-[4-iodo-2-(3-pyridyl)thiazol-5-yl]-N-methyl-carbamate (0.1 g, 0.24 mmol) was added THF (1 mL, 12.3 mmol) and the reaction cooled to −78° C. n-Butyllithium (1.6M) in hexanes (0.30 mL, 0.48 mmol) was then added dropwise over the course of 5 min. After 30 min stirring at −78° C., carbon dioxide was bubbled through the reaction mixture for 10 minutes from subliming dry ice. The reaction was allowed to warm to room temperature then quenched by the addition of sat. aqueous NH$_4$Cl and the resulting mixture was extracted with three portions CH$_2$Cl$_2$. The combined organic phases were dried over MgSO$_4$ and concentrated in vacuo to give a brown gum which was purified via reverse phase HPLC to give the desired compound (5-[tert-butoxycarbonyl(methyl)amino]-2-(3-pyridyl)thiazole-4-carboxylic acid, 5.9 mg).

1H NMR (400 MHz, CDCl$_3$) δ=9.37 (1H, app. br. s), 8.78 (1H, app. br.s), 8.43 (1H, d), 7.68 (1H, app. br. s), 3.37 (3H, s), 1.46 (9H, br.s)

Example 21 Preparation of 3-tert-butoxy-1-methyl-1-(4-methyl-2-(3-pyridyl)thiazol-5-yl)urea (A45)

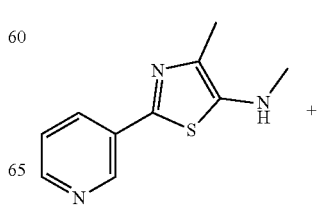

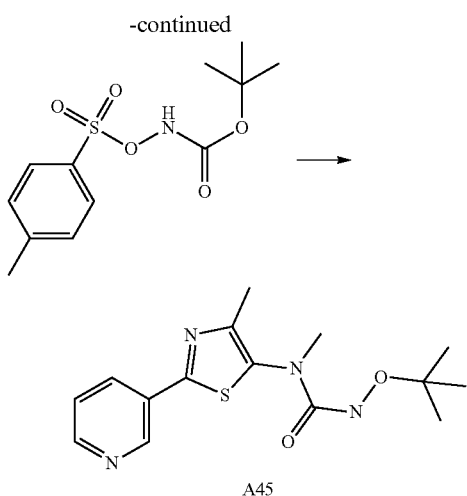

A45

To a flask charged with tert-butyl N-[2-(5-fluoro-3-pyridyl)-4-methyl-thiazol-5-yl]-N-methyl-carbamate (93 mg, 0.45 mmol) dissolved in DMF (2 mL) was added K$_2$CO$_3$ (82.0 mg, 0.59 mmol) and the reaction mixture was cooled to ca. 10° C. Then (tert-butoxycarbonylamino)-4-methylbenzenesulfonate (prepared according to the procedure of Thambidurai et al., Synlett 2011, 1993) (156.2 mg, 0.54 mmol) was added The resulting orange reaction was stirred for 3 days at ambient.

The solvent was removed in vacuo and the residue was dissolved in EtOAc, washed with water and the aqueous phase back-extracted three times with EtOAc. The combined organics were dried (Na$_2$SO$_4$), concentrated in vacuo and the residue purified via flash column chromatography on silica gel eluting with a CH$_2$Cl$_2$/methanol gradient to afford the desired compound (3-tert-butoxy-1-methyl-1-(4-methyl-2-(3-pyridyl)thiazol-5-yl)urea, 93 mg) as an orange solid.

1H NMR (400 MHz, CDCl$_3$) δ=9.12 (1H, s), 8.58 (1H, d), 8.18 (1H, d), 7.43 (1H, dd), 6.96 (1H, br. s), 3.28 (3H, s), 2.41 (3H, s), 1.23 (9H, s)

Example 22 Preparation of (4-nitrophenyl) N-methyl-N-[4-methyl-2-(3-pyridyl)thiazol-5-yl] carbamate (A61)

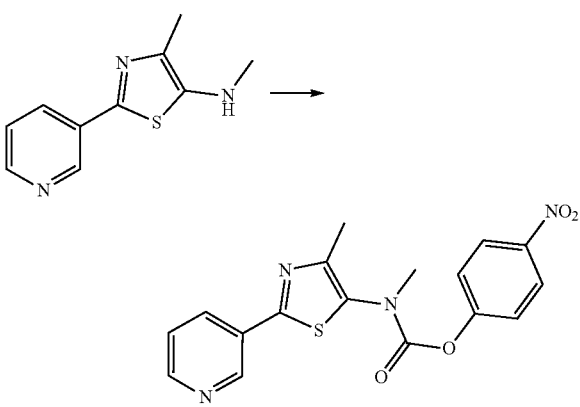

N,4-Dimethyl-2-(3-pyridyl)thiazol-5-amine (5.19 g, 23.0 mmol) and pyridine (2.73 g, 34.5 mmol) plus DMAP (287 mg, 2.30 mmol) were dissolved in CH$_2$Cl$_2$ (75 mL), cooled in an ice bath and a solution of (4-nitrophenyl) chloroformate (6.03 g, 29.9 mmol) in CH$_2$Cl$_2$ (25 mL) was added drop-wise with stirring. The flask was allowed to warm to ambient and stirred for a further 2 days. The reaction mixture was concentrated in vacuo and the residue partitioned between water and EtOAc. The aqueous phase was back extracted with EtOAc. The combined organic extracts were combined, washed once with brine, dried over MgSO$_4$, filtered and the filtrate concentrated in vacuo. The residue was purified via flash column chromatography on silica gel and eluted with a CH$_2$Cl$_2$/EtOAc gradient to afford the desired compound ((4-nitrophenyl)-N-methyl-N-[4-methyl-2-(3-pyridyl)thiazol-5-yl]carbamate, 7.51 g, ca. 92% purity) as a beige solid.

1H NMR (400 MHz, CDCl$_3$) δ=9.14 (1H, s), 8.67 (1H, dd), 8.33-8.26 (3H, m), 7.39 (1H, dd), 7.23-2.33 (2H, m), 3.40 (3H, s), 2.46 (3H, s)

Example 23 Preparation of 1,1-dimethylprop-2-ynyl N-methyl-N-[4-methyl-2-(3-pyridyl)thiazol-5-yl] carbamate (B3)

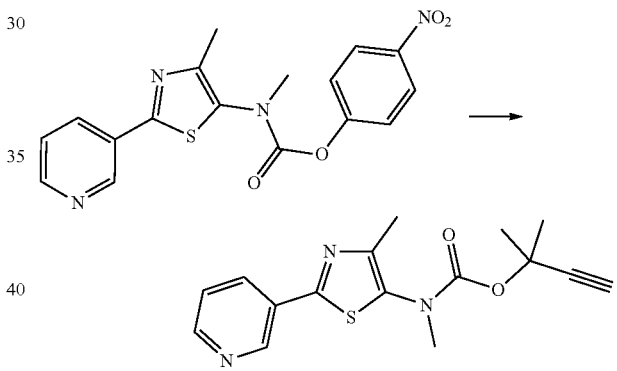

To a flask charged with 2-methylbut-3-yn-2-ol (84 mg, 1.00 mmol) dissolved in N,N-dimethylformamide (1.5 mL) and cooled in ice was added sodium hydride (60% suspension in oil w/w) (44 mg, 1.10 mmol). The flask was removed from the ice bath and stirred for 15 mins then re-cooled in ice/water. (4-Nitrophenyl) N-methyl-N-[4-methyl-2-(3-pyridyl)thiazol-5-yl]carbamate (200 mg, 0.497 mmol) was added with stirring and cooling. The reaction was warmed to room temperature and stirred for one further hour. The reaction was quenched with water (6 mL), extracted three times with EtOAc and the organic extracts washed with brine. The combined organics extracts were dried over MgSO$_4$ and solvent removed in vacuo. The crude residue was purified via reverse phase flash chromatography using a C$_{18}$ silica column and a water/acetonitrile gradient to afford the desired compound (1,1-dimethylprop-2-ynyl N-methyl-N-[4-methyl-2-(3-pyridyl)thiazol-5-yl]carbamate, 81 mg).

1H NMR (400 MHz, CDCl$_3$) δ=9.09 (1H, d), 8.64 (1H, dd), 8.18 (1H, d), 7.37 (1H, dd), 3.27 (3H, s), 2.59 (1H, s), 2.5 (3H, s), 1.81-1.53 (6H, br. s)

Example 24 Preparation of 1-methylprop-2-ynyl N-methyl-N-[4-methyl-2-(3-pyridyl)thiazol-5-yl] carbamate (B2)

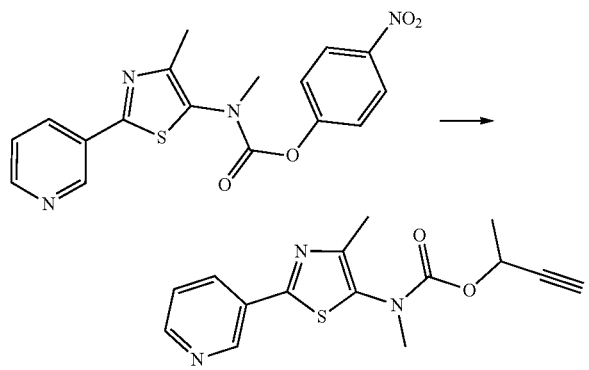

To a flask charged with but-3-yn-2-ol (70 mg, 1.00 mmol) dissolved in N,N-dimethylformamide (1.5 mL) and cooled in ice was added sodium hydride (60% suspension in oil w/w) (44 mg, 1.10 mmol). The flask was removed from the ice bath and stirred for 15 mins, then re-cooled with an ice bath. (4-Nitrophenyl) N-methyl-N-[4-methyl-2-(3-pyridyl) thiazol-5-yl]carbamate (200 mg, 0.50 mmol) was added with stirring and cooling. The reaction was warmed to room temperature and stirred for one further hour.

The reaction was quenched with water (6 mL) and extracted three times with EtOAc then the organic extracts washed with brine. The combined organic extracts were dried over MgSO$_4$ and solvent removed in vacuo. The crude residue was purified via reverse phase flash chromatography using a C$_{18}$ silica column and a water/acetonitrile gradient to afford the desired compound (1-methylprop-2-ynyl N-methyl-N-[4-methyl-2-(3-pyridyl)thiazol-5-yl]carbamate, 96 mg) as a straw coloured gum.

1H NMR (400 MHz, CDCl$_3$) δ=9.09 (1H, d), 8.65 (1H, dd), 8.18 (1H, d), 7.38 (1H, dd), 5.43 (1H, br.s), 3.30 (3H, s), 2.51 (1H, br. s), 2.35 (3H, s), 1.45 (3H, br. s)

Example 25 Preparation of prop-2-ynyl N-methyl-N-[4-methyl-2-(3-pyridyl)thiazol-5-yl]carbamate (B1)

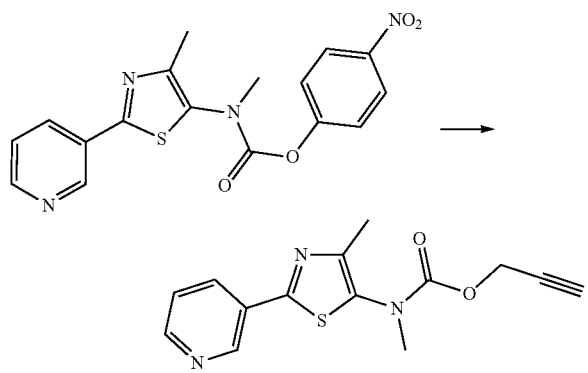

To a flask charged with propargyl alcohol (55.7 mg, 1.00 mmol) dissolved in N,N-dimethylformamide (1.5 mL), and cooled in ice was added sodium hydride (60% suspension in oil w/w) (44 mg, 1.10 mmol). The flask was removed from the ice bath and stirred for 15 mins, then re-cooled with an ice bath. (4-Nitrophenyl) N-methyl-N-[4-methyl-2-(3-pyridyl)thiazol-5-yl]carbamate (200 mg, 0.50 mmol) was added with stirring and cooling. The reaction was warmed to room temperature and stirred for one further hour.

The reaction was quenched with water (6 mL) and extracted three times with EtOAc then the organic extracts washed once with brine. The combined organic extracts were dried over MgSO$_4$, filtered and solvent removed in vacuo. The crude residue was purified via reverse phase flash chromatography using a C$_{18}$ silica column and a water/acetonitrile gradient to afford the desired compound (prop-2-ynyl N-methyl-N-[4-methyl-2-(3-pyridyl)thiazol-5-yl]carbamate, 78 mg) as a straw coloured gum.

1H NMR (400 MHz, CDCl$_3$) δ=9.08 (1H, d), 8.65 (1H, dd), 8.18 (1H, m), 7.38 (1H, dd), 4.72 (2H, br. s), 3.31 (3H, s), 2.51 (1H, br. s), 2.35 (3H, s)

Example 26 Preparation of tert-butyl N-[2-(5-fluoro-3-pyridyl N-oxide)-4-methyl-thiazol-5-yl]-N-methyl-carbamate (A62)

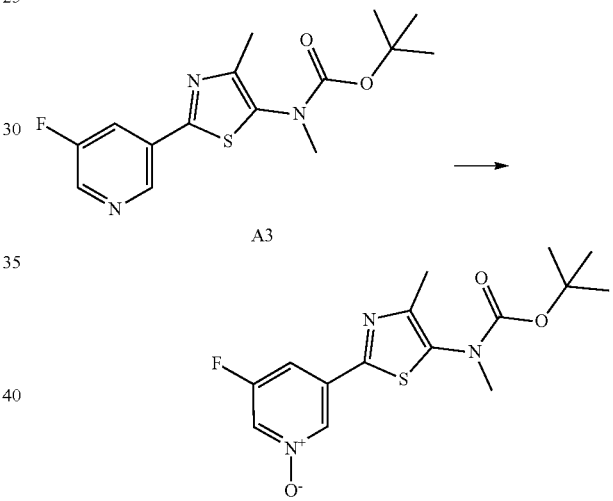

To a flask charged with tert-butyl N-[2-(5-fluoro-3-pyridyl)-4-methyl-thiazol-5-yl]-N-methyl-carbamate (A3) (250 mg, 0.77 mmol) was added CH$_2$Cl$_2$ (25 mL) and the mixture stirred vigorously at 0° C. (ice bath). mCPBA (382 mg, 1.55 mmol) was added as a single portion and mixture was allowed to warm to ambient and left stirring overnight.

The reaction mixture was quenched by the addition of sodium metabisulfite solution (10% w/w, 100 mL) and the phases separated. The organic phase was tested for peroxide (Quantofix® Peroxide 100 test strips, manufactured by Machery-Nagel) and found to be free of residual peroxide.

The reaction mixture was concentrated in vacuo and the residue purified via flash column chromatography on silica gel eluting with an EtOAc/isohexane gradient to give the desired compound (tert-butyl N-[2-(5-fluoro-3-pyridyl N-oxide)-4-methyl-thiazol-5-yl]-N-methyl-carbamate (A62), 14 mg) as a colourless glass 1H NMR (400 MHz, CDCl$_3$) δ=8.55 (1H, s), 8.12 (1H, d), 7.54 (1H, dd), 3.21 (3H, s), 2.32 (3H, s), 1.46 (9H, br. s)

Tables 3 and 4 below shows compound of formula (I) as made using the methods described above, or in analogous manner to the compounds described in Examples 1 to 25.

TABLE 3

Compound of formula (I)

| Compound | Structure | Physical Data (1H NMR, 400 HMz CDCl3 unless stated) |
|---|---|---|
| A1 | 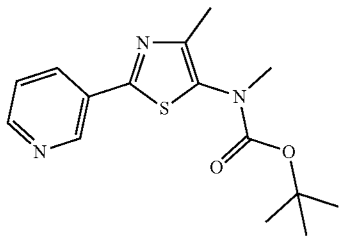 [SMILES: Cc1nc(-c2cccnc2)sc1N(C)C(=O)OC(C)(C)C] | 9.08 (1H, d) 8.63 (1H, dd), 8.17 (1H, d), 7.36 (1H, dd), 3.22 (3H, s), 2.33 (3H, s), 1.44 (9H, br.s.) |
| A2 | 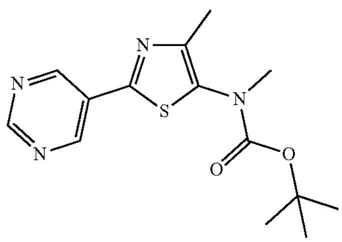 [SMILES: Cc1nc(-c2cncnc2)sc1N(C)C(=O)OC(C)(C)C] | 9.23 (1H, s), 9.18 (2H, s), 3.23 (3H, s), 2.35 (3H, s), 1.45 (9H, br.s.) |
| A3 | 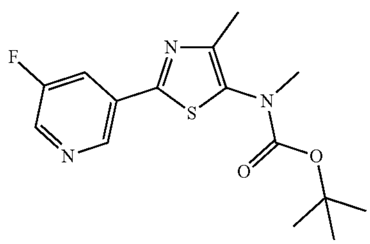 [SMILES: Cc1nc(-c2cncc(F)c2)sc1N(C)C(=O)OC(C)(C)C] | 8.85-8.89 (1H, m), 8.49 (1H, d), 7.93 (1H, dd), 3.23 3H, s), 2.33 (3H, s), 1.45 (9H, br.s.) |
| A4 | 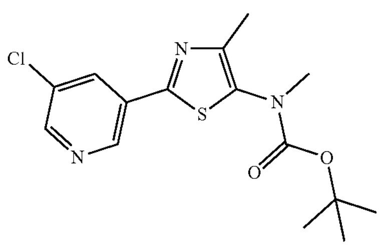 [SMILES: Cc1nc(-c2cncc(Cl)c2)sc1N(C)C(=O)OC(C)(C)C] | 8.92 (1H, d), 8.58 (1H, d), 8.20 (1H, t), 3.23 (3H, s), 2.33 (3H, s), 1.45 (9H, br.s.) |
| A5 | 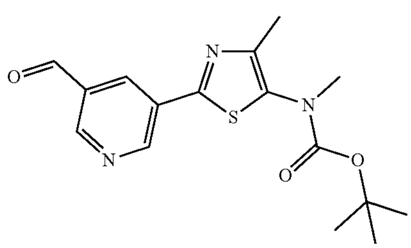 [SMILES: Cc1nc(-c2cncc(C=O)c2)sc1N(C)C(=O)OC(C)(C)C] | 10.2 (1H, s), 9.32 (1H, s), 9.08 (1H, s), 8.58 (1H, s), 3.21 (3H, s), 2.35 (3H, s), 1.44 (9H, br. s) |
| A6 | 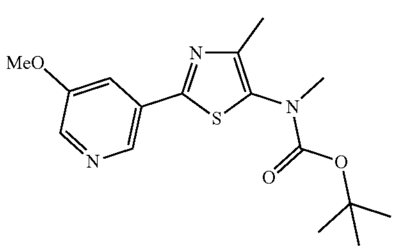 | 8.62 (1H, d), 8.33 (1H, d), 7.71 (1H, br. s), 3.92 (3H, s), 3.21 (3H, s), 2.32 (3H, s), 1.47 (9H, br. s) |

TABLE 3-continued

Compound of formula (I)

| Compound | Structure | Physical Data (1H NMR, 400 HMz CDCl3 unless stated) |
|---|---|---|
| A7 | 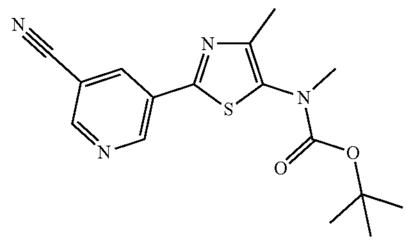 [SMILES: Cc1nc(-c2cncc(C#N)c2)sc1N(C)C(=O)OC(C)(C)C] | 9.23 (1H, d), 8, 87 (1H, d), 8.47 (1H, dd), 3.24 (3H, s), 2.34 (3H, s), 1.45 (9H, br. s) |
| A8 | 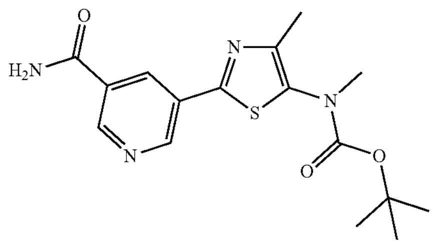 [SMILES: Cc1nc(-c2cncc(C(N)=O)c2)sc1N(C)C(=O)OC(C)(C)C] | (500 MHz, CDCl$_3$) 9.19 (1H, s), 9.07 (1H, s), 8.59 (1H, s), 6.76 (1H, br. s), 6.42 (1H, br. s), 3.23 (3H, s), 2.33 (3H, s), 1.45 (9H, br. s) |
| A9 | 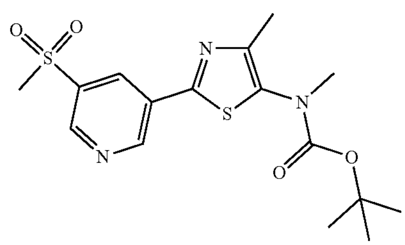 [SMILES: Cc1nc(-c2cncc(S(C)(=O)=O)c2)sc1N(C)C(=O)OC(C)(C)C] | (500 MHz, CDCl$_3$) 9.31 (1H, d), 9.14 (1H, d), 8.69 (1H, m), 3.24 (3H, s), 3.18 (3H, s), 2.35 (3H, s), 1.46 (9H, br. s) |
| A10 | 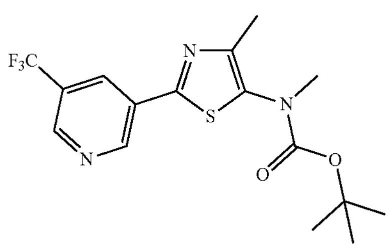 [SMILES: Cc1nc(-c2cncc(C(F)(F)F)c2)sc1N(C)C(=O)OC(C)(C)C] | (500 MHz, CDCl$_3$) 9.23 (1H, d), 8.89 (1H, d), 8.44 (1H, s), 3.25 (3H, m), 2.36 (3H, s), 1.46 (9H, br. s) |
| A11 | 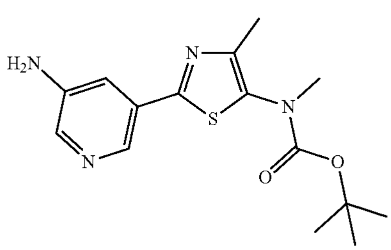 [SMILES: Cc1nc(-c2cncc(N)c2)sc1N(C)C(=O)OC(C)(C)C] | (500 MHz, CDCl$_3$) 8.42 (1H, d), 8.09 (1H, d), 7.49 (1H, s), 4.04 (2H, br. s), 3.21 (3H, s), 2.31 (3H, s), 1.44 (9H, br. s) |
| A12 | 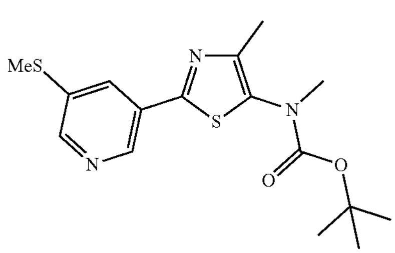 | (500 MHz, CDCl$_3$) 8.79 (1H, d), 8.50 (1H, m), 8.05 (1H, m), 3.23 (3H, s), 2.57 (3H, s), 2.33 (3H, s), 1.59-1.32 (9H, br. s) |

TABLE 3-continued
Compound of formula (I)
| Compound | Structure | Physical Data (1H NMR, 400 HMz CDCl3 unless stated) |
|---|---|---|
| A13 | 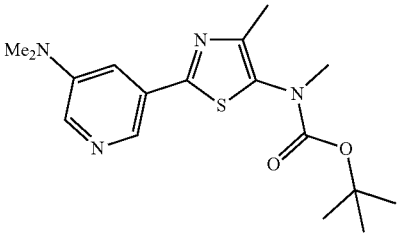 [SMILES: Cc1nc(-c2cncc(N(C)C)c2)sc1N(C)C(=O)OC(C)(C)C] | (500 MHz, CDCl₃) 8.38 (1H, d), 8, 15 (1H, d), 7, 46 (1H, m), 3.22 (3H, s), 3.05 (6H, 2x s), 2.32 (3H, s), 1.44 (9H, br. s) |
| A14 | 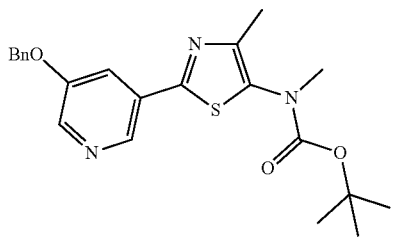 | 8.66 (1H, d), 8.40 (1H, d), 7.80 (1H, dd), 7.48-7.33 (5H, m), 5.18 (2H, s), 3.22 (3H, s), 2.32 (3H, s), 1.44 (9H, br. s) |
| A15 | 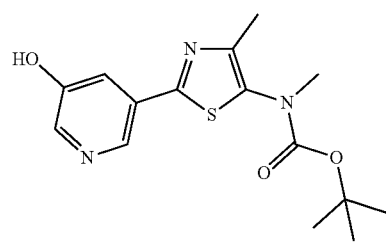 [SMILES: Cc1nc(-c2cncc(O)c2)sc1N(C)C(=O)OC(C)(C)C] | (400 MHz, DMSO-d6) 10.33 (1H, br. s), 8.50 (1H, d), 8.20 (1H, d), 7.60-7.53 (1H, m), 3.15 (3H, s), 2.24 (3H, s), 1.39 (9H, s) |
| A16 | 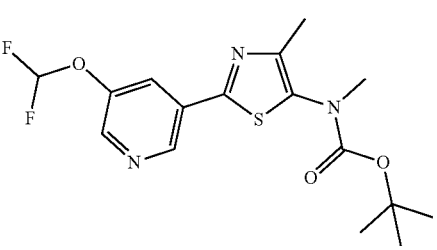 [SMILES: Cc1nc(-c2cncc(OC(F)F)c2)sc1N(C)C(=O)OC(C)(C)C] | 8.91 (1H, d), 8.50 (1H, d), 7.99 (1H, s), 6.82-6.41 (1H, t), 3.23 (3H, s), 2.33 (3H, s), 1.45 (9H, br. s) |
| A17 | 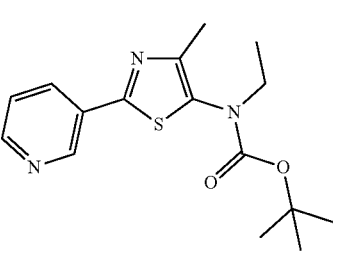 [SMILES: CCN(C(=O)OC(C)(C)C)c1sc(-c2cccnc2)nc1C] | 9.18 (1H, d), 8.62 (1H, dd), 8.17 (1H, m), 7.38 (1H, m), 3.63 (2H, q), 2.32 (3H, s), 1.43 (9H, br. s), 1.18 (3H, t) |
| A18 | 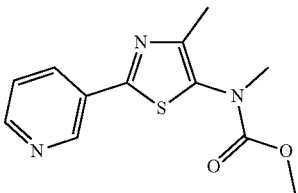 [SMILES: COC(=O)N(C)c1sc(-c2cccnc2)nc1C] | 9.08 (1H, d), 8.64 (1H, dd), 8.17 (1H, dt), 7.37 (1H, m), 3.74 (3H, br. s), 3.28 (3H, s), 2.33 (3H, s) |

TABLE 3-continued

| Compound of formula (I) | | |
|---|---|---|
| Compound | Structure | Physical Data (1H NMR, 400 HMz CDCl3 unless stated) |
| A19 | | 9.08 (1H, d), 8, 64 (1H, dd), 8.17 (1H, m), 7.37 (1H, dd), 4.20 (2H, q), 3.27 (3H, s), 2.33 (3H, s), 1.24 (3H app. br. s) |
| A20 | | 9.09 (1H, d), 8.64 (1H, dd), 8.18 (1H, m), 7.37 (1H, dd), 4.98 (1H, m), 3.26 (3H, s), 2.33 (3H, s), 1.23 (6H, br. d) |
| A21 | | 9.12 (1H, d), 8.67 (1H, dd), 8.19 (1H, m), 7.39 (1H, dd), 4.48 (1H, br. s), 3.20 (3H, s), 2.35 (3H, s), 1.30 (9H, br. s) |
| A22 | | 9.12 (1H, d), 8.66 (1H, dd), 8.20 (1H, m), 7.38 (1H, dd), 3.25 (3H, s), 2.35 (3H, s), 1.47 (9H, m) |
| A23 | | 9.14 (1H, d), 8.68 (1H, dd), 8.25 (1H, m), 7.44 (1H, m), 3.65 (3H, s), 2.32 (3H, s), 1.59 (9H, s) |
| A24 | | 8.89 (1H, s), 8.57 (1H, d), 8.02 (1H, m), 3.27 (3H, s), 1.44 (9H, br. s) |

TABLE 3-continued
Compound of formula (I)
| Compound | Structure | Physical Data (1H NMR, 400 HMz CDCl3 unless stated) |
|---|---|---|
| A25 | 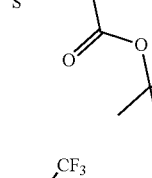 | 9.10 (1H, d), 8.71 (1H, dd), 8.25 (1H, d), 7.42 (1H, dd), 3.27 (3H, s), 1.44 (9H, br.s) |
| A26 | 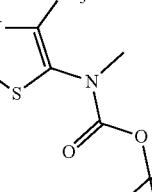 | (500 MHz, CDCl$_3$) 9.31 (1H, s), 9.23 (2H, s), 3.28 (3H, s), 1.44 (9H, br. s) |
| A27 | 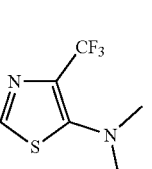 | (500 MHz, CDCl$_3$) 8.94 (1H, d), 8.66 (1H, d), 8.28 (1H, t), 3.27 (3H, s), 1.57-1.33 (9H, br. s) |
| A28 | 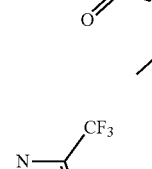 | (500 MHz, CDCl$_3$) 8.64 (1H, d), 8.40 (1H, d), 7.77 (1H, br. s), 3.95 (3H, s), 3.26 (3H, s), 1.43 (9H, br. s) |
| A29 | 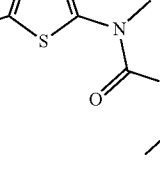 | (300 MHz, CDCl$_3$) 9.08 (1H, s), 8.67 (1H, d), 8.22-8.16 (1H, m), 7.39 (1H, dd), 3.26 (3H, s), 1.46 (9H, s) |
| A30 | 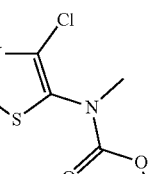 | 9.08 (1H, d), 8.70-8.64 (1H, m), 8.20 (1H, m), 7.42-7.37 (1H, m), 3.25 (3H, s), 1.46 (9H, br. s) |

TABLE 3-continued
Compound of formula (I)
| Compound | Structure | Physical Data (1H NMR, 400 HMz CDCl3 unless stated) |
|---|---|---|
| A31 | 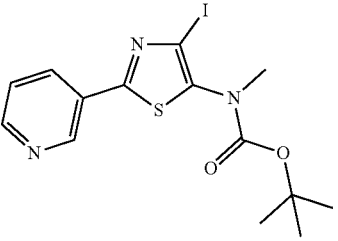 [SMILES: CN(C(=O)OC(C)(C)C)c1sc(-c2cccnc2)nc1I] | 9.08 (1H, d), 8.67 (1H, dd), 8.22 (1H, m), 7.40 (1H, dd), 3.24 (3H, s), 1.46 (9H, br. s) |
| A32 | 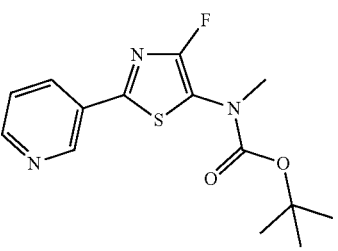 [SMILES: CN(C(=O)OC(C)(C)C)c1sc(-c2cccnc2)nc1F] | (500 MHz, CDCl$_3$) 9.06 (1H, d), 8.65 (1H, d), 8.13 (1H, d), 7.38 (1H, dd), 3.30 (3H, br. s), 1.50 (9H, br. s) |
| A33 | 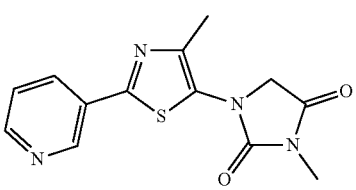 [SMILES: Cc1nc(-c2cccnc2)sc1N1CC(=O)N(C)C1=O] | 9.08 (1H, d), 8.66 (1H, dd), 8.17 (1H, m), 7.39 (1H, m), 4.28 (2H, s), 3.15 (3H, s), 2.43 (3H, s) |
| A34 | 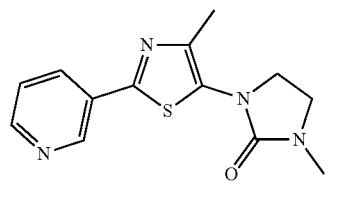 [SMILES: Cc1nc(-c2cccnc2)sc1N1CCN(C)C1=O] | 9.07 (1H, d), 8.62 (1H, dd), 8.15 (1H, m), 7.35 (1H, m), 3.77 (2H, m), 3.54 (2H, m), 2.91 (3H, s), 2.42 (3H, s) |
| A35 | 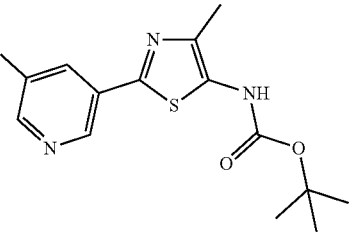 | 8.87 (1H, m), 8.44 (1H, d), 7.94-7.87 (1H, m), 6.73 (1H, br. s), 2.39 (3H, s), 1.55 (9H, s) |
| A38 | 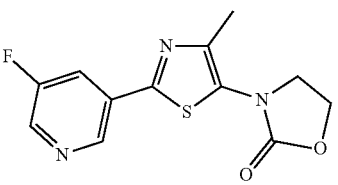 [SMILES: Cc1nc(-c2cncc(F)c2)sc1N1CCOC1=O] | 8.87 (1H, m), 8.51 (1H, d), 7.96-7.90 (1H, m), 4.64-4.53 (2H, m), 4.06-3.97 (2H, m), 2.52 (3H, s) |

TABLE 3-continued

Compound of formula (I)

| Compound | Structure | Physical Data (1H NMR, 400 HMz CDCl3 unless stated) |
|---|---|---|
| A39 | 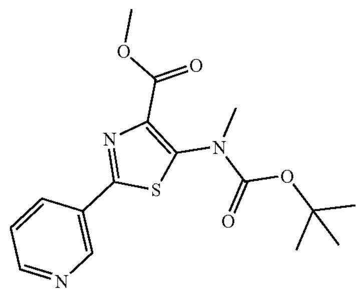 [SMILES: COC(=O)c1nc(-c2cccnc2)sc1N(C)C(=O)OC(C)(C)C] | 9.23 (1H, br. s), 8.80 (1H, d), 8.64 (1H, d), 7.74 (1H, dd), 3.98 (3H, s), 3.31 (3H, s), 1.65-1.32 (9H, br. s) |
| A40 | 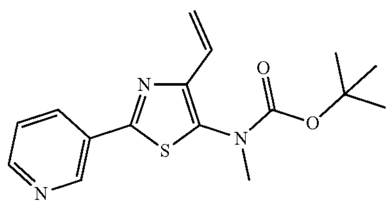 [SMILES: C=Cc1nc(-c2cccnc2)sc1N(C)C(=O)OC(C)(C)C] | 9.08-9.01 (1H, m), 8.58 (1H, dd), 8.16 (1H, dd), 7.31 1H, m), 6.50 (1H, dd), 6.16 (1H, dd), 5.42 (1H, dd), 3.17 (3H, s), 1.36 (9H, br. s) |
| A41 | 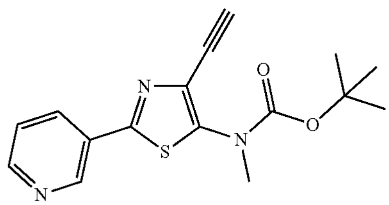 [SMILES: C#Cc1nc(-c2cccnc2)sc1N(C)C(=O)OC(C)(C)C] | 9.09 (1H, d), 8.66 (1H, dd), 8.22 (1H, m), 7.38 (1H, dd), 3.43 (3H, s), 1.81 (1H, s), 1.51 (9H, br. s) |
| A43 | 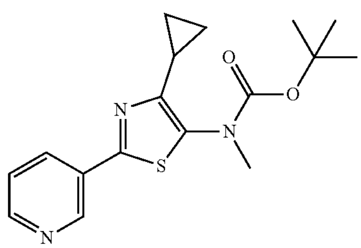 [SMILES: CN(C(=O)OC(C)(C)C)c1sc(-c2cccnc2)nc1C1CC1] | 9.01 (1H, s), 8.60 (1H, d), 8.14 (1H, m), 7.32 (1H, dd), 3.20 (3H, s), 1.89-1.63 (5H, m), 1.39 (9H, br. s) |
| A44 | 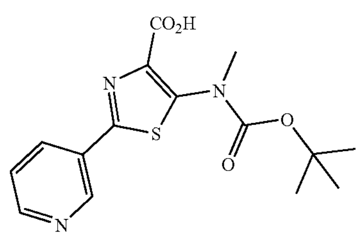 [SMILES: CN(C(=O)OC(C)(C)C)c1sc(-c2cccnc2)nc1C(=O)O] | 9.37 (1H, app. br. s), 8.78 (1H, app. br .s), 8.43 (1H, d), 7.68 (1H, app. br. s), 3.37 (3H, s), 1.46 (9H, br .s) |
| A45 | 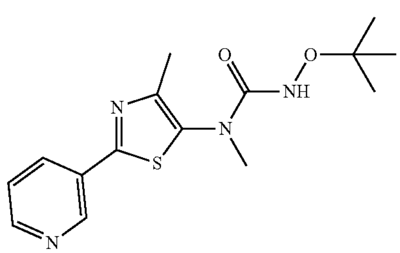 [SMILES: Cc1nc(-c2cccnc2)sc1N(C)C(=O)NOC(C)(C)C] | 9.12 (1H, s), 8.58 (1H, d), 8.18 (1H, d), 7.43 (1H, dd), 5.96 (1H, br. s), 3.28 (3H, s), 2.41 (3H, s), 1.23 (9H, s) |

TABLE 3-continued

Compound of formula (I)

| Compound | Structure | Physical Data (1H NMR, 400 HMz CDCl3 unless stated) |
|---|---|---|
| A50 | 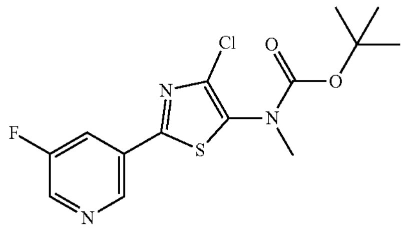 [SMILES: CN(C(=O)OC(C)(C)C)c1sc(-c2cncc(F)c2)nc1Cl] | 8.87 (1H, s), 8.54 (1H, d), 7.95 (1H, m), 3.27 (3H, s), 1.57-1.34 (9H, m) |
| A51 | 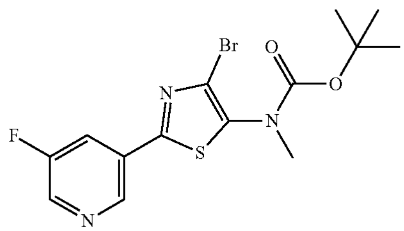 [SMILES: CN(C(=O)OC(C)(C)C)c1sc(-c2cncc(F)c2)nc1Br] | 8.88 (1H, br.s), 8.55 (1H, br.s), 8.06-7.82 (1H, m), 3.26 (3H, s), 1.46 (9H, br.s) |
| A52 | 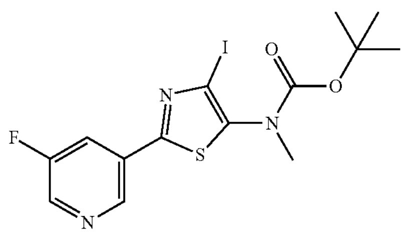 [SMILES: CN(C(=O)OC(C)(C)C)c1sc(-c2cncc(F)c2)nc1I] | 8.87 (s, 1 H), 8.53 (1H, d), 7.97 (1H, m), 3.24 (3H, s), 1.46 (9H, br.s) |
| A61 | 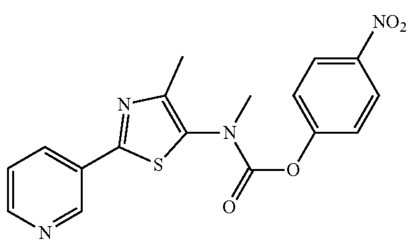 [SMILES: Cc1nc(-c2cccnc2)sc1N(C)C(=O)Oc1ccc([N+](=O)[O-])cc1] | 9.14 (1H, s), 8.67 (1H, dd), 8.33-8.26 (3H, m), 7.39 (1H, dd), 7.23-2.33 (2H, m), 3.40 (3H, s), 2.46 (3H, s) |
| A62 | 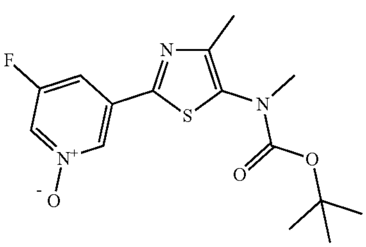 [SMILES: Cc1nc(-c2cc(F)c[n+](O)c2)sc1N(C)C(=O)OC(C)(C)C] | 8.55 (1H, s), 8.12 (1H, d), 7.54 (1H, dd), 3.21 (3H, s), 2.32 (3H, s), 1.46 (9H, br. s) |
| A63 | 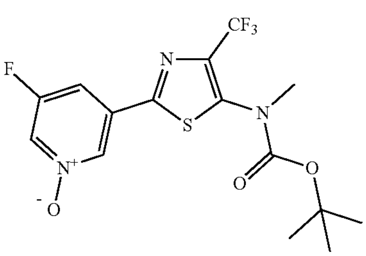 [SMILES: CN(C(=O)OC(C)(C)C)c1sc(-c2cc(F)c[n+](O)c2)nc1C(F)(F)F] | 8.57 (1H, s), 8.21 (1H, d), 7.63 (1H, d), 3.27 (3H, s), 1.44 (9H, s) |

TABLE 4

| Compounds of formula (I) | | |
|---|---|---|
| Compound | Structure | Physical Data |
| B1 | | 9.08 (1H, d), 8.65 (1H, dd), 8.18 (1H, m), 7.38 (1H, dd), 4.72 (2H, br. s), 3.31 (3H, s), 2.51 (1H, br. s), 2.35 (3H, s) |
| B2 | | 9.09 (1H, d), 8.65 (1H, dd), 8.18 (1H, d), 7.38 (1H, dd), 5.43 (1H, br.s), 3.30 (3H, s), 2.51 (1H, br. s), 2.35 (3H, s), 1.45 (3H, br. s) |
| B3 | | 9.09 (1H, d), 8.64 (1H, dd), 8.18 (1H, d), 7.37 (1H, dd), 3.27 (3H, s), 2.59 (1H, s), 2.5 (3H, s), 1.81-1.53 (6H, br. s) |
| B10 | | 8.87 (1H, s), 8.50 (1H, d), 7.95 (1H, d), 3.28 (3H, s), 2.59 (1H, s), 2.35 (3H, s), 1.64 (6H, br.s) |
| B11 | | 8.87 (1H, s), 8.51 (1H, d), 7.95 (1H, m), 4.73 (2H, br .s), 3.30 (3H, s), 2.51 (1H, br. s), 2.36 (3H, s) |
| B12 | | 8.87 (1H, s), 8.50 (1H, d), 7.95 (1H, m), 4.70 (2H, br. s), 3.30 (3H, s), 2.35 (3H, s), 1.85 (3H, s) |

BIOLOGICAL EXAMPLES

B1 Pre-Emergence Herbicidal Activity

Seeds of a variety of test species were sown in standard soil in pots: *Triticum aestivium* (TRZAW), *Oryza sativa* (ORYSA), *Avena fatua* (AVEFA), *Alopecurus myosuroides* (ALOMY), *Echinochloa crus-galli* (ECHCG), *Lolium perenne* (LOLPE), *Zea Mays* (ZEAMX), *Abutilon theophrasti* (ABUTH), *Amaranthus retroflexus* (AMARE) and *Setaria faberi* (SETFA). After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Tables 5 and 6.

B2 Post-Emergence Herbicidal Activity

Seeds of a variety of test species were sown in standard soil in pots: *Triticum aestivium* (TRZAW), *Oryza sativa* (ORYSA), *Avena fatua* (AVEFA), *Alopecurus myosuroides* (ALOMY), *Echinochloa crus-galli* (ECHCG), *Lolium perenne* (LOLPE), *Zea Mays* (ZEAMX), *Abutilon theophrasti* (ABUTH), *Amaranthus retroflexus* (AMARE) and *Setaria faberi* (SETFA). After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Tables 7 and 8.

TABLE 5

Control of weed species by compound of formula (I) after pre-emergence application at a rate of 1000 g/Ha

| Compound | ORYSA | TRZAW | ALOMY | AVEFA | LOLPE | ECHCG |
|---|---|---|---|---|---|---|
| A1 | 2 | 2 | 2 | 4 | 2 | 4 |
| A2 | 1 | 0 | 0 | 3 | 2 | 5 |
| A3 | 1 | 1 | 1 | 3 | 2 | 4 |
| A4 | 0 | 0 | 1 | 4 | 2 | 4 |
| A5 | 0 | 0 | 0 | 0 | 0 | 0 |
| A6 | 1 | 0 | 1 | 0 | 1 | 2 |
| A7 | 1 | 1 | 1 | 4 | 2 | 2 |
| A8 | 0 | 0 | 0 | 0 | 0 | 0 |
| A9 | 0 | 0 | 0 | 0 | 0 | 0 |
| A10 | 1 | 1 | 0 | 1 | 1 | 1 |
| A11 | 2 | 2 | 1 | 1 | 0 | 2 |
| A12 | 0 | 0 | 0 | 3 | 1 | 3 |
| A13 | 1 | 0 | 0 | 0 | 0 | 1 |
| A14 | 0 | 1 | 0 | 0 | 1 | 0 |
| A15 | 0 | 0 | 0 | 0 | 0 | 0 |
| A16 | 1 | 3 | 0 | 3 | 4 | 4 |
| A17 | 0 | 0 | 0 | 0 | 0 | 0 |
| A18 | 0 | 1 | 1 | 2 | 2 | 5 |
| A19 | 0 | 0 | 1 | 1 | 1 | 5 |
| A20 | 0 | 0 | 0 | 2 | 2 | 5 |
| A21 | 0 | 0 | 0 | 2 | 1 | 5 |
| A22 | 0 | 0 | 0 | 0 | 0 | 0 |
| A23 | 0 | 0 | 0 | 0 | 0 | 0 |
| A24 | 0 | 1 | 2 | 4 | 3 | 4 |
| A25 | 1 | 0 | 1 | 4 | 3 | 4 |
| A26 | 1 | 0 | 2 | 4 | 3 | 4 |
| A27 | 0 | 0 | 0 | 2 | 2 | 2 |
| A28 | 0 | 0 | 0 | 1 | 2 | 3 |
| A29 | 2 | 3 | 1 | 2 | 2 | 3 |
| A30 | 1 | 0 | 1 | 3 | 2 | 4 |
| A31 | 1 | 1 | 1 | 1 | 2 | 3 |
| A32 | 2 | 0 | 0 | 1 | 1 | 2 |
| A38 | 3 | 0 | 1 | 1 | 2 | 5 |
| A45 | 2 | 1 | 2 | 3 | 2 | 3 |
| A51 | 0 | 0 | 0 | 2 | 3 | 1 |
| A52 | 1 | 0 | 0 | 3 | 3 | 2 |
| A62 | 1 | 1 | 2 | 2 | 2 | 3 |
| A63 | 0 | 0 | 0 | 1 | 1 | 1 |

TABLE 6

Control of weed species by compound of formula (I)-(i) after pre-emergence application at a rate of 1000 g/Ha

| Compound | ZEAMX | ABUTH | SETFA | AMARE | LOLPE | ECHCG |
|---|---|---|---|---|---|---|
| B1 | 5 | 2 | 5 | 2 | 3 | 2 |
| B2 | 5 | 3 | 5 | 3 | 3 | 1 |
| B3 | 5 | 4 | 4 | 3 | 3 | 3 |

TABLE 7

Control of weed species by compound of formula (I) after post-emergence application at a rate of 1000 g/Ha

| Compound | TRZAW | ORYSA | AVEFA | ALOMY | ECHCG | LOLPE |
|---|---|---|---|---|---|---|
| A1 | 0 | 1 | 4 | 0 | 4 | 4 |
| A2 | 1 | 1 | 5 | 1 | 5 | 3 |
| A3 | 1 | 1 | 4 | 1 | 5 | 3 |
| A4 | 1 | 1 | 5 | 0 | 4 | 2 |
| A5 | 0 | 0 | 0 | 0 | 0 | 0 |
| A6 | 1 | 0 | 2 | 1 | 4 | 2 |
| A7 | 2 | 1 | 4 | 1 | 5 | 3 |
| A8 | 2 | 1 | 2 | 1 | 3 | 0 |
| A9 | 2 | 1 | 2 | 1 | 2 | 1 |
| A10 | 1 | 1 | 2 | 0 | 4 | 0 |
| A11 | 2 | 1 | 1 | 1 | 2 | 1 |
| A12 | 2 | 1 | 2 | 0 | 4 | 3 |
| A13 | 2 | 1 | 0 | 1 | 2 | 0 |
| A14 | 0 | 0 | 0 | 0 | 1 | 0 |
| A15 | 1 | 0 | 2 | 0 | 1 | 1 |
| A16 | 4 | 0 | 5 | 3 | 5 | 4 |
| A17 | 1 | 2 | 4 | 1 | 1 | 2 |
| A18 | 1 | 0 | 3 | 1 | 5 | 2 |
| A19 | 1 | 0 | 3 | 1 | 5 | 2 |
| A20 | 1 | 0 | 3 | 1 | 5 | 3 |
| A21 | 1 | 0 | 4 | 2 | 5 | 3 |
| A22 | 0 | 0 | 2 | 0 | 2 | 2 |
| A23 | 0 | 0 | 1 | 0 | 1 | 0 |
| A24 | 1 | 2 | 4 | 0 | 5 | 4 |
| A25 | 2 | 1 | 4 | 1 | 5 | 4 |
| A26 | 1 | 2 | 5 | 0 | 5 | 4 |
| A27 | 2 | 1 | 4 | 1 | 5 | 3 |
| A28 | 1 | 1 | 2 | 1 | 4 | 3 |
| A29 | 1 | 1 | 4 | 1 | 5 | 4 |
| A30 | 2 | 1 | 4 | 1 | 5 | 4 |
| A31 | 1 | 1 | 5 | 1 | 4 | 3 |
| A32 | 0 | 1 | 3 | 1 | 3 | 2 |
| A35 | 1 | 0 | 1 | 0 | 2 | 0 |

TABLE 7-continued

Control of weed species by compound of formula (I) after post-emergence application at a rate of 1000 g/Ha

| Compound | TRZAW | ORYSA | AVEFA | ALOMY | ECHCG | LOLPE |
|---|---|---|---|---|---|---|
| A38 | 1 | 0 | 4 | 1 | 5 | 3 |
| A45 | 2 | 2 | 5 | 1 | 4 | 4 |
| A51 | 0 | 0 | 4 | 0 | 4 | 2 |
| A52 | 1 | 0 | 4 | 1 | 4 | 3 |
| A61 | 1 | 0 | 2 | 0 | 1 | 1 |
| A62 | 1 | 0 | 4 | 1 | 4 | 4 |
| A63 | 0 | 0 | 3 | 1 | 5 | 2 |

TABLE 8

Control of weed species by compound of formula (I)-(i) after post-emergence application at a rate of 1000 g/Ha

| Compound | SETFA | ZEAMX | ECHCG | LOLPE | AMARE | ABUTH |
|---|---|---|---|---|---|---|
| B1 | 5 | 5 | 4 | 3 | 1 | 1 |
| B2 | 5 | 4 | 2 | 4 | 2 | 2 |
| B3 | 5 | 5 | 4 | 4 | 2 | 1 |

The invention claimed is:

1. A compound of formula (I)

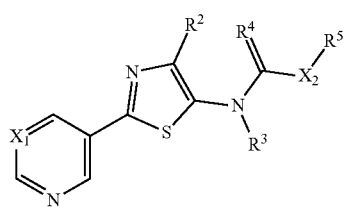

(I)

or a salt or N-oxide thereof, wherein, $X_1$ is N or $CR^1$;

$R^1$ is hydrogen, halogen, cyano, $C_1$-$C_6$alkyl, $C_3$-$C_6$cycloalkyl, $C_2$-$C_6$alkenyl, $C_2$-$C_6$alkynyl, $C_1$-$C_6$alkoxy, —C(O)$OR^6$ or $S(O)_n$($C_1$-$C_6$alkyl), formyl, hydroxyl, —C(O)$NR^6R^7$, $NR^6R^7$, benzyloxy, $C_1$-$C_6$ haloalkoxy, or $C_1$-$C_6$ haloalkyl;

$R^2$ is hydrogen, halogen, cyano, nitro, $C_1$-$C_6$ alkyl, $C_1$-$C_6$haloalkyl, $C_2$-$C_6$alkenyl, $C_2$-$C_6$ alkynyl, $C_3$-$C_6$cycloalkyl, —C(O)$OR^6$, $S(O)_n$($C_1$-$C_6$alkyl), $C_1$-$C_6$ alkoxy, or $C_1$-$C_6$ haloalkoxy;

n is 0, 1, or 2;

$R^3$ is hydrogen, cyano, $C_1$-$C_6$alkyl, $C_2$-$C_6$ alkenyl, $C_2$-$C_6$ alkynyl, $C_2$-$C_6$haloalkenyl, $C_1$-$C_6$ alkoxy, $C_1$-$C_6$ haloalkyl, $C_1$-$C_6$haloalkoxy, $C_2$-$C_6$alkenyloxy, $C_3$-$C_{10}$cycloalkyl, $NR^6R^7$, $R^4$ is O, S, or N($C_1$-$C_6$alkyl);

$X_2$ is O, S, or $NR^8$;

$R^5$ is $C_2$-$C_6$alkynyl or $R^3$ and $R^8$ together with the atoms to which they are attached form a saturated or partially unsaturated 5-9 membered ring system optionally comprising 1 to 3 heteroatoms independently selected from S, O and N and optionally substituted with 1 to 3 groups independently selected from halogen or $C_1$-$C_6$ alkyl;

$R^6$ and $R^7$ are each independently hydrogen, $C_1$-$C_6$ alkyl, $C_1$-$C_6$ haloalkyl, $C_2$-$C_6$ alkenyl, or $C_2$-$C_6$ alkynyl, or $R^6$ and $R^7$ together with the nitrogen atom to which they are attached form a saturated or partially unsaturated 3-6 membered ring optionally comprising 1 to 3 heteroatoms independently selected from S, O and N and optionally substituted with 1 to 3 groups independently selected from halogen or $C_1$-$C_6$ alkyl;

$R^8$ is hydrogen, cyano, $C_1$-$C_6$ alkyl, $C_1$-$C_6$ haloalkyl, $C_2$-$C_6$ alkenyl, or $C_2$-$C_6$ alkynyl; $C_1$-$C_6$alkoxy, $C_1$-$C_6$haloalkoxy, $C_2$-$C_6$alkenyloxy, $C_2$-$C_6$alkynyloxy, $C_3$-$C_{10}$cycloalkyloxy, $C_3$-$C_{10}$ cycloalkenyloxy, $C_2$-$C_6$haloalkenyloxy;

or $R^7$ and $R^8$ together with the carbon atoms to which they are attached form a saturated or partially unsaturated 3-9 membered ring optionally comprising 1 to 3 heteroatoms independently selected from S, O and N and optionally substituted with 1 to 3 groups independently selected from halogen or $C_1$-$C_6$ alkyl.

2. The compound of claim 1, wherein $R^1$ is hydrogen, halogen, formyl, cyano, $C_1$-$C_6$ alkoxy, $C_1$-$C_6$ alkylsulfonyl, $C_1$-$C_6$ alkylthio, $C_1$-$C_6$ haloalkoxy, —C(O)$NR^6R^7$, $NR^6R^7$, or $C_1$-$C_6$ haloalkyl.

3. The compound of claim 1, wherein $R^2$ is halogen, cyano, nitro, $C_1$-$C_6$ alkyl, $C_1$-$C_6$ haloalkyl, $C_2$-$C_6$ alkenyl, $C_1$-$C_6$ alkylsulfinyl, $C_1$-$C_6$ alkylsulfonyl, $C_1$-$C_6$ alkylthio, —C(O)$OR^6$, $C_1$-$C_6$ alkoxy, $C_1$-$C_6$ haloalkoxy, $C_3$-$C_6$ cycloalkyl, or $C_2$-$C_6$ alkynyl.

4. The compound of claim 1, wherein $R^3$ is $C_1$-$C_6$ alkyl, $C_2$-$C_6$ alkenyl, $C_2$-$C_6$ alkynyl, $C_2$-$C_6$ haloalkenyl, $C_1$-$C_6$ alkoxy, $C_1$-$C_6$ haloalkyl, $C_1$-$C_6$ haloalkoxy, $C_2$-$C_6$ alkenyloxy, $C_3$-$C_{10}$ cycloalkyl, or $NR^6R^7$.

5. The compound of claim 1, wherein $R^4$ is O.

6. The compound of claim 1, wherein $X_2$ is O, or $NR^8$.

7. A compound selected from:

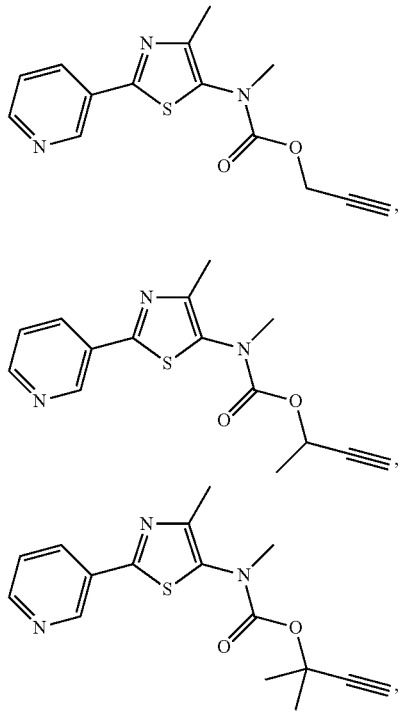

-continued

-continued
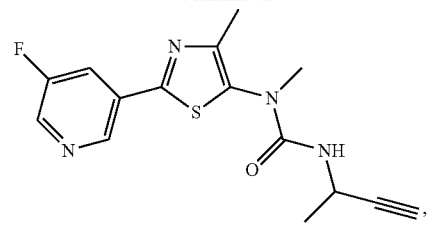
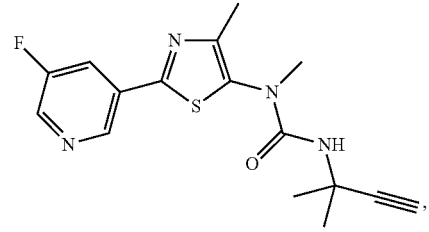
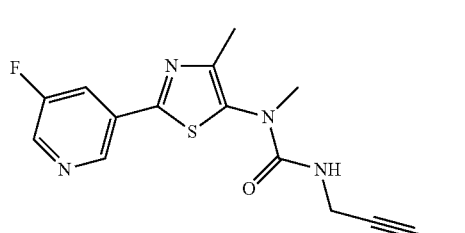
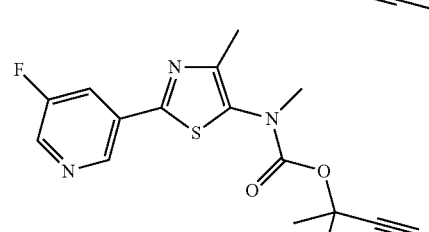
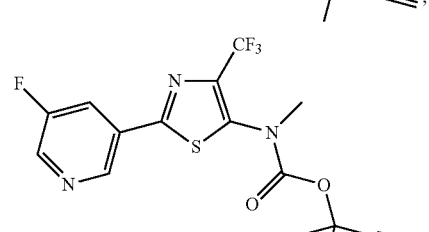
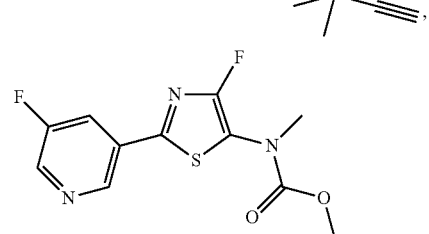
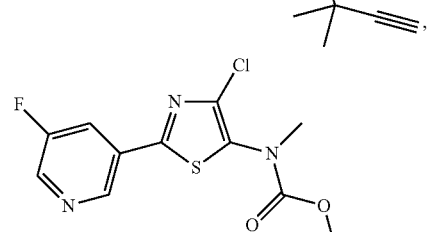
-continued
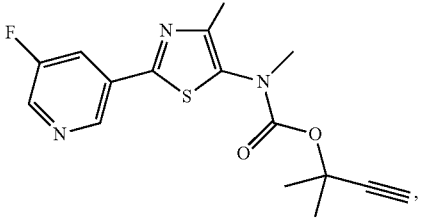
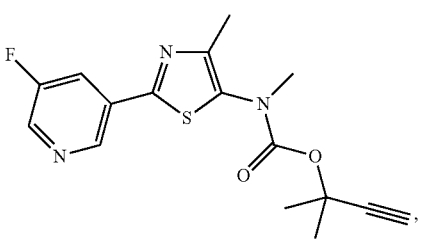
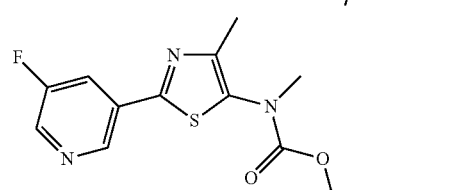
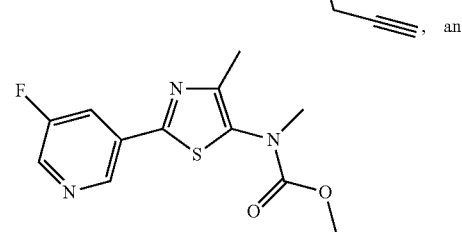
, and
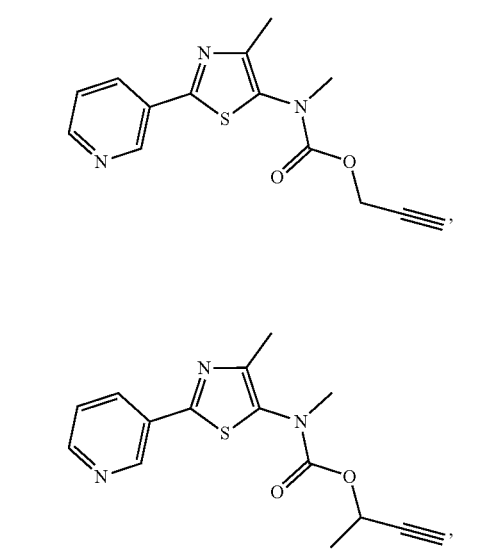
8. The compound of claim 7, wherein the compound is selected from:
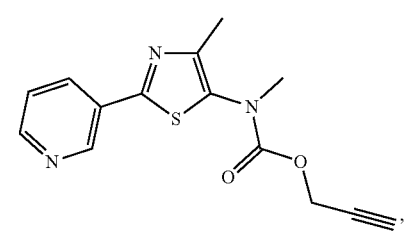
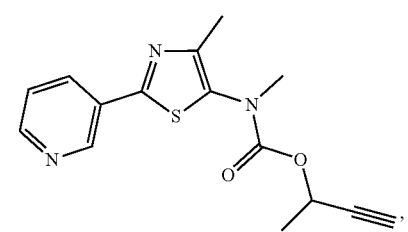

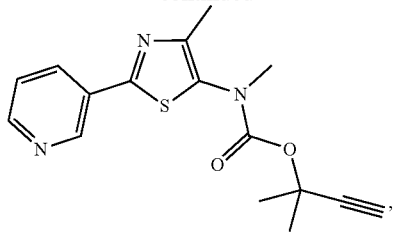

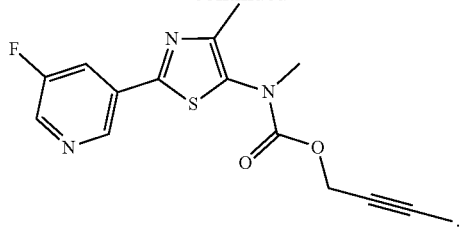

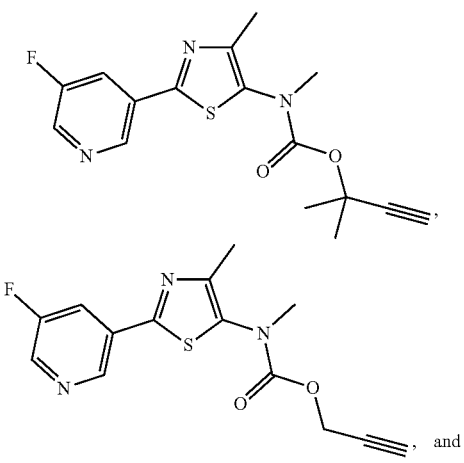
, and

9. An herbicidal composition comprising from 0.1 to 99% by weight, of a compound of Formula (I) as defined in claim 1, and from 1 to 99.9% by weight of a formulation adjuvant, wherein the formulation adjuvant comprises from 0 to 25% by weight of a surface-active substance.

10. The herbicidal composition of claim 9, further comprising at least one additional herbicide or herbicide safener.

11. A method of selectively controlling weeds at a locus comprising crop plants and weeds, wherein the method comprises application to the locus, of a weed-controlling amount at a rate of from 50 to 1000 g/Ha of (i) a compound of formula (I) of claim 1.

12. A method of controlling unwanted plant growth, comprising applying a weed-controlling amount of a compound of formula (I) of claim 1 to the unwanted plants or to a locus thereof, such that the unwanted plants are controlled by killing, reducing or retarding growth, or by preventing or reducing germination thereof.

* * * * *